US008889426B2

(12) United States Patent
Mohammadi et al.

(10) Patent No.: US 8,889,426 B2
(45) Date of Patent: Nov. 18, 2014

(54) METHODS OF IDENTIFYING INHIBITORS OF FGF23 BINDING TO THE BINARY FGFR-KLOTHO COMPLEX FOR THE TREATMENT OF HYPOPHOSPHATEMIA

(75) Inventors: Moosa Mohammadi, Scarsdale, NY (US); Regina Goetz, New York, NY (US); Anna V. Eliseenkova, Stamford, CT (US)

(73) Assignee: New York University, New York, NY (US)

( * ) Notice: Subject to any disclaimer, the term of this patent is extended or adjusted under 35 U.S.C. 154(b) by 0 days.

(21) Appl. No.: 13/475,094

(22) Filed: May 18, 2012

(65) Prior Publication Data

US 2012/0288886 A1 Nov. 15, 2012

Related U.S. Application Data

(62) Division of application No. 12/915,801, filed on Oct. 29, 2010.

(60) Provisional application No. 61/256,361, filed on Oct. 30, 2009.

(51) Int. Cl.
*G01N 33/53* (2006.01)
*A61K 38/17* (2006.01)
*G01N 33/68* (2006.01)
*G01N 33/573* (2006.01)
*A61K 45/06* (2006.01)
*G01N 21/84* (2006.01)
*G01N 30/00* (2006.01)
*A61K 31/59* (2006.01)
*C07K 14/50* (2006.01)

(52) U.S. Cl.
CPC ............. *A61K 38/17* (2013.01); *A61K 38/1709* (2013.01); *G01N 33/68* (2013.01); *G01N 33/573* (2013.01); *A61K 45/06* (2013.01); *G01N 21/84* (2013.01); *G01N 30/00* (2013.01); *A61K 31/59* (2013.01)
USPC ........................... 436/501; 530/350; 530/399

(58) Field of Classification Search
None
See application file for complete search history.

(56) References Cited

U.S. PATENT DOCUMENTS

| | | | |
|---|---|---|---|
| 7,223,563 B2 | 5/2007 | Econs et al. | |
| 7,314,618 B2 | 1/2008 | Econs et al. | |
| 7,745,406 B2 | 6/2010 | Econs et al. | |
| 7,947,810 B2 | 5/2011 | Econs et al. | |
| 2002/0082205 A1 | 6/2002 | Itoh et al. | |
| 2003/0105302 A1 | 6/2003 | Itoh et al. | |
| 2004/0097414 A1 | 5/2004 | Itoh et al. | |
| 2006/0160181 A1* | 7/2006 | Luethy et al. | 435/69.1 |
| 2006/0281679 A1 | 12/2006 | Itoh et al. | |
| 2010/0323954 A1 | 12/2010 | Li et al. | |
| 2011/0104152 A1 | 5/2011 | Sonoda | |
| 2011/0190207 A1 | 8/2011 | Mohammadi et al. | |
| 2013/0331325 A1 | 12/2013 | Mohammadi et al. | |

FOREIGN PATENT DOCUMENTS

| | | |
|---|---|---|
| JP | 2008-117661 | 4/2008 |
| WO | 20011066595 A2 | 9/2001 |
| WO | 20011066596 A2 | 9/2001 |
| WO | 2009/133905 A1 | 11/2009 |

OTHER PUBLICATIONS

Kurosu et al. J. Biol. Chem. 281(10): 6120-6123, 2006.*
Kurosu et al. J. Biol. Chem. 282(37): 26687-26695, 2007.*
Micanovic et al. J. Cell. Physiol. 219: 227-234, 2009.*
Kharitonenkov et al. J. Cell. Physiol. 215: 1-7, 2008.*
Berndt et al., "Biological Activity of FGF-23 Fragments," Eur J Physiol 454:615-623 (2007).
Goetz et al., "Molecular Insights into the Klotho-Dependent, Endocrine Mode of Action of Fibroblast Growth Factor 19 Subfamily Members," Molecular and Cellular Biology 27(9):3417-3428 (2007).
Goetz et al., "Isolated C-Terminal tail of FGF23 Alleviates Hypophosphatemia by Inhibiting FGF23-FGFR-Klotho Complex Formation," PNAS 107(1):407-412 (2010).
Hu et al., "C-terminal Fragments of Fibroblast Growth Factor (FGF) 23 Inhibits Renal Phosphate (Pi) Excretion as an FGF23 Antagonist by Displacing FGF23 from its Receptor," Abstract SA-FC345, J. Am. Soc. Nephrol. 19:78A (2008).
Hu et al., "C-terminal Fragments of Fibroblast Growth Factor (FGF) 23 Inhibit Renal Phosphate Excretion as an FGF23 Antagonist by Displacing FGF23 from its Receptor," Oral Presentation at the 41st Annual Meeting of the American Society of Nephrology (Renal Week 2008) Philadelphia, PA, Nov. 4-9, 2008.
Aono et al., "Therapeutic Effects of Anti-FGF23 Antibodies in Hypophosphatemic Rickets/Osteomalacia," J. Bone Miner. Res. 24(11):1879-1888 (available online May 4, 2009).

(Continued)

*Primary Examiner* — Christine J Saoud
(74) *Attorney, Agent, or Firm* — LeClairRyan, a Professional Corporation

(57) ABSTRACT

The present invention is directed to a method of treating hypophosphatemia in a subject. The present invention is also directed to a method of screening for compounds suitable for treatment of hypophosphatemia associated with elevated or normal FGF23. This method involves providing FGF23, FGFR-Klotho complex, and one or more candidate compounds. The FGF23, the FGFR-Klotho complex, and the candidate compounds are combined under conditions effective for the FGF23 and the binary FGFR-Klotho complex to form a ternary complex if present by themselves. This method also involves identifying the candidate compounds, which prevent formation of the complex as being potentially suitable in treating hypophosphatemic conditions associated with elevated or normal FGF23. A method of screening the specificity of compounds which prevent formation of the FGF23-Klotho-FGFR complex is also disclosed.

13 Claims, 22 Drawing Sheets

(56) References Cited

OTHER PUBLICATIONS

Aono et al., "The Neutralization of FGF-23 Ameliorates Hypophosphatemia and Rickets in Hyp Mice," Abstract, Oral Presentation, No. 1056, 25th American Society for Bone and Mineral Research Meeting, Sep. 19-23, 2003, Minneapolis, Minnesota, J. Bone Miner. Res. 18 (Suppl. S1): S15 (2003).

Shimada et al., "Mutant FGF-23 Responsible for Autosomal Dominant Hypophosphatemic Rickets Is Resistant to Proteolytic Cleavage and Causes Hypophosphatemia in Vivo," Endocrinology 143(8):3179-82 (2002).

Shimada et al., "Neutralization of Intrinsic FGF-23 Action by Antibodies Reveals the Essential Role of FGF-23 in Physiological Phosphate and Vitamin D Metabolism," Abstract, Poster Presentation, Nos. SA414 and F414, 25th American Society for Bone and Mineral Research Meeting, Sep. 19-23, 2003, Minneapolis, Minnesota, J. Bone Miner. Res. 18 (Suppl. S1): S93, S164 (2003).

Wu et al., "C-terminal Tail of FGF19 Determines its Specificity Towards Klotho Co-receptors," J.Biol Chem. 283 (48):33304-33309 (2008).

Yamazaki et al., "Anti-FGF23 Neutralizing Antibodies Show the Physiological Role and Structural Features of FGF23," J. Bone Miner. Res. 23(9):1509-1518 (available online Apr. 1, 2008).

Shimada, "Possible Roles of Fibroblast Growth Factor 23 in Developing X-Linked Hypophosphatemia," Clin. Pediatr. Endocrinol. 14(Suppl 23):33-37 (2005).

Perwad et al. "Fibroblast Growth Factor 23 Impairs Phosphorus and Vitamin D Metabolism in Vivo and Suppresses 25-Hydroxyvitamin D-1alpha-Hydroxylase Expression in Vitro," Am. J. Physiol. Renal Physiol. 293:F1577-F1583 (2007).

Office Action for U.S. Appl. No. 13/763,301 (Apr. 1, 2014) Do not print.

Beenken et al., "The FGF Family: Biology, Pathophysiology and Therapy," Nat Rev Drug Discov. 8(3):235-53 (Mar. 2009).

Razzaque, "The FGF23-Klotho Axis: Endocrine Regulation of Phosphate Homeostasis," Nat. Rev. Endocrinol. 5 (11):611-19 (Nov. 2009).

Wu et al., "Separating Mitogenic and Metabolic Activities of Fibroblast Growth Factor 19 (FGF19)," Proc. Nat'l. Acad. Sci. USA 107(32):14158-14163 (Epub Jul. 26, 2010).

* cited by examiner

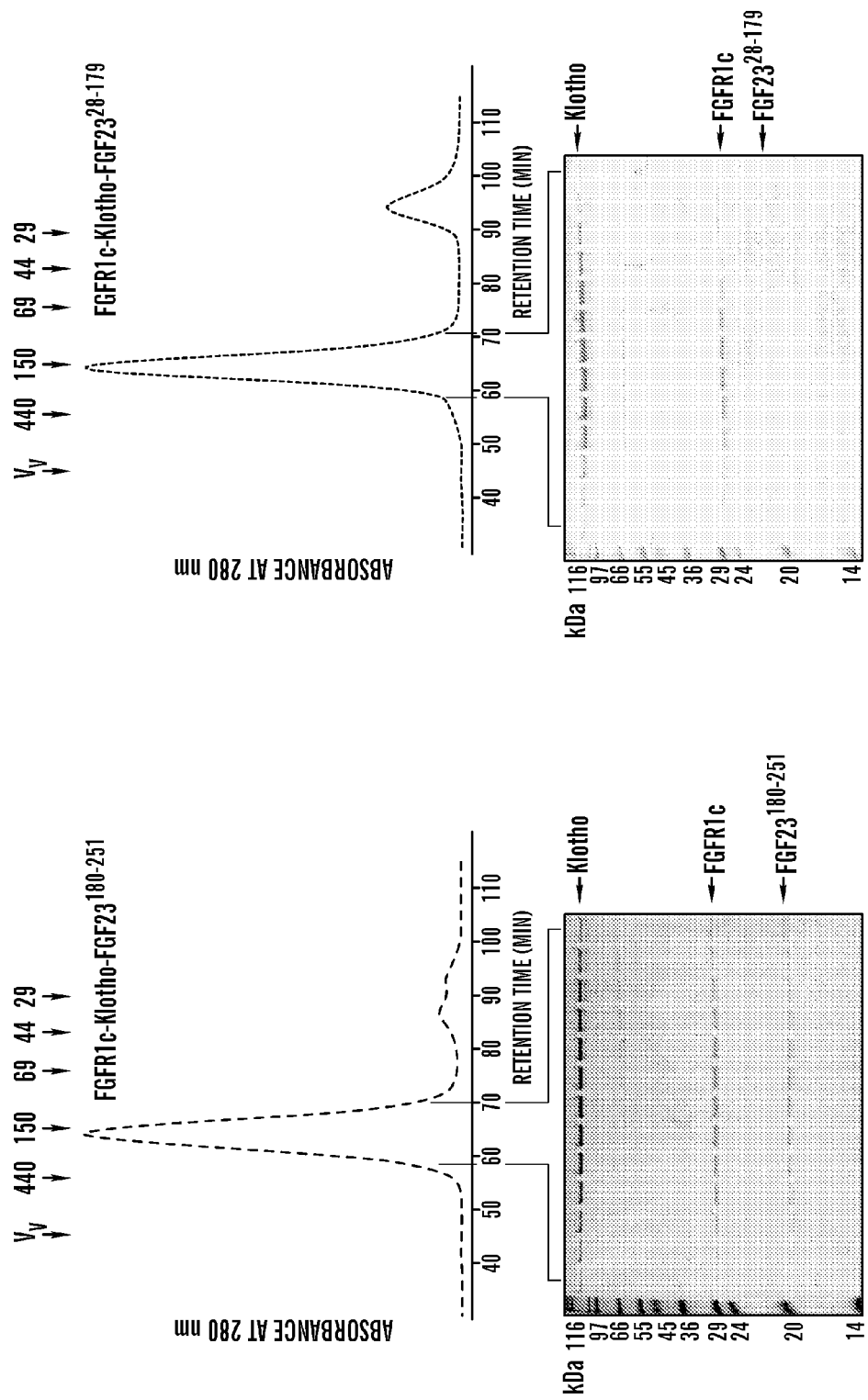

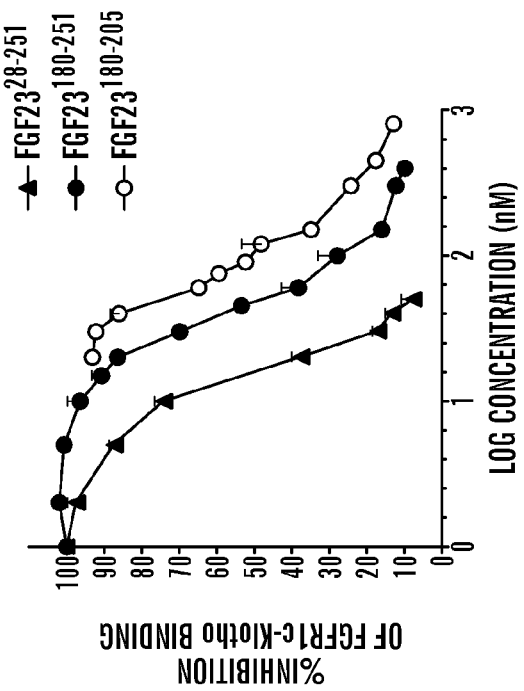
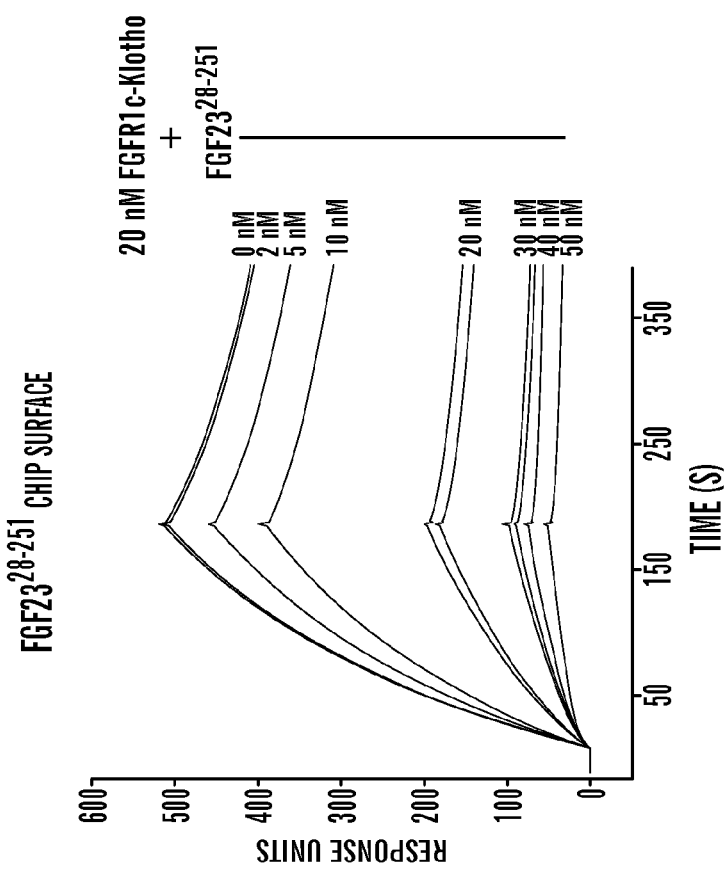
FIG. 3D
FIG. 3C

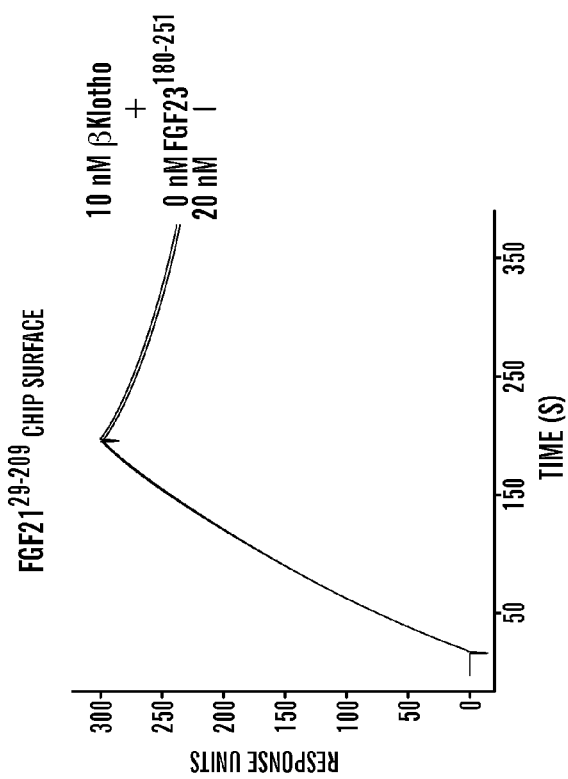
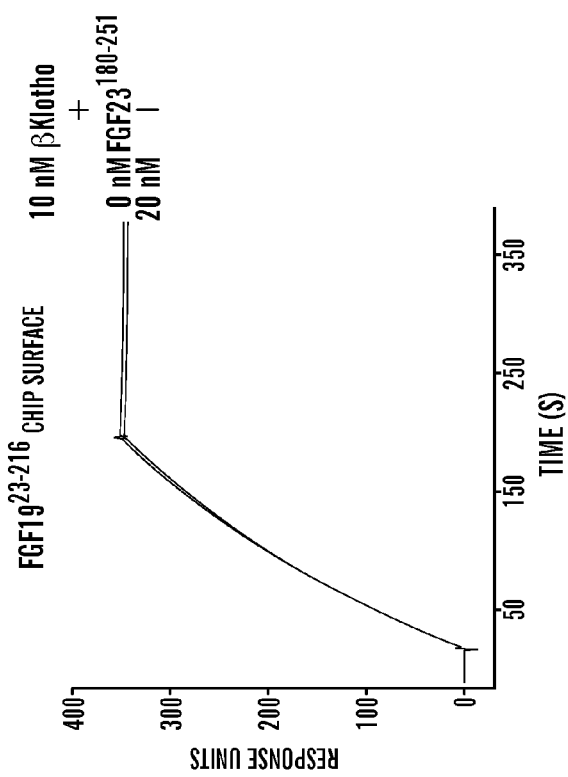
FIG. 4A
FIG. 4B

METHODS OF IDENTIFYING INHIBITORS OF FGF23 BINDING TO THE BINARY FGFR-KLOTHO COMPLEX FOR THE TREATMENT OF HYPOPHOSPHATEMIA

This application is a division of U.S. patent application Ser. No. 12/915,801, filed Oct. 29, 2010, which claims the benefit of U.S. Provisional Patent Application Ser. No. 61/256,361, filed Oct. 30, 2009, each of which is hereby incorporated by reference in its entirety.

The subject matter of this application was made with support from the United States Government under National Institutes of Health (NIH) grant numbers DE13686, AG19712, AG25326, DK48482, DK20543, and DK077276. The U.S. government has certain rights.

FIELD OF THE INVENTION

The present invention is directed to inhibiting binding of FGF23 to the binary FGFR-Klotho complex for the treatment of hypophosphatemia.

BACKGROUND OF THE INVENTION

Inorganic phosphate plays a key role in a myriad of biological processes, including bone mineralization, reversible regulation of protein function by phosphorylation, and production of adenosine triphosphate. Plasma levels of phosphate range between 2.2 and 4.9 mg/dl (Dwyer et al., "Severe Hypophosphatemia in Postoperative Patients," *Nutr Clin Pract* 7(6):279-283 (1992), Alon et al., "Calcimimetics as an Adjuvant Treatment for Familial Hypophosphatemic Rickets," *Clin J Am Soc Nephrol* 3: 658-664 (2008)), and are primarily regulated by modifying renal tubular reabsorption. Because of phosphate's pleiotropic activity, imbalances in phosphate homeostasis adversely affect essentially every major tissue/organ.

Hypophosphatemia is a common clinical condition with an incidence ranging from 0.2-3.1% in all hospital admissions to 21.5-80% in specific subgroups of hospitalized patients (Gaasbeek et al., "Hypophosphatemia: An Update on its Etiology and Treatment," *Am J Med* 118(10):1094-1101 (2005), Brunelli et al., "Hypophosphatemia: Clinical Consequences and Management," *J Am Soc Nephrol* 18(7):1999-2003 (2007)). Acute clinical manifestations of hypophosphatemia include respiratory failure, cardiac arrhythmia, hemolysis, rhabdomyolysis, seizures, and coma. Chronic clinical manifestations of hypophosphatemia include myalgia and osteomalacia (Gaasbeek et al., "Hypophosphatemia: An Update on its Etiology and Treatment," *Am J Med* 118(10):1094-1101 (2005)). Hypophosphatemia originates from diverse pathophysiologic mechanisms, most importantly from renal phosphate wasting, an inherited or acquired condition in which renal tubular reabsorption of phosphate is impaired (Imel et al., "Fibroblast Growth Factor 23: Roles in Health and Disease," *J Am Soc Nephrol* 16(9):2565-2575 (2005); Negri A., "Hereditary Hypophosphatemias: New Genes in the Bone-kidney Axis," *Nephrology (Carlton)* 12(4):317-320 (2007)). Hypophosphatemia can also be associated with alcoholic and diabetic ketoacidosis, acute asthma, chronic obstructive pulmonary disease, sepsis, recovery from organ transplantation, and the "refeeding syndrome", which refers to metabolic disturbances seen in malnourished patients on commencing nutrition (Gaasbeek et al., "Hypophosphatemia: An Update on its Etiology and Treatment," *Am J Med* 118(10):1094-1101 (2005), Miller et al., "Hypophosphatemia in the Emergency Department Therapeutics," *Am J Emerg Med* 18(4):457-461 (2000), Marinella M A., "Refeeding Syndrome and Hypophosphatemia," *J Intensive Care Med* 20(3):155-159 (2005)).

Oral or intravenous administration of inorganic phosphate salts is the current mainstay for the management of hypophosphatemia. Oral phosphate therapy requires high doses, which frequently lead to diarrhea or gastric irritation (Shiber et al., "Serum Phosphate Abnormalities in the Emergency Department," *J Emerg Med* 23(4):395-400 (2002)). For intravenous phosphate therapy, the response to any given dose is sometimes unpredictable (Bohannon N J., "Large Phosphate Shifts with Treatment for Hyperglycemia," *Arch Intern Med* 149(6):1423-1425 (1989), Charron et al., "Intravenous Phosphate in the Intensive Care Unit: More Aggressive Repletion Regimens for Moderate and Severe Hypophosphatemia," *Intensive Care Med* 29(8):1273-1278 (2003); Rosen et al., "Intravenous Phosphate Repletion Regimen for Critically Ill patients with Moderate Hypophosphatemia," *Crit Care Med* 23(7):1204-1210 (1995)), and complications include "overshoot" hyperphosphatemia, hypocalcemia, and metastatic calcification (Gaasbeek et al., "Hypophosphatemia: An Update on its Etiology and Treatment," *Am J Med* 118(10):1094-1101 (2005); Shiber et al., "Serum Phosphate Abnormalities in the Emergency Department," *J Emerg Med* 23(4):395-400 (2002)). In addition, parenteral regimens are not practical for chronic disorders. Most importantly, replacement therapy alone is never adequate when there is significant renal phosphate wasting. Therefore, novel strategies for the treatment of hypophosphatemia are needed.

Kidney transplantation is the preferred treatment of end-stage renal failure, and hypophosphatemia is a well recognized problem during the first weeks after engraftment. The majority of kidney transplant patients often experience excessive renal phosphate leakage (Schwarz et al., "Impaired Phosphate Handling of Renal Allografts is Aggravated under Rapamycin-based Immunosuppression," *Nephrol Dial Transplant* 16: 378-382 (2001); Moorhead et al., "Hypophosphataemic Osteomalacia after Cadaveric Renal Transplantation," *Lancet* 1(7860):694-697 (1974)), because the transplanted kidneys only marginally reabsorb the urinary phosphate to the circulation. The reasons for this poor reabsorbing activity on the part of transplanted kidneys are unknown. It frequently causes the patients malnutrition and secondary osteoporosis. This problem cannot be treated by a simple exogenous supplementation of phosphate. Similar renal phosphate leakage with unknown pathology is often observed in pediatric medicine, with outcomes such as malnutrition or growth retardation.

A recent study in adults demonstrated that as many as 93% of patients develop moderate to severe hypophosphatemia (serum phosphate concentration 0.9-2.25 mg/dL), an average of 5 weeks following transplantation (Ambuhl et al., "Metabolic Aspects of Phosphate Replacement Therapy for Hypophosphatemia After Renal Transplantation: Impact on Muscular Phosphate Content, Mineral Metabolism, and Acid/base Homeostasis," *Am J Kidney Dis* 34:875-83 (1999)).

Health problems associated with circulating phosphate shortage are not limited to humans. Dairy cows sometimes suffer from hypophosphatemia (too low phosphate in the blood) caused by overproduction of the milk. It not only deteriorates the nutritional quality of the milk but also often make the cows useless for milk production. It is a relatively common problem in dairy farms (Goff, J P., "Pathophysiology of Calcium and Phosphorus Disorders," *Vet Clin North Am Food Anim Pract* 16(2):319-37 (2000), Oetzel, G R., "Management of Dry Cows for the Prevention of Milk Fever and Other Mineral Disorders," *Vet Clin North Am Food Anim Pract* 16(2):369-86 (2000)).

Fibroblast growth factor (FGF) 23, is an endocrine regulator of phosphate homeostasis, and was originally identified as the mutated gene in patients with the phosphate wasting disorder "autosomal dominant hypophosphatemic rickets" (ADHR) (Anonymous., "Autosomal Dominant Hypophosphataemic Rickets is Associated with Mutations in FGF23," *Nat Genet* 26(3):345-348 (2000)). FGF23 inhibits reabsorption of phosphate in the renal proximal tubule by decreasing the abundance of the type II sodium-dependent phosphate transporters $NaP_i$-2A and $NaP_i$-2C in the apical brush border membrane (Baum et al., "Effect of Fibroblast Growth Factor-23 on Phosphate Transport in Proximal Tubules," *Kidney Int* 68(3):1148-1153 (2005); Perwad et al., "Fibroblast Growth Factor 23 Impairs Phosphorus and Vitamin D Metabolism In Vivo and Suppresses 25-hydroxyvitamin D-1alpha-hydroxylase Expression In Vitro," *Am J Physiol Renal Physiol* 293 (5):F1577-1583 (2007); Larsson et al., "Transgenic mice expressing fibroblast growth factor 23 under the control of the alpha1(I) collagen promoter exhibit growth retardation, osteomalacia, and disturbed phosphate homeostasis," *Endocrinology* 145(7):3087-3094 (2004)). The phosphaturic activity of FGF23 is down-regulated by proteolytic cleavage at the $^{176}RXXR^{179}$ (SEQ ID NO: 1) motif, where "XX" is defined as "HT", corresponding to positions 177 and 178, respectively, of the FGF23 amino acid sequence, producing an inactive N-terminal fragment (Y25 to R179) and a C-terminal fragment (S180 to I251) (FIG. 1A) (Goetz et al., "Molecular Insights into the Klotho-dependent, Endocrine Mode of Action of Fibroblast Growth Factor 19 Subfamily Members," *Mol Cell Biol* 27(9):3417-3428 (2007)). FGF receptor (FGFR) 1 is the principal mediator of the phosphaturic action of FGF23 (Liu et al., "FGFR3 and FGFR4 do not Mediate Renal Effects of FGF23," *J Am Soc Nephrol* 19(12): 2342-2350 (2008); Gattineni et al., "FGF23 Decreases Renal NaPi-2a and NaPi-2c Expression and Induces Hypophosphatemia in vivo Predominantly via FGF Receptor 1," *Am J Physiol* 297(2):F282-F291 (2009)). In addition, Klotho, a protein first described as an aging suppressor (Kuro-o et al., "Mutation of the Mouse Klotho Gene Leads to a Syndrome Resembling Aging," *Nature* 390(6655):45-51 (1997)), is required as a coreceptor by FGF23 in its target tissue in order to exert its phosphaturic activity (Kurosu et al., "Regulation of Fibroblast Growth Factor-23 Signaling by Klotho," *J Biol Chem* 281(10):6120-6123 (2006); Urakawa et al., "Klotho Converts Canonical FGF Receptor into a Specific Receptor for FGF23," *Nature* 444(7120):770-774 (2006)). Klotho constitutively binds the cognate FGFRs of FGF23, and the binary FGFR-Klotho complexes exhibit enhanced binding affinity for FGF23 ((Kurosu et al., "Regulation of Fibroblast Growth Factor-23 Signaling by Klotho," *J Biol Chem* 281(10):6120-6123 (2006); Urakawa et al., "Klotho Converts Canonical FGF Receptor into a Specific Receptor for FGF23," *Nature* 444(7120):770-774 (2006)). In co-immunoprecipitation studies, it was demonstrated that the mature, full-length form of FGF23 (Y25 to I251) but not the inactive N-terminal fragment of proteolytic cleavage (Y25 to R179) binds to binary FGFR-Klotho complexes (Goetz et al., "Molecular Insights into the Klotho-dependent, Endocrine Mode of Action of Fibroblast Growth Factor 19 Subfamily Members," *Mol Cell Biol* 27(9):3417-3428 (2007)).

The present invention is directed to overcoming the deficiencies in the art.

SUMMARY OF THE INVENTION

A first aspect of the present invention relates to a method of treating hypophosphatemia in a subject. This method involves selecting a subject with hypophosphatemia associated with elevated or normal FGF23 levels, and administering to the selected subject an inhibitor of FGF23-Klotho-FGF receptor complex formation under conditions effective to treat the hypophosphatemia.

A second aspect of the present invention relates to a method of screening for compounds suitable for treatment of hypophosphatemia associated with elevated or normal FGF23 levels. This method involves providing: FGF23, binary FGFR-Klotho complex, and one or more candidate compounds. The FGF23, the FGFR-Klotho complex, and the candidate compounds are combined under conditions effective for the FGF23 and the binary FGFR-Klotho complex to form a ternary complex if present by themselves. The candidate compounds, which prevent formation of the complex, are identified as being potentially suitable in treating hypophosphatemia associated with elevated or normal FGF23 levels.

The present invention also relates to a method of screening the specificity of compounds which prevent formation of the FGF23-Klotho-FGFR complex. This method involves providing FGF19, providing binary FGFR-βKlotho complex, and providing one or more candidate compounds. The FGF19, the binary FGFR-βKlotho complex, and the candidate compounds are combined under conditions effective for the FGF19 and the binary FGFR-βKlotho complex to form a ternary complex if present by themselves. Candidate compounds which do not interfere with formation of the complex are identified as being specific and potentially suitable in treating hypophosphatemia associated with elevated or normal FGF23 levels.

Fibroblast growth factor (FGF) 23 is a key hormone and regulator of phosphate homeostasis, which inhibits renal phosphate reabsorption by activating FGF receptor (FGFR) 1c in a Klotho-dependent fashion. The present invention shows that proteolytic cleavage at the RXXR motif down-regulates FGF23's activity by a dual mechanism: by removing the binding site for the binary FGFR-Klotho complex that resides in the C-terminal region of FGF23, and by generating an endogenous FGF23 inhibitor. The soluble ectodomains of FGFR1c and Klotho are sufficient to form a ternary complex with FGF23 in vitro. The C-terminal tail of FGF23 mediates binding of FGF23 to a de novo site generated at the composite FGFR1c-Klotho interface. Consistent with this finding, the isolated 72-residue-long C-terminal tail of FGF23—the C-terminal fragment of proteolytic cleavage at the RXXR motif—impairs FGF23 signaling by competing with full-length ligand for binding to the binary FGFR-Klotho complex. Injection of the FGF23 C-terminal tail peptide into healthy rats inhibits renal phosphate excretion and induces hyperphosphatemia. In a mouse model of renal phosphate wasting attributable to high FGF23, the FGF23 C-terminal tail peptide reduces phosphate excretion leading to an increase in serum phosphate concentration. It is proposed that the proteolytic C-terminal fragment of FGF23 is an endogenous inhibitor of FGF23 and that peptides derived from the C-terminal tail of FGF23, or peptidomimetics and small molecule organomimetics of the C-terminal tail can be used as novel therapeutics to treat hypophosphatemia where FGF23 is not down-regulated as a compensatory mechanism.

Applicants have determined that the 72-amino acid C-terminal tail of FGF23 mediates binding of FGF23 to the binary FGFR-Klotho complex and, indeed, this region harbors the FGF23-binding site for the binary FGFR-Klotho complex. Based on this finding, the ability of the C-terminal region of FGF23 to antagonize FGF23 binding to FGFR-Klotho and its phosphaturic action is evaluated. It is shown that peptides derived from this region are able to competitively displace full-length FGF23 from its ternary complex with Klotho and FGFR, and inhibit FGF23 signaling. It is further shown that these peptides are able to antagonize FGF23's phosphaturic activity in vivo, both in healthy rats and in a mouse model of phosphate wasting disorders. Based on these data, it is believed that peptides derived from the C-terminal tail of FGF23, or peptidomimetics and small molecule organomimetics of the C-terminal tail can be used as novel therapeutics to treat patients with hypophosphatemia where FGF23 is not down-regulated as a compensatory mechanism.

BRIEF DESCRIPTION OF THE DRAWINGS

FIG. 1A shows the FGF23 proteins and peptides used in this study. Amino acid boundaries of each protein/peptide are labeled with residue letter and number. The FGF23 core region is shaded grey, and the position of the proteolytic cleavage site RXXR (SEQ ID NO: 1) is indicated, where "XX" is defined as "HT", corresponding to positions 177 and 178 of SEQ ID NO: 3, respectively, of the FGF23 amino acid sequence. FIG. 1B shows a size-exclusion chromatogram of the 1:1 FGFR1c-Klotho complex. Arrows indicate the retention times of molecular size standards and the void volume ($V_V$). Proteins of column peak fractions were resolved on 14% SDS-polyacrylamide gels and stained with Coomassie Blue. FIG. 1C shows a size-exclusion chromatogram of the ternary FGF23$^{28-251}$-FGFR1c-Klotho complex. Arrows indicate the retention times of molecular size standards and the void volume ($V_V$). Proteins of column peak fractions were resolved on 14% SDS-polyacrylamide gels and stained with Coomassie Blue. FIG. 1D shows a representative surface plasmon resonance (SPR) sensorgram of FGFR1c binding to Klotho, and fitted saturation binding curve. Klotho ectodomain was immobilized on a biosensor chip, and increasing concentrations of FGFR1c ectodomain were passed over the chip. The dissociation constant ($K_D$) was calculated from the saturation binding curve. FIG. 1E shows a representative SPR sensorgram illustrating binding of FGF23$^{28-251}$ to the binary FGFR1c-Klotho complex. FGF23$^{28-251}$ was immobilized on a biosensor chip, and increasing concentrations of FGFR1c-Klotho complex were passed over the chip. FIG. 1F shows a representative SPR sensorgram of FGF23 binding to Klotho alone. FGF23$^{28-251}$ was immobilized on a biosensor chip, and increasing concentrations of Klotho ectodomain were passed over the chip. FIG. 1G shows a representative SPR sensorgram of FGF23 binding to FGFR1c alone. FGF23$^{28-251}$ was immobilized on a biosensor chip, and increasing concentrations of FGFR1c ectodomain were passed over the chip.

FIGS. 2A-D show the FGF23 C-terminal tail mediates binding of FGF23 to the binary FGFR-Klotho complex. FIG. 2A shows a representative SPR sensorgram illustrating binding of FGF23$^{180-251}$ to the binary FGFR1c-Klotho complex. FGF23$^{180-251}$ was immobilized on a biosensor chip, and increasing concentrations of FGFR1c-Klotho complex were passed over the chip. FIG. 2B shows a size-exclusion chromatogram of the mixture of the 1:1 FGFR1c-Klotho complex with FGF23$^{180-251}$. Arrows indicate the retention times of molecular size standards and the void volume ($V_V$). Proteins of column peak fractions were resolved on 14% SDS-polyacrylamide gels and stained with Coomassie Blue. FIG. 2C shows a size-exclusion chromatogram of the mixture of the 1:1 FGFR1c-Klotho complex with FGF23$^{28-179}$. Arrows indicate the retention times of molecular size standards and the void volume ($V_V$). Proteins of column peak fractions were resolved on 14% SDS-polyacrylamide gels and stained with Coomassie Blue. FIG. 2D shows analysis of FGF23 protein/peptide binding to FGFR-Klotho complex by pull-down assay. Lysate of HEK293 cells stably expressing Klotho was incubated with FGF23 proteins, or protein sample buffer (control). Binary complexes of endogenous FGFR and Klotho were isolated from cell lysate by immunoprecipitation (IP) and analyzed for bound FGF23 protein/peptide.

FIGS. 3A-H show that the isolated FGF23 C-terminal tail peptide competes with FGF23 for binding to the binary FGFR-Klotho complex. FIG. 3A shows a representative SPR sensorgram illustrating inhibition by FGF23$^{180-251}$ of FGFR1c-Klotho binding to FGF23$^{28-251}$ immobilized on a biosensor chip. Increasing concentrations of FGF23$^{180-251}$ were mixed with a fixed concentration of FGFR1c-Klotho complex and the mixtures were passed over a FGF23 chip. FIG. 3B shows a representative SPR sensorgram illustrating inhibition by FGF23$^{180-205}$ of FGFR1c-Klotho binding to FGF23$^{28-251}$ immobilized on a biosensor chip. Increasing concentrations of FGF23$^{180-205}$ were mixed with a fixed concentration of FGFR1c-Klotho complex and the mixtures were passed over a FGF23 chip. The sequences of FGF23$^{180-251}$, FGF23$^{180-205}$, and FGF23$^{28-251}$ are listed in Table 1. FIG. 3C shows a representative SPR sensorgram illustrating inhibition by FGF23$^{28-251}$ of FGFR1c-Klotho binding to FGF23$^{28-251}$ immobilized on a biosensor chip. Increasing concentrations of FGF23$^{28-251}$ were mixed with a fixed concentration of FGFR1c-Klotho complex and the mixtures were passed over a FGF23 chip. FIG. 3D shows dose-response curves for inhibition by FGF23$^{180-251}$ (filled circles), FGF23$^{180-205}$ (open circles), or FGF23$^{28-251}$ (filled triangles) of FGFR1c-Klotho binding to FGF23 immobilized on a biosensor chip (see also SPR sensorgrams shown in FIGS. 3A-C). For each dose-response curve, averaged data from two to three SPR experiments are presented. Inhibition of binding by the FGF23 C-terminal peptides and full-length FGF23, respectively, is expressed as percent of the binding response obtained for the binary FGFR1c-Klotho complex alone, and plotted as a function of the concentration of FGF23 protein/peptide. Note that the dose-response curves of the C-terminal FGF23 peptides are shifted to the right by about 3-fold and 6-fold, respectively, compared to the dose-response curve of full-length FGF23. Error bars denote SD. FIG. 3E shows a representative SPR sensorgram illustrating inhibition by FGF23$^{28-251}$ of FGFR1c-Klotho binding to FGF23$^{180-251}$ immobilized on a biosensor chip. Increasing concentrations of FGF23$^{28-251}$ were mixed with a fixed concentration of FGFR1c-Klotho complex and the mixtures were passed over a FGF23$^{180-251}$ chip. FIG. 3F shows a representative SPR sensorgram illustrating inhibition by FGF23$^{180-251}$ of FGFR1c-Klotho binding to FGF23$^{180-251}$ immobilized on a biosensor chip. Increasing concentrations of FGF23$^{180-251}$ were mixed with a fixed concentration of FGFR1c-Klotho complex and the mixtures were passed over a FGF23$^{180-251}$ chip. FIG. 3G shows a representative SPR sensorgram illustrating no inhibition by FGF21$^{168-209}$ of FGFR1c-Klotho binding to FGF23$^{28-251}$ immobilized on a biosensor chip. FGF21$^{168-209}$ and FGFR1c-Klotho complex were mixed at molar ratios of 6:1 and 10:1, and the mixtures were passed over a FGF23 chip. FIG. 3H shows inhibition by FGF23$^{180-251}$ of FGFR-Klotho binding to FGF23$^{28-251}$ using a co-immunoprecipitation based competition assay. Cognate FGFRs of FGF23 were co-immunoprecipitated with Klotho from lysates of a HEK293 cell line stably expressing Klotho (IP) Immunoprecipitated binary FGFR-Klotho complexes were incubated with either FGF23$^{180-251}$ or FGF23$^{28-251}$ alone, or with mixtures of FGF23$^{28-251}$ with increasing FGF23$^{180-251}$, and subsequently analyzed for bound FGF23 protein(s). A 76-fold molar excess of FGF23$^{180-251}$ completely blocked binding of FGF23$^{28-251}$ to the FGFR-Klotho complex. Consistent with the data shown in FIGS. 2A-D, FGF23$^{180-251}$ alone co-precipitated with each of the three binary FGFR-Klotho complexes (first lane of each immunoblot). The sequences of FGF23$^{180-251}$ FGF23$^{180-205}$, and FGF23$^{28-251}$ are listed in Table 1.

FIGS. 4A-D show that the FGF23 C-terminal tail peptide does not interfere with binary complex formation between βKlotho and FGF19/FGF21, nor does it interfere with ternary complex formation between βKlotho, FGFR, and FGF19/FGF21. FIG. 4A shows a representative SPR sensorgram illustrating no inhibition by FGF23$^{180-251}$ of βKlotho binding to FGF19$^{23-216}$ immobilized on a biosensor chip. FGF23$^{180-251}$ and βKlotho were mixed at a molar ratio of 2:1, and the mixture was passed over a FGF19 chip. FIG. 4B shows a representative SPR sensorgram illustrating no inhibition by FGF23$^{180-251}$ of βKlotho binding to FGF21$^{29-209}$ immobilized on a biosensor chip. FGF23$^{180-251}$ and βKlotho were mixed at a molar ratio of 2:1, and the mixture was passed over a FGF21 chip. FIG. 4C shows a representative SPR sensorgram illustrating no inhibition by FGF23$^{180-251}$ of FGFR1c-βKlotho binding to FGF19$^{23-216}$ immobilized on a biosensor chip. FGF23$^{180-251}$ and FGFR1c-βKlotho complex were mixed at a molar ratio of 10:1, and the mixture was passed over a FGF19 chip. FIG. 4D shows a representative SPR sensorgram illustrating no inhibition by FGF23$^{180-251}$ of FGFR1c-βKlotho binding to FGF21$^{29-209}$ immobilized on a biosensor chip. FGF23$^{180-251}$ and FGFR1c-βKlotho complex were mixed at a molar ratio of 10:1, and the mixture was passed over a FGF21 chip.

FIG. 5A shows that FGF23$^{28-200}$ induces tyrosine phosphorylation of FRS2α and downstream activation of MAP kinase cascade. Shown is an immunoblot analysis for phosphorylation of FRS2α (pFRS2α) and 44/42 MAP kinase (p44/42 MAPK) in a CHO Klotho cell line, which had been stimulated with either FGF23$^{28-251}$ or FGF23$^{28-200}$. Numbers above the lanes give the amounts of protein added in nM. To control for equal sample loading, the protein blots were probed with antibodies to non-phosphorylated$^{44/42}$ MAP kinase (44/42 MAPK) and Klotho. FIG. 5B shows that FGF23$^{28-200}$ exhibits phosphaturic activity. FGF23$^{28-251}$ and FGF23$^{28-200}$ were injected IP into C57BL/6 mice, and serum levels of phosphate (serum $P_i$) were measured before and after FGF23 protein injection. Bars and error bars denote mean±SE. An asterisk indicates P<0.05 by ANOVA. FIG. 5C shows that FGF23$^{180-205}$—the minimal binding epitope for the FGFR-Klotho complex—competes with FGF23 for binding to FGFR-Klotho. Cognate FGFRs of FGF23 were co-immunoprecipitated with Klotho from lysates of a HEK293 cell line stably expressing Klotho (IP). Immunoprecipitated binary FGFR-Klotho complexes were incubated with either FGF23$^{28-251}$ alone or mixtures of FGF23$^{28-251}$ with increasing FGF23$^{180-205}$, and subsequently analyzed for bound FGF23 protein(s). The FGF23$^{180-205}$ peptide inhibited co-precipitation of FGF23$^{28-251}$ with each of the three binary FGFR-Klotho complexes in a dose-dependent fashion, albeit with over 100-fold reduced potency compared to the FGF23$^{180-251}$ peptide (FIG. 3H). The sequences of FGF23$^{180-251}$, FGF23$^{180-205}$, and FGF23$^{28-251}$ are listed in Table 1.

FIG. 6A shows that FGF23$^{180-251}$ inhibits tyrosine phosphorylation of FRS2α and downstream activation of MAP kinase cascade induced by FGF23$^{28-251}$. Shown is an immunoblot analysis for phosphorylation of FRS2α (pFRS2α) and 44/42 MAP kinase (p44/42 MAPK) in a HEK293 Klotho cell line, which had been stimulated with FGF proteins/peptide as denoted in the figure. Numbers above the lanes give the amounts of protein/peptide added in nM. To control for equal sample loading, the protein blots were probed with an antibody to Klotho. FIG. 6B shows that FGF23$^{180-205}$ inhibits tyrosine phosphorylation of FRS2α and downstream activation of MAP kinase cascade induced by FGF23$^{28-251}$. Shown is an immunoblot analysis for phosphorylation of FRS2α (pFRS2α) and 44/42 MAP kinase (p44/42 MAPK) in a HEK293 Klotho cell line, which had been stimulated with either FGF23$^{180-205}$ alone or mixtures of FGF23$^{28-251}$ with increasing FGF23$^{180-205}$. Numbers above the lanes give the amounts of peptide added in µM. To control for equal sample loading, the protein blots were probed with an antibody to non-phosphorylated 44/42 MAP kinase (44/42 MAPK). FIG. 6C shows that FGF23$^{180-251}$ fails to inhibit tyrosine phosphorylation of FRS2α and downstream activation of MAP kinase cascade induced by FGF2. Shown is an immunoblot analysis for phosphorylation of FRS2α (pFRS2α) and 44/42 MAP kinase (p44/42 MAPK) in a HEK293 Klotho cell line, which had been stimulated with either FGF2 alone or mixtures of FGF2 with increasing FGF23$^{180-251}$. Numbers above the lanes give the amounts of peptide added in nM. To control for equal sample loading, the protein blots were probed with an antibody to Klotho. The sequences of FGF23$^{180-251}$, FGF23$^{180-205}$, and FGF23$^{28-251}$ are listed in Table 1.

FIG. 9A shows representative images of cryosections of renal tissue processed for NaP$_i$-2A immunostaining and β-actin staining. FIGS. 9B-C show NaP$_i$-2A (FIG. 9B) and NaP$_i$-2C (FIG. 9C) protein abundance in renal cortex tissue (cortex) and isolated brush border membrane vesicles (BBMV). Equal amounts of protein were separated by SDS-PAGE and probed for either NaP$_i$-2A or NaP$_i$-2C, and β-actin by immunoblot. Representative protein blots with tissues from 6 rats are shown in the upper panels of each figure part. Summarized data of renal tissue samples from 12 rats are presented in the bottom panels. Bars and error bars are mean+SE. An asterisk denotes P<0.05 by ANOVA.

DETAILED DESCRIPTION OF THE INVENTION

Figure 1A:
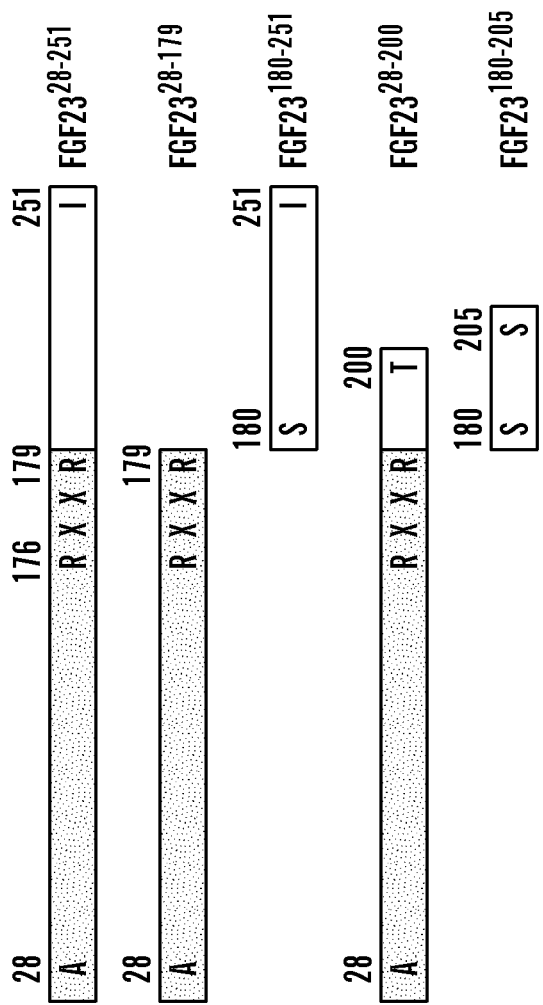
FIGS. 1A-G show that FGF23 binds to the preformed binary complex of the ectodomains of FGFR and Klotho.

A first aspect of the present invention relates to a method of treating hypophosphatemia in a subject. This method involves selecting a subject with hypophosphatemia associated with elevated or normal FGF23 levels and administering to the selected subject an inhibitor of FGF23-Klotho-FGF receptor complex formation under conditions effective to treat the hypophosphatemia.

As described by Goetz et al. (Goetz et al., "Molecular Insights into the Klotho-Dependent, Endocrine Mode of Action of Fibroblast Growth Factor 19 Subfamily Members," *Mol Cell Biol* 3417-3428 (2007), which is hereby incorporated by reference in its entirety), the mammalian fibroblast growth factor (FGF) family comprises 18 polypeptides (FGF1 to FGF10 and FGF16 to FGF23), which participate in a myriad of biological processes during embryo genesis, including but not limited to gastrulation, body plan formation, somitogenesis, and morphogenesis of essentially every tissue/organ such as limb, lung, brain, and kidney (Bottcher et al., "Fibroblast Growth Factor Signaling During Early Vertebrate Development," *Endocr Rev* 26:63-77 (2005), and Thisse et al., "Functions and Regulations of Fibroblast Growth Factor Signaling During Embryonic Development," *Dev Biol* 287:390-402 (2005), which are hereby incorporated by reference in their entirety).

FGFs execute their biological actions by binding to, dimerizing, and activating FGF receptor (FGFR) tyrosine kinases, which are encoded by four distinct genes (Fgfr1 to Fgfr4). Prototypical FGFRs consist of an extracellular domain composed of three immunoglobulin-like domains, a single-pass transmembrane domain, and an intracellular domain responsible for the tyrosine kinase activity (Mohammadi et al., "Structural Basis for Fibroblast Growth Factor Receptor Activation," *Cytokine Growth Factor Rev* 16:107-137 (2005), which is hereby incorporated by reference in its entirety).

FGF23 is a gene cloned by Itoh et al. at Kyoto University (WO 01/66596 to Itoh et al., which is hereby incorporated by reference in its entirety). FGF23 mRNA is expressed mainly in the brain, preferentially in the ventrolateral thalamic nucleus. It is also expressed in the thymus at low levels (Yamashita et al., "Identification of a Novel Fibroblast Growth Factor, FGF-23, Preferentially Expressed in the Ventrolateral Thalamic Nucleus of the Brain," *Biochem Biophys Res Comm* 277(2):494-498 (2000), which is hereby incorporated by reference in its entirety). The tissue with the highest level of FGF23 expression is bone (osteocytes and osteoblasts), where it is highly expressed during phases of active bone remodeling (Riminucci et al., "FGF-23 in Fibrous Dysplasia of Bone and its Relationship to Renal Phosphate Wasting," *J Clin Invest* 112:683-692 (2003), which is hereby incorporated by reference in its entirety). Expression of FGF23 in dendritic cells has also been reported (Katoh et al., "Comparative Genomics on Mammalian Fgf6-Fgf23 Locus.," *Int J Mol Med* 16(2):355-358 (2005), which is hereby incorporated by reference in its entirety). See also Zhang et al., "Receptor Specificity of the Fibroblast Growth Factor Family," *J Biol Chem* 281(23):15694-15700; Yu et al., "Analysis of the Biochemical Mechanisms for the Endocrine Actions of Fibroblast Growth Factor-23," *Endocrinology* 146(11):4647-4656, which are hereby incorporated by reference in their entirety.

The number of principal FGFRs is increased from four to seven due to a major tissue-specific alternative splicing event in the second half of the immunoglobulin-like domain 3 of FGFR1 to FGFR3, which creates epithelial lineage-specific b and mesenchymal lineage-specific c isoforms (Mohammadi et al., "Structural Basis for Fibroblast Growth Factor Receptor Activation," *Cytokine Growth Factor Rev* 16:107-137 (2005) and Ornitz et al., "Fibroblast Growth Factors," *Genome Biol* 2(3):reviews3005.1-reviews3005.12 (2001), which are hereby incorporated by reference in their entirety). Generally, the receptor-binding specificity of FGFs is divided along this major alternative splicing of receptors whereby FGFRb-interacting FGFs are produced by epithelial cells (Ornitz et al., "Fibroblast Growth Factors," *Genome Biol* 2(3):reviews3005.1-reviews3005.12 (2001), which is hereby incorporated by reference in its entirety). These reciprocal expression patterns of FGFs and FGFRs result in the establishment of a paracrine epithelial-mesenchymal signaling which is essential for proper organogenesis and patterning during development as well as tissue homeostasis in the adult organism.

Based on phylogeny and sequence identity, FGFs are grouped into seven subfamilies (Ornitz et al., "Fibroblast Growth Factors," *Genome Biol* 2(3):reviews3005.1-reviews3005.12 (2001), which is hereby incorporated by reference in its entirety). The FGF core homology domain (approximately 120 amino acids long) is flanked by N- and C-terminal sequences that are highly variable in both length and primary sequence, particularly among different FGF subfamilies. The core region of FGF19 shares the highest sequence identity with FGF21 (38%) and FGF23 (36%), and therefore, these ligands are considered to form a subfamily.

The nucleic acid and amino acid sequences for homo sapiens (human) FGF23 may be found using the following reference sequence ID number on GenBank, NM_020638. The human FGF23 gene coding sequence (1-251) has a nucleotide sequence of SEQ ID NO: 2 as follows:

```
cggcaaaaag gagggaatcc agtctaggat cctcacacca gctacttgca agggagaagg aaaaggccag taaggcctgg gccaggagag tcccgacagg agtgtcaggt ttcaatctca gcaccagcca ctcagagcag ggcacgatgt tgggggcccg cctcaggctc tgggtctgtg ccttgtgcag cgtctgcagc atgagcgtcc tcagagccta tcccaatgcc tccccactgc tcggctccag ctggggtggc ctgatccacc tgtacacagc cacagccagg aacagctacc acctgcagat ccacaagaat ggccatgtgg atggcgcacc ccatcagacc atctacagtg
```

```
ccctgatgat cagatcagag gatgctggct ttgtggtgat tacaggtgtg atgagcagaa
gatacctctg catggatttc agaggcaaca tttttggatc acactatttc gacccggaga
actgcaggtt ccaacaccag acgctggaaa acgggtacga cgtctaccac tctcctcagt
atcacttcct ggtcagtctg ggccgggcga agagagcctt cctgccaggc atgaacccac
ccccgtactc ccagttcctg tcccggagga acagatccc cctaattcac ttcaacaccc
ccataccacg gcggcacacc cggagcgccg aggacgactc ggagcgggac cccctgaacg
tgctgaagcc ccgggcccgg atgacccgg ccccggcctc ctgttcacag gagctcccga
gcgccgagga caacagcccg atggccagtg acccattagg ggtggtcagg ggcggtcgag
tgaacacgca cgctggggga acgggcccgg aaggctgccg ccccttcgcc aagttcatct
agggtcgctg gaagggcacc ctctttaacc catccctcag caaacgcagc tcttcccaag
gaccaggtcc cttgacgttc cgaggatggg aaaggtgaca ggggcatgta tggaatttgc
tgcttctctg gggtcccttc cacaggaggt cctgtgagaa ccaacctttg aggcccaagt
catgggtttt caccgcctte ctcactccat atagaacacc tttcccaata ggaaacccca
acaggtaaac tagaaatttc cccttcatga aggtagagag aaggggtctc tcccaacata
tttctcttcc ttgtgcctct cctctttatc acttttaagc ataaaaaaaa aaaaaaaaa
aaaaaaaaaa aaaagcagtg ggttcctgag ctcaagactt tgaaggtgta gggaagagga
aatcggagat cccagaagct tctccactgc cctatgcatt tatgttagat gccccgatcc
cactggcatt tgagtgtgca accttgaca ttaacagctg aatggggcaa gttgatgaaa
acactacttt caagccttcg ttcttccttg agcatctctg gggaagagct gtcaaaagac
tggtggtagg ctggtgaaaa cttgacagct agacttgatg cttgctgaaa tgaggcagga
atcataatag aaaactcagc ctccctacag ggtgagcacc ttctgtctcg ctgtctccct
ctgtgcagcc acagccagag ggcccagaat ggccccactc tgttcccaag cagttcatga
tacagcctca cctttggcc ccatctctgg ttttgaaaa tttggtctaa ggataaaata
gcttttacac tggctcacga aaatctgccc tgctagaatt tgcttttcaa aatggaaata
aattccaact ctcctaagag gcatttaatt aaggctctac ttccaggttg agtaggaatc
cattctgaac aaaactacaa aatgtgactg ggaaggggc tttgagagac tgggactgct
ctgggttagg ttttctgtgg actgaaaaat cgtgtccttt tctctaaatg aagtggcatc
aaggactcag ggggaaagaa atcaggggac atgttataga agttatgaaa agacaaccac
atggtcaggc tcttgtctgt ggtctctagg gctctgcagc agcagtggct cttcgattag
ttaaaactct cctaggctga cacatctggg tctcaatccc cttggaaatt cttggtgcat
taaatgaagc cttaccccat tactgcggtt cttcctgtaa gggggctcca ttttcctccc
tctcttaaa tgaccaccta aaggacagta tattaacaag caaagtcgat tcaacaacag
cttcttccca gtcactttt tttttctcac tgccatcaca tactaacctt atactttgat
ctattctttt tggttatgag agaaatgttg ggcaactgtt tttacctgat ggttttaagc
tgaacttgaa ggactggttc ctattctgaa acagtaaaac tatgtataat agtatatagc
catgcatggc aaatattta atatttctgt tttcatttcc tgttggaaat attatcctgc
ataatagcta ttggaggctc ctcagtgaaa gatcccaaaa ggattttggt ggaaaactag
ttgtaatctc acaaactcaa cactaccatc aggggttttc tttatggcaa agccaaaata
gctcctacaa tttcttatat ccctcgtcat gtggcagtat ttatttattt atttggaagt
ttgcctatcc ttctatattt atagatattt ataaaaatgt aaccccttt tcctttcttc
tgtttaaaat aaaaataaaa tttatctcag cttctgttag cttatcctct ttgtagtact
```

-continued

```
acttaaaagc atgtcggaat ataagaataa aaaggattat gggaggggaa cattagggaa atccagagaa ggcaaaattg aaaaaaagat tttagaattt taaaattttc aaagatttct tccattcata aggagactca atgattttaa ttgatctaga cagaattatt taagttttat caatattgga tttctggt
```

As described above, reference sequence ID number on Genbank NM_020638 shows the nucleotide sequence for human FGF23 (i.e. SEQ ID NO:2) encodes a protein with the amino acid sequence of SEQ ID NO: 3 as follows:

```
mlgarlrlwvcalcsvcsmsvlraypnaspllgsswgglihlytatarnsyhlqihknghvdgaphqti ysalmirsedagfvvitgvmsrrylcmdfrgnifgshyfdpencrfqhqtlengydvyhspqyhflvsl grakraflpgmnpppysqflsrrneiplihfntpiprrhtrsaeddserdplnvlkprarmtpapascs qelpsaednspmasdplgvvrggrvnthaggtgpegcrpfakfi
```

Furthermore, Luethy et al. have cloned the FGF23 gene to produce a transgenic mouse that expresses the gene, and analyzed the phenotype of the mouse (WO 01/61007 to Luethy et al., which is hereby incorporated by reference in its entirety). See also U.S. Patent Application Publication No. 20050106755 to Zahradnik et al., which is hereby incorporated by reference in its entirety).

The nucleic acid and amino acid sequences for the Mus musculus (mouse) FGF23 may be found at GenBank, NM_022657. The mouse FGF23 gene coding sequence has a nucleotide sequence SEQ ID NO: 4 as follows:

```
gaatctagcc caggatcccc acctcagttc tcagcttctt cctaggaaga agagaaaggc cagcaagggc ccagcctgtc tgggagtgtc agatttcaaa ctcagcatta gccactcagt gctgtgcaat gctagggacc tgccttagac tcctggtggg cgtgctctgc actgtctgca gcttgggcac tgctagagcc tatccggaca cttccccatt gcttggctcc aactggggaa gcctgaccca cctgtacacg gctacagcca ggaccagcta tcacctacag atccataggg atggtcatgt agatggcacc cccatcaga ccatctacag tgccctgatg attacatcag aggacgccgg ctctgtggtg ataacaggag ccatgactcg aaggttcctt tgtatggatc tccacggcaa cattttggga tcgcttcact tcagcccaga gaattgcaag ttccgccagt ggacgctgga gaatggctat gacgtctact tgtcgcagaa gcatcactac ctggtgagcc tgggccgcgc caagcgcatc ttccagccgg gcaccaaccc gccgccttc tcccagttcc tggctcgcag gaacgaggtc ccgctgctgc atttctacac tgttcgccca cggcgccaca cgcgcagcgc cgaggaccca ccggagcgcg acccactgaa cgtgctcaag ccgcggcccc gcgccacgcc tgtgcctgta tcctgctctc gcgagctgcc gagcgcagag gaaggtggcc ccgcagccag cgatcctctg ggggtgctgc gcagaggccg tggagatgct cgcgggggcg cgggaggcgc ggataggtgt cgccccttc ccaggttcgt ctaggtcccc aggccaggct gcgtccgcct ccatcctcca gtcggttcag cccacgtaga ggaaggacta gggtacctcg aggatgtctg cttctctccc ttccctatgg gcctgagagt cacctgcgag gttccagcca ggcaccgcta ttcagaatta agagccaacg gtgggaggct ggagaggtgg cgcagacagt tctcagcacc cacaaatacc tgtaattcta gctccagggg aatctgtact cacacacaca cacatccaca cacacacaca cacacataca tgtaatttta aatgttaatc tgatttaaag acccccaacag gtaaactaga cacgaagctc ttttattt attttactaa caggtaaacc agacacttgg cctttattag ccgggtctct tgcctagcat tttaatcgat cagttagcac
```

```
gaggaaagag ttcacgcctt gaacacaggg aagaggccat ctctgcagct tctagttact attctgggat tcacgggtgt ttgagtttga gcaccttgac cttaatgtct tcactaggca agtcgaagaa agacgcgcat ttcttctctt tgggaagagc tttggattgg cgggaggctg acaaggacac ctaaaccgaa cacatttcag agttcagcct ccctgaggaa tgattcgcca atgattctgt gataggacca gtcagtagct tttgaatttg ccctggctca gcaaagtcta ccttgctagg gtgttttgca aaatgcaaac gctcgaactc tctctaaaga ggcattttta gtgaaagcct ccgctagcag gttgacttgt aatatattct aagcgaatgt gcccggggtg ggggtggagg tggggtgggg gagaagggtc cttgagacct cggattgttc taggttaggg tttctgtgaa gagg
```

As described above, reference sequence ID number on Genbank NM_022657 shows the nucleotide sequence for mouse FGF23 (i.e. SEQ ID NO: 4) encodes a protein with the amino acid sequence of SEQ ID NO: 5 as follows:

```
mlgtclrllvgvlctvcslgtaraypdtspllgsnwgslthlytatartsyhlqihrdghydgtphqti ysalmitsedagsvvitgamtrrflomdlhgnifgslhfspenckfrqwtlengydvylsqkhhylvsl grakrifqpgtnpppfsqflarrnevpllhfytvrprrhtrsaedpperdpinylkprpratpvpvscs relpsaeeggpaasdplgylrrgrgdarggaggadrcrpfprfv
```

Kurosu et al. and Urakawa et al. have identified Klotho as an obligate co-receptor of FGF23 (Kurosu et al., "Regulation of Fibroblast Growth Factor-23 Signaling by Klotho," *J Biol Chem* 281(10):6120-6123 (2006); Urakawa et al., "Klotho Converts Canonical FGF Receptor Into a Specific Receptor for FGF23," *Nature* 444:770-774 (2006), which are hereby incorporated by reference in their entirety).

The nucleic acid and amino acid sequences for the human Klotho (i.e. SEQ ID NO: 6) gene may be found at GenBank, NM_004795. The human Klotho gene coding sequence has a nucleotide sequence of SEQ ID NO: 6 as follows:

```
cgcgcagcat gcccgccagc gcccgccgc gccgcccgcg gccgccgccg ccgtcgctgt cgctgctgct ggtgctgctg ggcctgggcg gccgccgcct gcgtgcggag ccgggcgacg gcgcgcagac ctgggcccgt ttctcgcggc ctcctgcccc cgaggccgcg ggcctcttcc agggcacctt ccccgacggc ttcctctggg ccgtgggcag cgccgcctac cagaccgagg gcggctggca gcagcacggc aagggtgcgt ccatctggga tacgttcacc caccaccccc tggcaccccc gggagactcc cggaacgcca gtctgccgtt gggcgccccg tcgccgctgc agcccgccac cggggacgta gccagcgaca gctacaacaa cgtcttccgc gacacggagg cgctgcgcga gctcggggtc actcactacc gcttctccat ctcgtgggcg cgagtgctcc ccaatggcag cgccgggcgtc cccaaccgcg aggggctgcg ctactaccgg cgcctgctgg agcggctgcg ggagctgggc gtgcagcccg tggtcacccT gtaccactgg gacctgcccc agcgcctgca ggacgcctac ggcggctggg ccaaccgcgc cctggccgac cacttcaggg attacgcgga gctctgcttc cgccacttcg gcggtcaggt caagtactgg atcaccatcg acaacccta cgtggtggcc tggcacggct acgccaccgg gcgcctggcc cccggcatcc ggggcagccc gcggctcggg tacctggtgg cgcacaacct cctcctggct catgccaaag tctggcatct ctacaatact tctttccgtc ccactcaggg aggtcaggtg tccattgccc taagctctca ctggatcaat cctcgaagaa tgaccgacca cagcatcaaa gaatgtcaaa aatctctgga ctttgtacta ggttggtttg ccaaacccgt atttattgat ggtgactatc
```

-continued

```
ccgagagcat gaagaataac ctttcatcta ttctgcctga ttttactgaa tctgagaaaa agttcatcaa aggaactgct gactttttg ctctttgctt tggacccacc ttgagttttc aacttttgga ccctcacatg aagttccgcc aattggaatc tcccaacctg aggcaactgc tttcctggat tgaccttgaa tttaaccatc ctcaaatatt tattgtggaa aatggctggt ttgtctcagg gaccaccaag agagatgatg ccaaatatat gtattacctc aaaaagttca tcatggaaac cttaaaagcc atcaagctgg atggggtgga tgtcatcggg tataccgcat ggtccctcat ggatggtttc gagtggcaca gaggttacag catcaggcgt ggactcttct atgttgactt tctaagccag acaagatgt tgttgccaaa gtcttcagcc ttgttctacc aaaagctgat agagaaaaat ggcttcctc ctttacctga aaatcagccc ctagaaggga catttccctg tgactttgct tggggagttg ttgacaacta cattcaagta gataccactc tgtctcagtt taccgacctg aatgtttacc tgtgggatgt ccaccacagt aaaaggctta ttaaagtgga tggggttgtg accaagaaga ggaaatccta ctgtgttgac tttgctgcca tccagcccca gatcgcttta ctccaggaaa tgcacgttac acattttcgc ttctccctgg actgggccct gattctccct ctgggtaacc agtcccaggt gaaccacacc atcctgcagt actatcgcta catggccagc gagcttgtcc gtgtcaacat caccccagtg gtggccctgt ggcagcctat ggccccgaac caaggactgc cgcgcctcct ggccaggcag ggcgcctggg agaacccta cactgccctg cctttgcag agtatgcccg actgtgcttt caagagctcg gccatcacgt caagctttgg ataacgatga atgagccgta tacaaggaat atgacataca gtgctggcca caaccttctg aaggcccatg ccctggcttg gcatgtgtac aatgaaaagt ttaggcatgc tcagaatggg aaaatatcca tagccttgca ggctgattgg atagaacctg cctgccctt ctcccaaaag gacaaagagg tggctgagag agttttggaa tttgacattg gctggctggc tgagcccatt ttcggctctg gagattatcc atgggtgatg agggactggc tgaaccaaag aaacaatttt cttcttcctt atttcactga agatgaaaaa aagctaatcc agggtacctt tgacttttg gctttaagcc attataccac catccttgta gactcagaaa aagaagatcc aataaaatac aatgattacc tagaagtgca agaaatgacc gacatcacgt ggctcaactc ccccagtcag gtggcggtag tgccctgggg gttgcgcaaa gtgctgaact ggctgaagtt caagtacgga gacctcccca tgtacataat atccaatgga atcgatgacg ggctgcatgc tgaggacgac cagctgaggg tgtattatat gcagaattac ataaacgaag ctctcaaagc ccacatactg gatggtatca atctttgcgg atactttgct tattcgttta acgaccgcac agctccgagg tttggcctct atcgttatgc tgcagatcag tttgagccca aggcatccat gaaacattac aggaaaatta ttgacagcaa tggtttcccg ggcccagaaa ctctggaaag attttgtcca gaagaattca ccgtgtgtac tgagtgcagt tttttcaca cccgaaagtc tttactggct ttcatagctt ttctattttt tgcttctatt atttctctct cccttatatt ttactactcg aagaaaggca gaagaagtta caaatagttc tgaacatttt tctattcatt cattttgaaa taattatgca gacacatcag ctgttaacca tttgcacctc taagtgttgt gaaactgtaa atttcataca tttgacttct agaaaacatt tttgtggctt atgacagagg ttttgaaatg ggcataggtg atcgtaaaat attgaataat gcgaatagtg cctgaatttg ttctcttttt gggtgattaa aaaactgaca ggcactataa tttctgtaac acactaacaa aagcatgaaa ataggaacc acaccaatgc aacatttgtg cagaaatttg aatgacaaga ttaggaatat ttccttctgc acccacttct aaatttaatg ttttctgga agtagtaatt gcaagagttc gaatagaaag ttatgtacca agtaaccatt tctcagctgc
```

-continued

```
cataataatg cctagtggct tccctctgt caaatctagt ttcctatgga aaagaagatg gcagatacag gagagacgac agagggtcct aggctggaat gttccttcg aaagcaatgc ttctatcaaa tactagtatt aatttatgta tctggttaat gacatacttg gagagcaaat tatgaaatg tgtatttat atgatttttg aggtcctgtc taaaccctgt gtccctgagg gatctgtctc actggcatct tgttgagggc cttgcacata ggaaacttt gataagtatc tgcgaaaaa caaacatgaa tcctgtgata ttgggctctt caggaagcat aaagcaattg tgaaatacag tataccgcag tggctctagg tggaggaaag gaggaaaaag tgcttattat gtgcaacatt atgattaatc tgattataca ccatttttga gcagatcttg gaatgaatga catgaccttt ccctagagaa taaggatgaa ataatcactc attctatgaa cagtgacact actttctatt ctttagctgt actgtaattt ctttgagttg atagttttac aaattcttaa taggttcaaa agcaatctgg tctgaataac actggatttg tttctgtgat ctctgaggtc tattttatgt ttttgctgct acttctgtgg aagtagcttt gaactagttt tactttgaac tttcacgctg aaacatgcta gtgatatcta gaaagggcta attaggtctc atcctttaat gccccttaaa taagtcttgc tgattttcag acagggaagt ctctctatta cactggagct gttttataga taagtcaata ttgtatcagg caagataaac caatgtcata acaggcattg ccaacctcac tgacacaggg tcatagtgta taataatata ctgtactata taatatatca tctttagagg tatgattttt tcatgaaaga taagcttttg gtaatattca ttttaaagtg gacttattaa aattggatgc tagagaatca agtttatttt atgtatatat ttttctgatt ataagagtaa tatatgttca ttgtaaaaat ttttaaaaca cagaaactat atgcaaagaa aaaataaaaa ttatctataa tctcagaacc cagaaatagc cactattaac atttcctacg tattttattt tacatagatc atattgtata tagttagtat ctttattaat ttttattatg aaactttcct ttgtcattat tagtcttcaa aagcatgatt tttaatagtt gttgagtatt ccaccacagg aatgtatcac aacttaaccg ttcccgtttg ttagactagt ttcttattaa tgttgatgaa tgttgtttaa aaataatttt gttgctacat ttactttaat ttccttgact gtaaagagaa gtaattttgc tccttgataa agtattatat taataataaa tctgcctgca acttttgcc ttctttcata atcataaaaa aa
```

As described above, reference sequence ID number on Genbank NM_004795 shows the nucleotide sequence for human Klotho (i.e. SEQ ID NO: 6) encodes a protein with the amino acid sequence of SEQ ID NO: 7 as follows:

```
dsrnaslplgapsplqpatgdvasdsynnvfrdtealrelgvthyrfsis warvlpngsagvpnreglryyrrllerlrelgvqpvvtlyhwdlpqrlqd ayggwanraladhfrdyaelcfrhfggqvkywitidnpyvvawhgyatgr lapgirgsprlgylvahnlllahakvwhlyntsfrptqggqvsialsshw inprrmtdhsikecqksldfvlgwfakpvfidgdypesmknnlssilpdf tesekkfikgtadffalcfgptlsfqlldphmkfrqlespnlrqllswid lefnhpqifivengwfvsgttkrddakymyylkkfimetlkaikldgvdv igytawslmdgfewhrgysirrglfyvdflsqdkmllpkssalfyqklie kngfpplpenqplegtfpcdfawgvvdnyiqvdttlsqftdlnvylwdvh hskrlikvdgvvtkkrksycvdfaaiqpqiallqemhvthfrfsldwali lplgnqsqvnhtilqyyrcmaselvrvnitpvvalwqpmapnqglprlla rqgawenpytalafaeyarlcfgelghhvklwitmnepytrnmtysaghn llkahalawhvynekfrhaqngkisialqadwiepacpfsqkdkevaerv lefdigwlaepifgsgdypwvmrdwlnqrnnfllpyftedekkliqgtfd flalshyttilvdsekedpikyndylevqemtditwlnspsqvavvpwgl rkvlnwlkfkygdlpmyiisngiddglhaeddqlrvyymqnyinealkah ildginlcgyfaysfndrtaprfglyryaadqfepkasmkhyrkiidsng fpgpetlerfcpeeftvctecsffhtrksllafiaflffasiislslify yskkgrrsyk
```

The Klotho gene encodes a 130-kDa single-pass transmembrane protein with a short cytoplasmic domain (10 amino acids) and is expressed predominantly in the kidney (Matsumara et al., "Identification of the human klotho gene and its two transcripts encoding membrane and secreted klotho protein," *Biochem Biophys Res Commun* 242(3):626-630 (1998), which is hereby incorporated by reference in its entirety). In addition to the membrane-bound isoform of Klotho, alternative splicing and proteolytic cleavage give rise to two soluble isoforms of Klotho found in the circulation (Imura et al., "Secreted Klotho protein in sera and CSF: implication for post-translational cleavage in release of Klotho protein from cell membrane," *FEBS Lett* 565(1-3): 143-147 (2004); Kurosu et al., "Suppression of aging in mice by the hormone Klotho," *Science* 309(5742):1829-1833 (2005); Matsumura et al., "Identification of the human klotho gene and its two transcripts encoding membrane and secreted klotho protein," *Biochem Biophys Res Commun* 242(3):626-630 (1998); Shiraki-Iida et al., "Structure of the mouse klotho gene and its two transcripts encoding membrane and secreted protein," *FEBS Lett* 424(1-2):6-10 (1998), which are hereby incorporated by reference in their entirety). Mice carrying a loss-of-function mutation in the Klotho gene develop a syndrome resembling human aging, including shortened life span, skin atrophy, muscle atrophy, osteoporosis, arteriosclerosis, and pulmonary emphysema (Kuro-o et al., "Mutation of the Mouse Klotho Gene Leads to a Syndrome Resembling Ageing," *Nature* 390:45-51 (1997), which is hereby incorporated by reference in its entirety). Conversely, overexpression of the Klotho gene extends the life span and increases resistance to oxidative stress in mice (Kurosu et al., "Suppression of Aging in Mice by the Hormone Klotho," *Science* 309: 1829-1833 (2005), which is hereby incorporated by reference in its entirety). These observations suggest that the Klotho gene functions as an aging suppressor gene.

The nucleic acid and amino acid sequences for the human FGFR1, transcript variant 1 gene may be found at GenBank, NM_023110. The FGFR1 has the nucleotide sequence of SEQ ID NO: 8 as follows:

```
agatgcaggg gcgcaaacgc caaaggagac caggctgtag gaagagaagg gcagagcgcc ggacagctcg gcccgctccc cgtcctttgg ggccgcggct ggggaactac aaggcccagc aggcagctgc aggggcgga ggcggaggag ggaccagcgc gggtgggagt gagagagcga gccctcgcgc cccgccggcg catagcgctc ggagcgctct tgcggccaca ggcgcggcgt cctcggcggc gggcggcagc tagcgggagc cgggacgccg gtgcagccgc agcgcgcgga ggaacccggg tgtgccggga gctgggcggc cacgtccgga cgggaccgag accctcgta gcgcattgcg gcgacctcgc cttcccggc cgcgagcgcg ccgctgcttg aaaagccgcg gaacccaagg acttttctcc ggtccgagct cggggcgccc cgcagggcgc acggtacccg tgctgcagtc gggcacgccg cggcgccggg gcctccgcag ggcgatggag cccggtctgc aaggaaagtg aggcgccgcc gctgcgttct ggaggagggg ggcacaaggt ctggagaccc cgggtggcgg acgggagccc tcccccgcc ccgcctccgg ggcaccagct ccggctccat tgttcccgcc cgggctggag gcgccgagca ccgagcgccg ccgggagtcg agcgccggcc gcggagctct tgcgaccccg ccaggacccg aacagagccc gggggcggcg ggccggagcc ggggacgcgg gcacacgccc gctcgcacaa gccacggcgg actctcccga ggcggaacct ccacgccgag cgagggtcag tttgaaaagg aggatcgagc tcactgtgga gtatccatgg agatgtggag ccttgtcacc aacctctaac tgcagaactg ggatgtggag ctggaagtgc ctcctcttct gggctgtgct ggtcacagcc acactctgca ccgctaggcc gtccccgacc ttgcctgaac aagcccagcc ctggggagcc cctgtggaag tggagtcctt cctggtccac cccggtgacc tgctgcagct tcgctgtcgg ctgcgggacg atgtgcagag catcaactgg ctgcgggacg gggtgcagct ggcggaaagc aaccgcaccc gcatcacagg ggaggaggtg gaggtgcagg actccgtgcc cgcagactcc ggcctctatg cttgcgtaac cagcagcccc tcgggcagtg acaccaccta cttctccgtc aatgtttcag atgctctccc ctcctcggag gatgatgatg atgatgatga ctcctcttca gaggagaaag aaacagataa caccaaacca aaccgtatgc ccgtagctcc atattggaca tccccagaaa agatggaaaa gaaattgcat gcagtgccgg ctgccaagac agtgaagttc aaatgccctt ccagtgggac cccaaacccc acactgcgct ggttgaaaaa tgcaaagaa ttcaaacctg accacagaat tggaggctac aaggtccgtt atgccacctg gagcatcata atggactctg tggtgccctc tgacaagggc aactacacct gcattgtgga gaatgagtac ggcagcatca accacacata ccagctggat gtcgtggagc ggtcccctca ccggccccatc ctgcaagcag ggttgcccgc caacaaaaca gtggccctgg gtagcaacgt ggagttcatg tgtaaggtgt acagtgaccc gcagccgcac
```

-continued

```
atccagtggc taaagcacat cgaggtgaat gggagcaaga ttggcccaga caacctgcct tatgtccaga tcttgaagac tgctggagtt aataccaccg acaaagagat ggaggtgctt cacttaagaa atgtctcctt tgaggacgca ggggagtata cgtgcttggc gggtaactct atcggactct cccatcactc tgcatggttg accgttctgg aagccctgga agagaggccg gcagtgatga cctcgcccct gtacctggag atcatcatct attgcacagg ggccttcctc atctcctgca tggtggggtc ggtcatcgtc tacaagatga agagtggtac caagaagagt gacttccaca gccagatggc tgtgcacaag ctggccaaga gcatccctct gcgcagacag gtaacagtgt ctgctgactc cagtgcatcc atgaactctg gggttcttct ggttcggcca tcacggctct cctccagtgg gactcccatg ctagcagggg tctctgagta tgagcttccc gaagaccctc gctgggagct gcctcgggac agactggtct taggcaaacc cctgggagag ggctgctttg ggcaggtggt gttggcagag gctatcgggc tggacaagga caaacccaac cgtgtgacca aagtggctgt gaagatgttg aagtcggacg caacagagaa agacttgtca gacctgatct cagaaatgga gatgatgaag atgatcggga agcataagaa tatcatcaac ctgctggggg cctgcacgca ggatggtccc ttgtatgtca tcgtggagta tgcctccaag ggcaacctgc gggagtacct gcaggcccgg aggcccccag ggctggaata ctgctacaac cccagccaca acccagagga gcagctctcc tccaaggacc tggtgtcctg cgcctaccag gtggcccgag gcatggagta tctggcctcc aagaagtgca tacaccgaga cctggcagcc aggaatgtcc tggtgacaga ggacaatgtg atgaagatag cagactttgg cctcgcacgg gacattcacc acatcgacta ctataaaaag caaccaacg gccgactgcc tgtgaagtgg atggcacccg aggcattatt tgaccggatc tacacccacc agagtgatgt gtggtctttc ggggtgctcc tgtgggagat cttcactctg gcggctccc catacccggg tgtgcctgtg gaggaacttt tcaagctgct gaaggagggt caccgcatgg acaagcccag taactgcacc aacgagctgt acatgatgat gcgggactgc tggcatgcag tgccctcaca gagacccacc ttcaagcagc tggtggaaga cctggaccgc atcgtggcct tgacctccaa ccaggagtac ctggacctgt ccatgccct ggaccagtac tcccccagct ttcccgacac ccggagctct acgtgctcct caggggagga ttccgtcttc tctcatgagc cgctgcccga ggagccctgc ctgccccgac acccagccca gcttgccaat ggcggactca aacgccgctg actgccaccc acacgccctc cccagactcc accgtcagct gtaaccctca cccacagccc ctgctgggcc caccacctgt ccgtccctgt ccccttttcct gctggcagga gccggctgcc taccaggggc cttcctgtgt ggcctgcctt caccccactc agctcacctc tccctccacc tcctctccac ctgctggtga gaggtgcaaa gaggcagatc tttgctgcca gccacttcat ccctcccag atgttggacc aacacccctc cctgccacca ggcactgcct ggagggcagg gagtgggagc caatgaacag gcatgcaagt gagagcttcc tgagctttct cctgtcggtt tggtctgttt tgccttcacc cataagcccc tcgcactctg gtggcaggtg ccttgtcctc agggctacag cagtagggag gtcagtgctt cgtgcctcga ttgaaggtga cctctgcccc agataggtgg tgccagtggc ttattaattc cgatactagt ttgctttgct gaccaaatgc ctggtaccag aggatggtga ggcgaaggcc aggttggggg cagtgttgtg gccctggggc ccagccccaa actgggggct ctgtatatag ctatgaagaa acacaaagt gtataaatct gagtatatat ttacatgtct ttttaaaagg gtcgttacca gagatttacc catcgggtaa gatgctcctg gtggctggga ggcatcagtt gctatatatt aaaaacaaaa aagaaaaaaa aggaaaatgt ttttaaaaag gtcatatatt ttttgctact tttgctgttt tattttttta aattatgttc
```

-continued

```
taaacctatt ttcagtttag gtccctcaat aaaaattgct gctgcttcat ttatctatgg gctgtatgaa aagggtggga atgtccactg gaaagaaggg acacccacgg gccctggggc taggtctgtc ccgagggcac cgcatgctcc cggcgcaggt tccttgtaac ctcttcttcc taggtcctgc acccagacct cacgacgcac ctcctgcctc tccgctgctt ttggaaagtc agaaaaagaa gatgtctgct tcgagggcag gaaccccatc catgcagtag aggcgctggg cagagagtca aggcccagca gccatcgacc atggatggtt tcctccaagg aaaccggtgg ggttgggctg ggagggggc acctacctag gaatagccac ggggtagagc tacagtgatt aagaggaaag caagggcgcg gttgctcacg cctgtaatcc cagcactttg ggacaccgag gtgggcagat cacttcaggt caggagtttg agaccagcct ggccaactta gtgaaacccc atctctacta aaaatgcaaa aattatccag gcatggtggc acacgcctgt aatcccagct ccacaggagg ctgaggcaga atcccttgaa gctgggaggc ggaggttgca gtgagccgag attgcgccat tgcactccag cctgggcaac agagaaaaca aaaaggaaaa caaatgatga aggtctgcag aaactgaaac ccagacatgt gtctgccccc tctatgtggg catggttttg ccagtgcttc taagtgcagg agaacatgtc acctgaggct agttttgcat tcaggtccct ggcttcgttt cttgttggta tgcctcccca gatcgtcctt cctgtatcca tgtgaccaga ctgtatttgt tgggactgtc gcagatcttg gcttcttaca gttcttcctg tccaaactcc atcctgtccc tcaggaacgg ggggaaaatt ctccgaatgt ttttggtttt ttggctgctt ggaatttact tctgccacct gctggtcatc actgtcctca ctaagtggat tctggctccc ccgtacctca tggctcaaac taccactcct cagtcgctat attaaagctt atattttgct ggattactgc taaatacaaa agaaagttca atatgttttc atttctgtag ggaaaatggg attgctgctt taaatttctg agctagggat tttttggcag ctgcagtgtt ggcgactatt gtaaaattct ctttgtttct ctctgtaaat agcacctgct aacattacaa tttgtattta tgtttaaaga aggcatcatt tggtgaacag aactaggaaa tgaattttta gctcttaaaa gcatttgctt tgagaccgca caggagtgtc tttccttgta aaacagtgat gataaatttct gccttggccc taccttgaag caatgttgtg tgaaggatg aagaatctaa aagtcttcat aagtccttgg gagaggtgct agaaaaatat aaggcactat cataattaca gtgatgtcct tgctgttact actcaaatca cccacaaatt tccccaaaga ctgcgctagc tgtcaaataa aagacagtga aattgacctg aaaaaaaaaa aaaaaaa
```

As described above, reference sequence ID number on Genbank NM_023110 shows the nucleotide sequence for human FGFR1, transcript variant 1 (i.e. SEQ ID NO: 8) encodes a protein with the amino acid sequence of SEQ ID NO: 9 as follows:

```
mwswkcllfwavlvtatlctarpsptlpeqaqpwgapvevesflvhpgdllqlrcrlrddvqsinwlrd gvqlaesnrtritgeevevqdsvpadsglyacvtsspsgsdttyfsvnvsdalpssedddddsssee ketdntkpnrmpvapywtspekmekklhavpaaktvkfkcpssgtpnptlrwlkngkefkpdhriggyk vryatwsiimdsvvpsdkgnytciveneygsinhtyqldvversphrpilqaglpanktvalgsnvefm ckvysdpqphiqwlkhievngskigpdnlpyvqilktagvnttdkemevlhlrnvsfedageytclagn siglshhsawltvlealeerpavmtsplyleiiiyctgafliscmvgsivyvkmksgtkksdfhsqmav hklaksiplrrqvtvsadssasmnsgvllvrpsrlsssgtpmlagvseyelpedprwelprdrlvlgkp lgegcfgqvvlaeaigldkdkpnrvtkvavkmlksdatekdlsdlisememmkmigkhkniinllgact
```

```
qdgplyviveyaskgnlreylqarrppgleycynpshnpeeqlsskdlvscayqvargmeylaskkcih rdlaarnvlvtednvmkiadfglardihhidyykkttngrlpvkwmapealfdriythqsdvwsfgvll weiftlggspypgvpveelfkllkeghrmdkpsnotnelymmmrdcwhavpsqrptfkqlvedldriva ltsnqeyldlsmpldqyspsfpdtrsstcssgedsvfsheplpeepclprhpaglangglkrr
```

The protein encoded by this FGFR1, transcript variant 1 gene is a member of the fibroblast growth factor receptor (FGFR) family, where amino acid sequences are highly conserved between members and throughout evolution. FGFR family members differ from one another in their ligand affinities and tissue distribution. A full-length representative protein consists of an extracellular region, composed of three immunoglobulin-like domains, a single hydrophobic membrane-spanning segment, and a cytoplasmic tyrosine kinase domain. The extracellular portion of the protein interacts with fibroblast growth factors, setting in motion a cascade of downstream signals, ultimately influencing mitogenesis and differentiation. This particular family member binds both acidic and basic fibroblast growth factors and is involved in limb induction. Mutations in this gene have been associated with Pfeiffer syndrome, Jackson-Weiss syndrome, Antley-Bixler syndrome, osteoglophonic dysplasia, and autosomal dominant Kallmann syndrome. See Itoh et al., "The Complete Amino Acid Sequence of the Shorter Form of Human Basic Fibroblast Growth Factor Receptor Deduced from its cDNA," *Biochem Biophys Res Commun* 169(2): 680-685 (1990); Dode et al., "Kallmann Syndrome: Fibroblast Growth Factor Signaling Insufficiency?" *J Mol Med* 82(11):725-34 (2004); Coumoul et al., "Roles of FGF Receptors in Mammalian Development and Congenital Diseases," *Birth Defects Res C Embryo Today* 69(4):286-304 (2003), which are hereby incorporated by reference in their entirety. Alternatively, spliced variants which encode different protein isoforms have been described; however, not all variants have been fully characterized.

The nucleic acid and amino acid sequences for FGFR1 variants 2-6 may be found using the following reference sequence ID numbers on GenBank: FGFR1, transcript variant 2 (NM_015850), FGFR1, transcript variant 3 (NM_023105), FGFR1, transcript variant 4 (NM_023106), FGFR1, transcript variant 5 (NM_023107), FGFR1, transcript variant 6 (NM_023108), and FGFR1, transcript variant 9, (NM_023111). These sequences are hereby incorporated by reference in their entirety.

Hypophosphatemia may be due to renal phosphate wasting (such as, autosomal dominant hypophosphatemic rickets (ADHR), X-linked hypophosphatemia (XLH), autosomal recessive hypophosphatemic rickets (ARHR), fibrous dysplasia (FD), McCune-Albright syndrome complicated by fibrous dysplasia (MAS/FD), Jansen's metaphyseal chondrodysplasia (Jansen's Syndrome), autosomal dominant polycystic kidney disease (ADPKD), tumor-induced osteomalacia (TIO), and chronic metabolic acidosis), other inherited or acquired renal phosphate wasting disorders, alcoholic and diabetic ketoacidosis, acute asthma, chronic obstructive pulmonary disease (COPD), drug treatment of COPD, sepsis, recovery from organ (in particular, kidney) transplantation, parenteral iron administration, salicylate intoxication, severe trauma, chronic treatment with sucralfate and/or antacids, mechanical ventilation, eating disorder (such as, anorexia nervosa and bulimia nervosa), or the refeeding syndrome.

For each method, Klotho can have a nucleotide sequence of SEQ ID NO:6 and the FGF23 may have a nucleotide sequence of SEQ ID NO:2.

Administration of the inhibitor of FGF23-Klotho-FGF receptor complex formation may be carried out orally, parenterally, subcutaneously, intravenously, intramuscularly, intraperitoneally, by intranasal instillation, by implantation, by intracavitary or intravesical instillation, intraocularly, intraarterially, intralesionally, transdermally, or by application to mucous membranes. The inhibitor may be administered with a pharmaceutically-acceptable carrier.

For the purpose of the present invention the following terms are defined below.

The term "hypophosphatemia" refers to serum phosphate concentration below the normal range of 2.2 to 4.9 mg/dl (Dwyer et al., "Severe hypophosphatemia in postoperative patients," *Nutr Clin Pract* 7(6):279-283 (1992); Alon et al., "Calcimimetics as an adjuvant treatment for familial hypophosphatemic rickets," *Clin J Am Soc Nephrol* 3(3):658-664 (2008), which are hereby incorporated by reference in their entirety).

The term "renal phosphate wasting" refers to an inherited or acquired condition in which renal tubular reabsorption of phosphate is impaired.

The term "disease" or "disorder" is used interchangeably herein, and refers to any alteration in state of the body or of some of the organs, interrupting or disturbing the performance of the functions and/or causing symptoms such as discomfort, dysfunction, distress, or even death to the person afflicted or those in contact with a person. A disease or disorder can also relate to a distemper, ailing, ailment, malady, disorder, sickness, illness, complaint, inderdisposion, or affectation.

The terms "treat", "treating", "treatment" and the like are used interchangeably herein and mean obtaining a desired pharmacological and/or physiological effect. The effect may be prophylactic in terms of completely or partially preventing a disease or symptom thereof and/or may be therapeutic in terms of partially or completely curing a disease and/or adverse effect attributed the disease. "Treating" as used herein covers treating a disease in a vertebrate and particularly a mammal and most particularly a human, and includes: (a) preventing the disease from occurring in a subject which may be predisposed to the disease but has not yet been diagnosed as having it; (b) inhibiting the disease, i.e. arresting its development; or (c) relieving the disease, i.e. causing regression of the disease.

A "subject" can be any mammal, particularly farm animals, mammalian pets, and humans.

The inhibitor used to treat hypophosphatemia may be the C-terminal tail peptide of FGF23. The C-terminal tail peptide of FGF23 has an amino acid sequence of SEQ ID NO:11 or SEQ ID NO:12.

The sequences of $FGF23^{180-251}$, $FGF23^{180-205}$, and $FGF23^{28-251}$ are listed in Table 1.

TABLE 1

Schematic representation of the structure of FGF23 fragments

| Name of Peptide | Amino Acid Sequence |
|---|---|
| FGF23$^{28-251}$ (SEQ ID NO: 10) | asp llgsswggli hlytatarns yhlqihkngh vdgaphqtiy salmirseda gfvvitgvms rrylcmdfrg nifgshyfdp encrfqhqtl engydvyhsp qyhflvslgr akraflpgmn pppysqflsr rneiplihfn tpiprrhtr saeddserdpl nvlkprarmt papascsqel psaednspma sdplgvvrgg rvnthaggtg pegcrpfakfi |
| FGF23$^{180-251}$ (SEQ ID NO: 11) | s aeddserdpl nvlkprarmt papascsqel psaednspma sdplgvvrgg rvnthaggtg pegcrpfakf i |
| FGF23$^{180-205}$ (SEQ ID NO: 12) | s aeddserdpl nvlkprarmt papas |

The invention is particularly directed toward targeting FGF23-Klotho-FGF receptor complex formation which makes it possible to treat patients which have experienced hypophosphatemia associated with elevated or normal FGF23 levels or which would be expected to experience hypophosphatemia associated with elevated or normal FGF23 levels and thus is particularly directed towards preventing, inhibiting, or relieving the effects of hypophosphatemia. A subject is "treated" provided the subject experiences a therapeutically detectable and beneficial effect, which may be measured based on a variety of different criteria generally understood by those skilled in the art to be desirable with respect to the treatment of diseases related to hypophosphatemia.

The compounds of the present invention can be administered alone or with suitable pharmaceutical carriers, and can be in solid or liquid form such as, tablets, capsules, powders, solutions, suspensions, or emulsions.

The active compounds of the present invention may be orally administered, for example, with an inert diluent, or with an assimilable edible carrier, or they may be enclosed in hard or soft shell capsules, or they may be compressed into tablets, or they may be incorporated directly with the food of the diet. For oral therapeutic administration, these active compounds may be incorporated with excipients and used in the form of tablets, capsules, elixirs, suspensions, syrups, and the like. Such compositions and preparations should contain at least 0.1% of active compound. The percentage of the compound in these compositions may, of course, be varied and may conveniently be between about 2% to about 60% of the weight of the unit. The amount of active compound in such therapeutically useful compositions is such that a suitable dosage will be obtained. Preferred compositions according to the present invention are prepared so that an oral dosage unit contains between about 1 and 250 mg of active compound.

The tablets, capsules, and the like may also contain a binder such as gum tragacanth, acacia, corn starch, or gelatin; excipients such as dicalcium phosphate; a disintegrating agent such as corn starch, potato starch, alginic acid; a lubricant such as magnesium stearate; and a sweetening agent such as sucrose, lactose, or saccharin. When the dosage unit form is a capsule, it may contain, in addition to materials of the above type, a liquid carrier, such as a fatty oil.

Various other materials may be present as coatings or to modify the physical form of the dosage unit. For instance, tablets may be coated with shellac, sugar, or both. A syrup may contain, in addition to active ingredient, sucrose as a sweetening agent, methyl and propylparabens as preservatives, a dye, and flavoring such as cherry or orange flavor.

These active compounds may also be administered parenterally. Solutions or suspensions of these active compounds can be prepared in water suitably mixed with a surfactant, such as hydroxypropylcellulose. Dispersions can also be prepared in glycerol, liquid polyethylene glycols, and mixtures thereof in oils. Illustrative oils are those of petroleum, animal, vegetable, or synthetic origin, for example, peanut oil, soybean oil, or mineral oil. In general, water, saline, aqueous dextrose and related sugar solution, and glycols such as, propylene glycol or polyethylene glycol, are preferred liquid carriers, particularly for injectable solutions. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol), suitable mixtures thereof, and vegetable oils.

The compounds of the present invention may also be administered directly to the airways in the form of an aerosol. For use as aerosols, the compounds of the present invention in solution or suspension may be packaged in a pressurized aerosol container together with suitable propellants, for example, hydrocarbon propellants like propane, butane, or isobutane with conventional adjuvants. The materials of the present invention also may be administered in a non-pressurized form such as in a nebulizer or atomizer.

The compounds of the present invention may also be administered directly to the airways in the form of a dry powder. For use as a dry powder, the compounds of the present invention may be administered by use of an inhaler. Exemplary inhalers include metered dose inhalers and dry powdered inhalers. A metered dose inhaler or "MDI" is a pressure resistant canister or container filled with a product such as a pharmaceutical composition dissolved in a liquefied propellant or micronized particles suspended in a liquefied propellant. The correct dosage of the composition is delivered to the patient. A dry powder inhaler is a system operable with a source of pressurized air to produce dry powder particles of a pharmaceutical composition that is compacted into a very small volume. For inhalation, the system has a plurality of chambers or blisters each containing a single dose of the pharmaceutical composition and a select element for releasing a single dose.

Suitable powder compositions include, by way of illustration, powdered preparations of the active ingredients thoroughly intermixed with lactose or other inert powders acceptable for intrabronchial administration. The powder compositions can be administered via an aerosol dispenser or encased in a breakable capsule which may be inserted by the patient into a device that punctures the capsule and blows the powder out in a steady stream suitable for inhalation. The compositions can include propellants, surfactants and co-solvents and may be filled into conventional aerosol containers that are closed by a suitable metering valve.

A second aspect of the present invention relates to a method of screening for compounds suitable for treatment of hypophosphatemia associated with elevated or normal FGF23 levels. This method involves providing: FGF23, binary FGFR-Klotho complex, and one or more candidate compounds. The FGF23, the FGFR-Klotho complex, and the candidate compounds are combined under conditions effective for the FGF23 and the binary FGFR-Klotho complex to form a ternary complex if present by themselves. The candidate compounds, which prevent formation of the complex, are identified as being potentially suitable in treating hypophosphatemia associated with elevated or normal FGF23 levels.

For this method, a plurality of candidate compounds may be tested.

The candidate compound is contacted with an assay system according to the selected assay system and candidate compound. For example, in an in vitro cell culture system, the candidate compound may be added directly to the cell culture medium, or the cells may be transfected with the candidate compound, etc.

Surface plasmon resonance (SPR) spectroscopy is an in vitro method used to determine physical interaction between two or more proteins. SPR spectroscopy is useful for confirming the existence of a protein:protein interaction predicted by other research techniques (e.g., co-immunoprecipitation, yeast two-hybrid and density gradient centrifugation). The minimal requirement for SPR spectroscopy is the availability of purified proteins, one of which will be coupled to the surface of a biosensor chip.

Size-exclusion chromatography is another in vitro method used to determine physical interaction between two or more proteins. Size-exclusion chromatography is useful for confirming the existence of a protein:protein interaction predicted by other research techniques (e.g., co-immunoprecipitation, yeast two-hybrid and density gradient centrifugation). The minimal requirement for size-exclusion chromatography is the availability of purified proteins.

A pull-down assay is yet another in vitro method used to determine physical interaction between two or more proteins. Pull-down assays are useful for confirming the existence of a protein:protein interaction predicted by other research techniques (e.g., co-immunoprecipitation, yeast two-hybrid and density gradient centrifugation). The minimal requirement for a pull-down assay is the availability of a purified and tagged protein which will be used to capture and 'pull-down' a protein-binding partner.

A variety of interaction or binding assays can be used to determine that an agent specifically binds the binary FGFR-Klotho complex, such as the SPR interaction analysis described below. One aspect of the present invention utilizes SPR analysis of FGF23 protein/peptide binding to the binary FGFR-Klotho complex. The SPR analysis involved FGF23 protein/peptide immobilization by amine coupling on flow channels of a chip. Proteins were injected over the chip at a flow rate of 50 µl min$^{-1}$, and at the end of each protein injection (180 s), HBS-EP buffer (10 mM HEPES-NaOH, pH 7.4, 150 mM NaCl, 3 mM EDTA, 0.005% (v/v) polysorbate 20; 50 µl min$^{-1}$) was flowed over the chip to monitor dissociation for 180 s. The chip surface was then regenerated by injecting 50 µl of 2.0 M NaCl in 10 mM sodium acetate, pH 4.5. To control for nonspecific binding, FHF1B, which shares structural similarity with FGFs but does not exhibit any FGFR binding, was coupled to the control flow channel of the chip. For each protein injection over a FGF23 protein/peptide chip, the nonspecific responses from the FHF1B control flow channel were subtracted from the responses recorded for the flow channel onto which FGF23 protein/peptide was immobilized. To analyze FGF23 binding to the binary FGFR1c-Klotho complex, FGF23$^{28-251}$ was coupled to a chip, and increasing concentrations of 1:1 complex of the ectodomains of FGFR1c and Klotho in HBS-EP buffer were passed over the chip. To measure binding of the C-terminal tail of FGF23 to the binary FGFR1c-Klotho complex, FGF23$^{180-251}$ was immobilized on a chip, and increasing concentrations of 1:1 complex of the ectodomains of FGFR1c and Klotho in HBS-EP buffer were passed over the chip. To examine whether the C-terminal tail of FGF23 can compete with full-length FGF23 for binding to the binary FGFR1c-Klotho complex, FGF23$^{28-251}$ was immobilized on a chip. Increasing concentrations of FGF23$^{180-251}$ were mixed with a fixed concentration of 1:1 complex of the ectodomains of FGFR1c and Klotho in HBS-EP buffer, and the mixtures were passed over the chip. As a control, competition of FGF23 in solution with immobilized FGF23 for binding to the binary FGFR1c-Klotho complex was studied. Increasing concentrations of FGF23$^{28-251}$ were mixed with a fixed concentration of 1:1 complex of the ectodomains of FGFR1c and Klotho in HBS-EP buffer, and the mixtures were passed over the FGF23 chip. Competition of the FGF23 C-terminal tail peptide with full-length FGF23 for binding to the binary FGFR1c-Klotho complex was also studied using the "reverse" SPR assay format, where FGF23$^{180-251}$ was immobilized on a chip and mixtures of a fixed concentration of 1:1 complex of the ectodomains of FGFR1c and Klotho with increasing concentrations of FGF23$^{28-251}$ were passed over the chip. As a control, competition of FGF23 C-terminal tail peptide in solution with immobilized FGF23 C-terminal tail peptide for binding to the binary FGFR1c-Klotho complex was analyzed. Increasing concentrations of FGF23$^{180-251}$ were mixed with a fixed concentration of 1:1 complex of the ectodomains of FGFR1c and Klotho in HBS-EP buffer, and the mixtures were passed over the FGF23$^{180-251}$ chip. To verify the specificity of the interaction between the FGF23 C-terminal tail and the FGFR1c-Klotho complex, FGF23$^{28-251}$ was immobilized on a chip. Increasing concentrations of FGF21$^{168-209}$ were mixed with a fixed concentration of 1:1 complex of the ectodomains of FGFR1c and Klotho in HBS-EP buffer, and the mixtures were passed over the chip. In addition, the ability of the FGF23 C-terminal tail peptide to interfere with binary complex formation between βKlotho and either FGF19 or FGF21 was tested, as was its ability to interfere with ternary complex formation between βKlotho, FGFR, and either FGF19 or FGF21. FGF19$^{23-216}$ and FGF21$^{29-209}$ were immobilized on two flow channels of a chip. FGF23$^{180-251}$ and the ectodomain of βKlotho were mixed at a molar ratio of 2:1, and the mixture was injected over the chip. Next, FGF23$^{180-251}$ and the 1:1 complex of the ectodomains of FGFR1c and βKlotho were mixed at a molar ratio of 10:1, and the mixture was passed over the FGF19/FGF21 chip. To examine whether a C-terminal FGF23 peptide comprising the minimal binding epitope for the binary FGFR-Klotho complex can compete with full-length FGF23 for binding to FGFR1c-Klotho, increasing concentrations of FGF23$^{180-205}$ were mixed with a fixed concentration of 1:1 complex of the ectodomains of FGFR1c and Klotho in HBS-EP buffer, and the mixtures were passed over a chip onto which FGF23$^{28-251}$ had been immobilized.

Size-exclusion chromatography may also be used to determine that an agent specifically binds the binary FGFR-Klotho complex. One aspect of the present invention utilizes size-exclusion chromatography. The size-exclusion chromatography experiments were performed on a HiLoad™ 16/60 Superdex™ 200 prep grade column. Because of poor solubility of FGF23 proteins and FGFR1c ectodomain in low salt buffer, the experiments were carried out with 25 mM HEPES-NaOH buffer, pH7.5, containing 1.0 M NaCl. Sample injection volume was 0.3 to 1.0 ml, and the flow rate was 1.0 ml min$^{-1}$. Protein retention times were determined by absorbance at 280 nm. The column was calibrated with ferritin (440 kDa), immunoglobulin G (150 kDa), albumin (69.3 kDa), ovalbumin (44.3 kDa), and carbonic anhydrase (28.8 kDa). The void volume was determined using blue dextran 2,000. To examine binding of FGF23 proteins to the 1:1 binary complex of the ectodomains of FGFR1c and Klotho, FGFR1c-Klotho complex was mixed with a slight molar excess of either FGF23$^{28-251}$ or FGF23$^{28-179}$ or FGF23$^{180-251}$, and the mixtures were applied to the size-exclusion column. The retention time of the FGFR1c-Klotho complex alone served as a reference point. Proteins of column peak fractions were resolved on 14% SDS-polyacrylamide gels, and then stained with Coomassie Brilliant Blue R-250.

A pull-down assay may also be used to confirm the existence of a protein:protein interaction (i.e. FGF23$^{180-251}$ binding to the binary FGFR-Klotho complex). One aspect of the present invention utilizes pull-down assays. These assays involved subconfluent cultures of a HEK293 cell line ectopically expressing the FLAG-tagged membrane-spanning form of murine Klotho, which were harvested and lysed. Cell lysate was incubated with FGF23$^{28-251}$, FGF23$^{28-200}$, FGF23$^{28-179}$, FGF23$^{180-251}$, or protein sample buffer, and binary complexes of Klotho and endogenous FGFR were isolated from cell lysate using anti-FLAG M2 agarose beads. Bead-bound proteins were resolved together with controls (FGF23 protein) on 14% SDS-polyacrylamide gels, transferred to nitrocellulose membranes, and labeled using horseradish peroxidase-conjugated India-HisProbe.

Co-immunoprecipitation may also be used to determine that an agent specifically binds the binary FGFR-Klotho complex. One aspect of the present invention utilizes co-immunoprecipitation studies. Subconfluent cultures of a HEK293 cell line ectopically expressing the FLAG-tagged membrane-spanning form of murine Klotho were transfected with expression vectors for V5-tagged FGFR1c, FGFR3c, or FGFR4. Two days later, the cells were lysed, and FGFR-Klotho complexes were isolated from cell lysate using anti-V5 agarose beads. The beads were then incubated with either FGF23$^{180-251}$ or FGF23$^{28-251}$ alone, or with mixtures of FGF23$^{28-251}$ with either increasing FGF23$^{180-251}$ or increasing FGF23$^{180-205}$. Bead-bound proteins were resolved on SDS-polyacrylamide gels, transferred to nitrocellulose membranes, and labeled using antibodies to Klotho, FGF23, and V5 epitope tag.

Serum FGF23 level may be evaluated in an individual with hypophosphatemia by immunoassay. This includes two kinds of enzyme linked immunoabsorbant assay (ELISA): a full-length assay that detects only full-length FGF23 with phosphate-lowering activity and a C-terminal assay that measures full-length as well as C-terminal fragment of FGF23. The FGF23 gene may be analyzed by direct sequencing of PCR products, and mutant FGF23 may be analyzed by Western blotting using two kinds of monoclonal antibodies that recognize N- and C-terminal portion of the processing site of FGF23 after expression in mammalian cells.

In addition to full-length peptides, the present invention provides for peptides having the biological activity of FGF23, as defined herein. One skilled in the art would appreciate, based on the sequences disclosed herein, that overlapping fragments of FGF23 can be generated using standard recombinant technology, for example, that described in Sambrook et al. (Molecular Cloning: A Laboratory Manual, Cold Spring Harbor Laboratory Press, New York, 1989) and Ausubel et al. (Current Protocols in Molecular Biology, Green & Wiley, New York, 1997), which are hereby incorporated by reference in their entirety. One skilled in the art would appreciate, based on the disclosure presented herein, that the biological activity of FGF23 fragments could be tested by injecting the material into mice and evaluating whether injected mice exhibit increased renal phosphate excretion and hypophosphatemia. Induction of phosphate excretion and hypophosphatemia would serve as an indication that the FGF23 fragment retained biological activity. In addition, in vitro assays can be used to test FGF23 biological activity. For example, isolated renal tubules may be perfused with FGF23 fragments and evaluated for alterations in phosphate transport, relative to wild-type FGF23. Similarly, cell culture models which possess the necessary FGF23 signal transduction machinery (i.e. FGF receptor 1, Klotho, and type II sodium-dependent phosphate transporter) may be transfected with FGF23 fragments and subsequently tested for alterations in phosphate transport, relative to wild-type FGF23.

In situ hybridization assays are used to measure the level of expression for normal cells and suspected cells from a tissue sample. Labelling of the nucleic acid sequence allows for the detection and measurement of relative expression levels. By comparing the level of expression between normal cells and suspected cells from a tissue sample, candidate compounds suitable for treatment of hypophosphatemia associated with elevated or normal FGF23 may be identified by the reduced expression level of the gene product.

An approach to detecting the presence of a given sequence or sequences in a polynucleotide sample involves selective amplification of the sequence(s) by polymerase chain reaction. PCR is described in U.S. Pat. No. 4,683,202 to Mullis et al. and Saiki et al., "Enzymatic Amplification of Beta-globin Genomic Sequences and Restriction Site Analysis for Diagnosis of Sickle Cell Anemia," Science 230:1350-1354 (1985), which are hereby incorporated by reference in their entirety. In this method, primers complementary to opposite end portions of the selected sequence(s) are used to promote, in conjunction with thermal cycling, successive rounds of primer-initiated replication. The amplified sequence(s) may be readily identified by a variety of techniques. This approach is particularly useful for detecting candidate compounds suitable for treatment of hypophosphatemia associated with elevated or normal FGF23.

The present invention also relates to a method of screening the specificity of compounds which prevent formation of the FGF23-Klotho-FGFR complex. This method involves providing FGF19, providing binary FGFR-βKlotho complex, and providing one or more candidate compounds. The FGF19, the binary FGFR-βKlotho complex, and the candidate compounds are combined under conditions effective for the FGF19 and the binary FGFR-βKlotho complex to form a ternary complex if present by themselves. Candidate compounds which do not interfere with formation of the complex are identified as being specific and potentially suitable in treating hypophosphatemia associated with elevated or normal FGF23 levels.

This aspect of the present invention is carried out with many of the procedures described with respect to the screening method of the second aspect of the present invention as described above. FGF19 can be replaced with FGF21. The FGF receptor may have the amino acid sequence of SEQ ID NO:9. This aspect of the present invention can be carried out using surface plasmon resonance spectroscopy.

EXAMPLES

The following examples are provided to illustrate embodiments of the present invention but are by no means intended to limit its scope.

Materials and Methods for Examples 1-8

Purification of FGF19, FGF21, FGF23, FGFR, Klotho and βKlotho Proteins and Purification/Synthesis of FGF21 and FGF23 Peptides Human FGF19 (R23 to K216, referred to as FGF19$^{23-216}$), human FGF21 (H29 to S209, referred to as FGF21$^{29-209}$), human FGF23 (A28 to I251, referred to as FGF23$^{28-251}$; FIG. 1A) and C-terminally truncated FGF23 proteins (A28 to T200, referred to as FGF23$^{28-200}$; A28 to R179, referred to as FGF23$^{28-179}$; FIG. 1A) were expressed in E. coli, refolded in vitro, and purified by published protocols (Ibrahimi et al., "Biochemical Analysis of Pathogenic Ligand-dependent FGFR2 Mutations Suggests Distinct Pathophysiological Mechanisms for Craniofacial and Limb Abnormalities," *Hum Mol Genet* 13(19):2313-2324 (2004), Plotnikov et al., "Crystal Structures of Two FGF-FGFR Complexes Reveal the Determinants of Ligand-receptor Specificity," *Cell* 101(4):413-424 (2000), which are hereby incorporated by reference in their entirety). In order to minimize proteolysis of FGF23$^{28-251}$ and FGF23$^{28-200}$, arginine residues 176 and 179 of the proteolytic cleavage site $^{176}$RXXR$^{179}$ (SEQ ID NO: 1) were replaced with glutamine as it occurs in ADHR (Anonymous, "Autosomal Dominant Hypophosphataemic Rickets is Associated with Mutations in FGF23," *Nat Genet* 26(3):345-348 (2000); White et al., "Autosomal-dominant Hypophosphatemic Rickets (ADHR) Mutations Stabilize FGF-23," *Kidney Int* 60(6):2079-2086 (2001), which are hereby incorporated by reference in their entirety). The bacterially expressed FGF23$^{28-251}$ protein exhibited similar bioactivity as full-length FGF23 produced using a mammalian expression system, as judged by similar ability of the two protein preparations to induce tyrosine phosphorylation of FRS2α and downstream activation of MAP kinase cascade in a HEK293 cell line ectopically expressing the membrane-spanning form of murine Klotho (Kurosu et al., "Regulation of fibroblast growth factor-23 signaling by klotho," *J Biol Chem* 281(10):6120-6123 (2006), which is hereby incorporated by reference in its entirety). Human fibroblast growth factor homologous factor 1B (FHF1B) was purified by a published protocol (Olsen et al., "Fibroblast growth factor (FGF) homologous factors share structural but not functional homology with FGFs," *J Biol Chem* 278(36):34226-34236 (2003), which is hereby incorporated by reference in its entirety). Purified human FGF2 (M1 to S155) was obtained from Upstate Biotechnology. The ligand-binding domain of human FGFR1c (D142 to R365) was expressed in E. coli and purified by published protocols (Anonymous, "Autosomal Dominant Hypophosphataemic Rickets is Associated with Mutations in FGF23," *Nat Genet* 26(3):345-348 (2000); White et al., "Autosomal-dominant Hypophosphatemic Rickets (ADHR) Mutations Stabilize FGF-23," *Kidney Int* 60(6): 2079-2086 (2001), which are hereby incorporated by reference in their entirety). The ectodomain of murine Klotho (A35 to K982) was purified from culture media of a HEK293 cell line ectopically expressing the Klotho ectodomain as a fusion protein with a C-terminal FLAG tag (Kurosu et al., "Regulation of fibroblast growth factor-23 signaling by klotho," *J Biol Chem* 281(10):6120-6123 (2006); Kurosu et al., "Suppression of aging in mice by the hormone Klotho," *Science* 309(5742):1829-1833 (2005), which are hereby incorporated by reference in their entirety). Similarly, the ectodomain of murine βKlotho (F53 to L995) was expressed in HEK293 cells as a fusion protein with a C-terminal FLAG tag and purified using the same protocol as for the Klotho ectodomain. Purified bovine β-glucuronidase was obtained from Sigma-Aldrich.

The N-terminally hexahistidine-tagged, 72-amino acid C-terminal tail of human FGF23 (S180 to I251, referred to as FGF23$^{180-251}$; FIG. 1A) was expressed in E. coli, and purified by nickel affinity-, ion-exchange- and size-exclusion chromatographies. A shorter peptide of the FGF23 C-terminal region (S180 to S205, referred to as FGF23$^{180-205}$; FIG. 1A) was synthesized by solid phase synthesis (GenScript Corporation). The N-terminally hexahistidine-tagged, 42-amino acid long C-terminal tail of FGF21 (P168 to S209, referred to as FGF21$^{168-209}$) was expressed in E. coli, and purified by nickel affinity- and ion-exchange chromatographies.

Analysis of FGF23-FGFR1c-Klotho Interactions by Surface Plasmon Resonance Spectroscopy Surface plasmon resonance (SPR) spectroscopy experiments were performed on a Biacore 2000 instrument (Biacore AB), and FGF23-FGFR1c-Klotho interactions were studied at 25° C. in HBS-EP buffer (10 mM HEPES-NaOH, pH 7.4, 150 mM NaCl, 3 mM EDTA, 0.005% (v/v) polysorbate 20). Proteins were immobilized by amine coupling on flow channels of research grade CM5 chips (Biacore AB). Proteins were injected over a CM5 chip at a flow rate of 50 μl min$^{-1}$, and at the end of each protein injection (180 s), HBS-EP buffer (50 μl min$^{-1}$) was flowed over the chip to monitor dissociation for 180 s. The chip surface was then regenerated by injecting 50 μl of 2.0 M NaCl in 10 mM sodium acetate, pH 4.5. To control for nonspecific binding in experiments where Klotho ectodomain was immobilized on the chip, β-glucuronidase was coupled to the control flow channel of the chip (~26-32 fmole/mm$^2$). Like Klotho, β-glucuronidase is a member of family 1 glycosidases, and hence structurally related to each of the two extracellular glycosidase-like domains of Klotho. In experiments where FGF19, FGF21, FGF23 or the C-terminal tail of FGF23 were immobilized on the chip, FHF1B, which shares structural similarity with FGFs but does not exhibit any FGFR binding (Olsen et al., "Fibroblast growth factor (FGF) homologous factors share structural but not functional homology with FGFs," *J Biol Chem* 278(36):34226-34236 (2003), which is hereby incorporated by reference in its entirety), was coupled to the control flow channel of the chip (~14-71 fmole/mm$^2$) The data were processed with BiaEvaluation software (Biacore AB). For each protein injection over a Klotho chip, the nonspecific responses from the β-glucuronidase control flow channel were subtracted from the responses recorded for the Klotho flow channel. Similarly, for each protein injection over a FGF chip, the nonspecific responses from the FHF1B control flow channel were subtracted from the responses recorded for the FGF flow channel. Each set of experiments was repeated at least three times, and for each experiment, at least two protein injections were repeated two to five times to monitor chip performance and to verify reproducibility of the binding responses.

To analyze Klotho binding to FGFR1c, Klotho ectodomain was immobilized on a chip (~29-35 fmole/mm$^2$ of flow channel). Increasing concentrations of FGFR1c ectodomain in HBS-EP buffer were injected over the chip. Maximal equilibrium responses were plotted against the concentrations of FGFR1c ectodomain (FIG. 1B), and from the fitted saturation binding curve the equilibrium dissociation constant ($K_D$) was calculated. The fitted binding curve was judged to be accurate based on the distribution of the residuals (even and near zero) and $\chi^2$ (<10% of $R_{max}$).

To analyze FGF23 binding to both Klotho and FGFR1c alone, and to the binary FGFR1c-Klotho complex, $FGF23^{28-251}$ was coupled to a chip (~16-53 fmole/mm$^2$ of flow channel). To measure FGF23 binding to Klotho, increasing concentrations of Klotho ectodomain in HBS-EP buffer were passed over the chip. To analyze FGF23 interaction with FGFR1c, increasing concentrations of FGFR1c ectodomain in HBS-EP buffer were injected over the chip. To measure FGF23 binding to the binary FGFR1c-Klotho complex, increasing concentrations of 1:1 complex of the ectodomains of FGFR1c and Klotho in HBS-EP buffer were passed over the FGF23 chip.

To analyze binding of the C-terminal tail of FGF23 to the binary FGFR1c-Klotho complex, $FGF23^{180-251}$ was immobilized on a chip (~48 fmole/mm$^2$ of flow channel), and increasing concentrations of 1:1 complex of the ectodomains of FGFR1c and Klotho in HBS-EP buffer were passed over the chip.

To examine whether the C-terminal tail of FGF23 can compete with full-length FGF23 for binding to the binary FGFR1c-Klotho complex, two assay formats were employed. In one assay, $FGF23^{28-251}$ was immobilized on a chip (~16-53 fmole/mm$^2$ of flow channel). Increasing concentrations of $FGF23^{180-251}$ (0-400 nM) were mixed with a fixed concentration of 1:1 complex of the ectodomains of FGFR1c and Klotho (10 nM, 15 nM and 20 nM, respectively) in HBS-EP buffer, and the mixtures were passed over the chip. As a control, competition of FGF23 in solution with immobilized FGF23 for binding to the binary FGFR1c-Klotho complex was studied. Increasing concentrations of $FGF23^{28-251}$ (0-50 nM) were mixed with a fixed concentration of 1:1 complex of the ectodomains of FGFR1c and Klotho (15 nM and 20 nM, respectively) in HBS-EP buffer, and the mixtures were passed over the FGF23 chip. In the other—reverse—assay, $FGF23^{180-251}$ was immobilized on a chip (~48.4 fmole/mm$^2$ of flow channel). Increasing concentrations of $FGF23^{28-251}$ (0-50 nM) were mixed with a fixed concentration of 1:1 complex of the ectodomains of FGFR1c and Klotho (20 nM) in HBS-EP buffer, and the mixtures were passed over the chip. As a control, competition of FGF23 C-terminal tail peptide in solution with immobilized FGF23 C-terminal tail peptide for binding to the binary FGFR1c-Klotho complex was studied. Increasing concentrations of $FGF23^{180-251}$ (0-400 nM) were mixed with a fixed concentration of 1:1 complex of the ectodomains of FGFR1c and Klotho (20 nM) in HBS-EP buffer, and the mixtures were passed over the $FGF23^{180-251}$ chip.

To examine whether a C-terminal FGF23 peptide comprising the minimal binding epitope for the binary FGFR-Klotho complex can compete with full-length FGF23 for binding to FGFR1c-Klotho, increasing concentrations of $FGF23^{180-205}$ (0-800 nM) were mixed with a fixed concentration of 1:1 complex of the ectodomains of FGFR1c and Klotho (15 nM and 20 nM, respectively) in HBS-EP buffer, and the mixtures were passed over a chip onto which $FGF23^{28-251}$ had been immobilized (~16 fmole/mm$^2$ of flow channel).

To examine whether the C-terminal tail of FGF21 can compete with full-length FGF23 for binding to binding to the binary FGFR1c-Klotho complex, $FGF23^{28-251}$ was immobilized on a chip (~16 fmole/mm$^2$ of flow channel). $FGF21^{168-209}$ was mixed with the 1:1 complex of the ectodomains of FGFR1c and Klotho at molar ratios of 6:1 and 10:1, and the mixtures were passed over the chip.

To examine whether the C-terminal tail peptide of FGF23 interferes with binary complex formation between βKlotho and either FGF19 or FGF21, $FGF19^{23-216}$ and $FGF21^{29-209}$ were immobilized on two flow channels of a chip (~29 fmole/mm$^2$ of flow channel). $FGF23^{180-251}$ and the ectodomain of βKlotho were mixed at a molar ratio of 2:1, and the mixture was injected over the chip.

To examine whether the C-terminal tail peptide of FGF23 interferes with ternary complex formation between βKlotho, FGFR, and either FGF19 or FGF21, $FGF23^{180-251}$ and the 1:1 complex of the ectodomains of FGFR1c and βKlotho were mixed at a molar ratio of 10:1, and the mixture was passed over a chip onto which $FGF19^{23-216}$ and $FGF21^{29-209}$ had been immobilized (~29 fmole/mm$^2$ of flow channel).

Analysis of FGF23 Protein/Peptide Binding to FGFR1c-Klotho Complex by Size-Exclusion Chromatography Size-exclusion chromatography experiments were performed on a HiLoad™ 16/60 Superdex™ 200 prep grade column (GE Healthcare) mounted on an ÄKTApurifier (GE Healthcare). Because of poor solubility of FGF23 proteins and FGFR1c ectodomain in low salt buffer, the experiments were carried out with 25 mM HEPES-NaOH buffer, pH7.5, containing 1.0 M NaCl. Sample injection volume was 0.3 to 1.0 ml, and the flow rate was 1.0 ml min$^{-1}$. Protein retention times were determined by absorbance at 280 nm. The column was calibrated with ferritin (440 kDa), immunoglobulin G (150 kDa), albumin (69.3 kDa), ovalbumin (44.3 kDa), and carbonic anhydrase (28.8 kDa). The void volume was determined using blue dextran 2,000. To examine binding of FGF23 proteins to the 1:1 binary complex of the ectodomains of FGFR1c and Klotho, 1.0 to 3.0 μmol of FGFR1c-Klotho complex were mixed with a 3- to 5-fold molar excess of either $FGF23^{28-251}$ or $FGF23^{28-179}$ or $FGF23^{180-251}$, and the mixtures were applied to the size-exclusion column. The retention time of the FGFR1c-Klotho complex alone served as a reference point. Proteins of column peak fractions were resolved on 14% SDS-polyacrylamide gels, and then stained with Coomassie Brilliant Blue R-250.

Cell Culture-Pull-Down Assays of FGF23 Protein/Peptide Binding to FGFR-Klotho Complex Subconfluent cultures of a HEK293 cell line ectopically expressing the FLAG-tagged membrane-spanning form of murine Klotho (HEK293-Klotho; Kurosu et al., "Regulation of Fibroblast Growth Factor-23 Signaling by Klotho," *J Biol Chem* 281(10):6120-6123 (2006), which is hereby incorporated by reference in its entirety), were harvested and lysed (Goetz et al., "Molecular Insights into the Klotho-dependent, Endocrine Mode of Action of Fibroblast Growth Factor 19 Subfamily Members," *Mol Cell Biol* 27(9):3417-3428 (2007), which is hereby incorporated by reference in its entirety). Cell lysate was incubated with 2.7 nmoles of $FGF23^{28-251}$, $FGF23^{28-200}$, $FGF23^{28-179}$, $FGF23^{180-251}$, or protein sample buffer, and binary complexes of Klotho and endogenous FGFR were isolated from cell lysate using anti-FLAG M2 agarose beads (Sigma-Aldrich) (Goetz et al., "Molecular Insights into the Klotho-dependent, Endocrine Mode of Action of Fibroblast Growth Factor 19 Subfamily Members," *Mol Cell Biol* 27(9):3417-3428 (2007), which is hereby incorporated by reference in its entirety). Bead-bound proteins were resolved together with controls (130 to 250 ng of each FGF23 protein) on 14% SDS-polyacrylamide gels, transferred to nitrocellulose membranes, and labeled using horseradish peroxidase-conjugated India-HisProbe (Pierce).

In parallel, subconfluent HEK293-Klotho cells (Kurosu et al., "Regulation of Fibroblast Growth Factor-23 Signaling by Klotho," *J Biol Chem* 281(10):6120-6123 (2006), which is hereby incorporated by reference in its entirety) were transfected with expression vectors for V5-tagged FGFR1c, FGFR3c, or FGFR4 (Kurosu et al., "Regulation of Fibroblast Growth Factor-23 Signaling by Klotho," *J Biol Chem* 281(10):6120-6123 (2006), which is hereby incorporated by reference in its entirety) and binding of FGF23 proteins/peptides to Klotho-FGFR complexes isolated from cell lysate was analyzed. Two days later, the cells were lysed (Kurosu et al, "Suppression of Aging in Mice by the Hormone Klotho," *Science* 309(5742):1829-1833 (2005), which is hereby incorporated by reference in its entirety), and FGFR-Klotho complexes were isolated from cell lysate using anti-V5 agarose beads (Sigma-Aldrich) (Kurosu et al., "Regulation of Fibroblast Growth Factor-23 Signaling by Klotho," *J Biol Chem* 281(10):6120-6123 (2006), which is hereby incorporated by reference in its entirety). The beads were then incubated with either $FGF23^{180-251}$ (1 nM) or $FGF23^{28-251}$ (1 nM) alone, or with mixtures of $FGF23^{28-251}$ (1 nM) with either increasing $FGF23^{180-251}$ (2 to 76 nM) or increasing $FGF23^{180-205}$ (0.1 to 10 μM). Bead-bound proteins were resolved on SDS-polyacrylamide gels, transferred to nitrocellulose membranes, and labeled using antibodies to Klotho (KM2119, (Kato et al., "Establishment of the Anti-Klotho Monoclonal Antibodies and Detection of Klotho Protein in Kidneys," *Biochemical Biophysical Res Communications* 267(2):597-602 (2000), which is hereby incorporated by reference in its entirety)), FGF23 (R&D systems), and V5 epitope tag (Invitrogen).

Analysis of Phosphorylation of FRS2α and 44/42 MAP Kinase in Epithelial Cell Lines Subconfluent HEK293-Klotho cells (Kurosu et al., "Regulation of Fibroblast Growth Factor-23 Signaling by Klotho," *J Biol Chem* 281(10):6120-6123 (2006), which is hereby incorporated by reference in its entirety) were serum starved for 16 h and then stimulated for 10 min with either $FGF23^{28-251}$ (0.33 to 10 nM) or $FGF23^{180-251}$ (0.76 to 76.3 nM). In parallel experiments, cells were stimulated with $FGF23^{28-251}$ (1 nM) alone or with $FGF23^{28-251}$ (1 nM) mixed with increasing concentrations of either $FGF23^{180-251}$ (0.76 to 76.3 nM) or $FGF23^{180-205}$ (0.1 to 10 μM). Cell stimulation with FGF2 (2.9 nM) alone or FGF2 (2.9 nM) mixed with increasing concentrations of $FGF23^{180-251}$ (0.76 to 76.3 nM) served as controls. Similarly, subconfluent cells of a CHO cell line stably expressing Klotho (Imura et al., "Secreted Klotho Protein in Sera and CSF: Implication for Post-translational Cleavage in Release of Klotho Protein from Cell Membrane," *FEBS Lett* 565(1-3):143-147 (2004), which is hereby incorporated by reference in its entirety) were treated with either $FGF23^{28-251}$ (0.067 to 20 nM) or $FGF23^{28-200}$ (0.04 to 12 nM).

In a separate experiment, the biological activity of the bacterially expressed $FGF23^{28-251}$ protein was compared to that of $FGF23^{25-251}$ expressed in the mouse myeloma cell line NS0 (R&D Systems). Subconfluent HEK293-Klotho cells were serum starved, and then treated with either of the two FGF23 proteins.

After stimulation, the cells were lysed (Kurosu et al, "Suppression of Aging in Mice by the Hormone Klotho," *Science* 309(5742):1829-1833 (2005), which is hereby incorporated by reference in its entirety), and cellular proteins were resolved on SDS-polyacrylamide gels, transferred to nitrocellulose membranes, and the protein blots were probed with antibodies to phosphorylated FGF receptor substrate-2α (FRS2α), phosphorylated 44/42 MAP kinase and non-phosphorylated 44/42 MAP kinase, and Klotho. Except for the anti-Klotho antibody (Kato et al., "Establishment of the Anti-Klotho Monoclonal Antibodies and Detection of Klotho Protein in Kidneys," *Biochemical Biophysical Res Communications* 267(2):597-602 (2000), which is hereby incorporated by reference in its entirety), all antibodies were from Cell Signaling Technology.

Measurement of Phosphate Uptake by Opossum Kidney Cells

The effects of FGF23 proteins/peptides on sodium-coupled phosphate uptake were studied in the opossum kidney cell line OKP (Miyauchi et al., "Stimulation of transient elevations in cytosolic Ca2+ is related to inhibition of Pi transport in OK cells," *Am J Physiol* 259(3 Pt 2):F485-493 (1990), which is hereby incorporated by reference in its entirety). The cell line has many characteristics of renal proximal tubule epithelium, including sodium gradient-dependent phosphate transport and sensitivity to parathyroid hormone (Miyauchi et al., "Stimulation of transient elevations in cytosolic Ca2+ is related to inhibition of Pi transport in OK cells," *Am J Physiol* 259(3 Pt 2):F485-493 (1990), which is hereby incorporated by reference in its entirety). OKP cells also express FGFR1-4 and Klotho (see next methods section). OKP cells were grown in culture as described previously (Hu et al., "Dopamine Acutely Stimulates Na+/H+ Exchanger (NHE3) Endocytosis Via Clathrin-coated Vesicles: Dependence on Protein Kinase A-mediated NHE3 Phosphorylation," *J Biol Chem* 276(29):26906-26915 (2001), which is hereby incorporated by reference in its entirety). Cells grown in 24-well plates were stimulated for 4 h with $FGF23^{28-251}$ (0.5 to 1 nM), $FGF23^{180-251}$ (500 nM), $FGF23^{180-205}$ (500 nM), or mixtures of $FGF23^{28-251}$ (1 nM) with either $FGF23^{180-251}$ (1 to 500 nM) or $FGF23^{180-205}$ (1 to 500 nM). The 1 nM concentration of $FGF23^{28-251}$ was chosen for competition experiments with FGF23 C-terminal peptides because at this concentration, half-maximum inhibition of phosphate uptake is reached. After stimulation, the cells were rinsed with Na+-free solution followed by 5 min incubation with uptake solution containing 100 μM $KH_2^{32}PO_4$ (2 mCi/ml, Perkin Elmer). The reaction was stopped by aspiration of uptake solution and washing cells with ice-cold stop solution (10 mM HEPES pH 7.4, 140 mM NaCl, 1 mM $MgCl_2$). Each transport reaction was performed in triplicates.

Analysis of FGFR and Klotho mRNA Expression in Opossum Kidney Cells

Total RNA was extracted from the OKP cell line (Miyauchi et al., "Stimulation of transient elevations in cytosolic Ca2+ is related to inhibition of Pi transport in OK cells," *Am J Physiol* 259(3 Pt 2):F485-493 (1990), which is hereby incorporated by reference in its entirety) using RNeasy kit (Qiagen). 5 μg of total RNA was used for cDNA synthesis with random hexamer primers using SuperScript III First Strand Synthesis System (Invitrogen). FGFR1-4, Klotho, and β-actin transcripts were detected by PCR using Platinum Taq DNA Polymerase (Invitrogen). The PCR conditions were 94° C. for 1 min followed by 35 cycles of 95° C. for 30 s, 54° C. for 30 s, and 72° C. for 60 s. The primers used were 5'-TGATTTG-CATTCTCCACCAA-3' (SEQ ID NO: 13) and 5'-CTTCTC-CCCGCTTTTCTTCT-3' (SEQ ID NO: 14) (FGFR1); 5'-TATGGGCCAGATGGATTACC-3' (SEQ ID NO: 15) and 5'-GCACGTATACTCCCCAGCAT-3' (SEQ ID NO: 16) (FGFR2); 5'-ACCTGGTGTCCTGTGCCTAC-3' (SEQ ID NO: 17) and 5'-CATTCGATGGCCCTCTTTTA-3' (SEQ ID NO: 18) (FGFR3); 5'-CTGAAGCACATCGAGGTCAA-3' (SEQ ID NO: 19) and 5'-CCTGACTCCAGGGAGAACTG-3' (SEQ ID NO: 20) (FGFR4); 5'-AGCCCTCGAAAGAT-GACTGA-3' (SEQ ID NO: 21) and 5'-ACAAACCAGCCAT-TCTCCAC-3' (SEQ ID NO: 22) (Klotho); and 5'-GTGGGGGATGAGGCCCAGAG-3' (SEQ ID NO: 23) and 5'-AGCTGTGGTGGTGAAACTGT-3' (SEQ ID NO:

24) (β-actin). PCR products were resolved on 2% agarose gels containing ethidium bromide.

Measurement of Phosphate in Serum and Urine of Rodents

The phosphaturic activity of FGF23$^{28-200}$ was examined in ~6-week old C57BL/6 mice by a published protocol (Goetz et al., "Molecular Insights into the Klotho-dependent, Endocrine Mode of Action of Fibroblast Growth Factor 19 Subfamily Members," Mol Cell Biol 27(9):3417-3428 (2007), which is hereby incorporated by reference in its entirety). FGF23$^{28-251}$, FGF23$^{28-200}$, or vehicle were injected IP into the animals. Each mouse received two injections at 8 h intervals, of 5 µg of protein per injection. Before the first injection and 8 h after the second injection, blood was drawn by cheekpouch bleeding and spun at 3,000×g for 10 min to obtain serum. Serum phosphate levels were determined using Phosphorus Liqui-UV reagent (Stanbio Laboratory).

The anti-phosphaturic activity of FGF23 C-terminal peptides was examined in normal Sprague-Dawley rats and in Hyp mice, a mouse model of human X-linked hypophosphatemia (XLH) (Beck et al., "Pex/PEX Tissue Distribution and Evidence for a Deletion in the 3' Region of the Pex Gene in X-linked Hypophosphatemic Mice," J Clin Invest 99(6): 1200-1209 (1997), Eicher et al., "Hypophosphatemia: Mouse Model for Human Familial Hypophosphatemic (Vitamin D-resistant) Rickets," Proc Natl Acad Sci USA 73(12):4667-4671 (1996), Strom et al., "Pex Gene Deletions in Gy and Hyp Mice Provide Mouse Models for X-linked Hypophosphatemia," Hum Mol Genet 6(2):165-171 (1997), which are hereby incorporated by reference in their entirety). The animals were fed a complete, fixed formula diet containing 0.94% phosphate. Anesthetized rats (220-250 g body weight) were administered IV either FGF23$^{28-251}$ (0.1 µg kg body weight$^{-1}$) or FGF23$^{180-251}$ (0.1 µg kg body weight$^{-1}$) or vehicle. Before and 3 h after the injection, blood was drawn from the carotid artery and urine was collected through bladder catheterization. Plasma and urine chemistry of animals were analyzed using Vitros Chemistry Analyzer (Ortho-Clinical Diagnosis). 10- to 15-week old Hyp mice were fasted for 8-12 h before administering IP either FGF23$^{180-251}$ (1 mg) or FGF23$^{180-205}$ (860 µg) or vehicle. Before and 2 h, 4 h, 8 h, and 24 h after the injection, urine and serum samples were collected. Phosphate concentrations in urine and serum were determined using Phosphorus Liqui-UV Test (Stanbio Laboratory), and urine creatinine levels were measured using DetectX™ Urinary Creatinine Detection Kit (LuminosAssays).

Analysis of NaP$_i$-2A and NaP$_i$-2C Protein Abundance in the Apical Brush Border Membrane of Renal Proximal Tubule Epithelium Immunoblot analysis of NaP$_i$-2A and NaP$_i$-2C protein abundance in renal cortex tissue and isolated brush border membrane vesicles (BBMV), and NaP$_i$-2A immunostaining of renal tissue were performed as described (Bacic et al., "Activation of Dopamine D1-like Receptors Induces Acute Internalization of the Renal Na$^+$/phosphate Cotransporter NaPi-IIa in Mouse Kidney and OK cells," Am J Physiol Renal Physiol 288(4):F740-747 (2005), Loffing et al., "Renal Na/H Exchanger NHE-3 and Na—PO$_4$ Cotransporter NaP$_i$-2 Protein Expression in Glucocorticoid Excess and Deficient States," J Am Soc Nephrol 9(9):1560-1567 (1998), Moe et al., "Dietary NaCl Modulates Na(+)-H+ Antiporter Activity in Renal Cortical Apical Membrane Vesicles," Am J Physiol 260(1 Pt 2):F130-137 (1991), which are hereby incorporated by reference in their entirety).

For immunoblot, rat kidney cortices were dissected and homogenized, and BBMV were isolated (Loffing et al., "Renal Na/H Exchanger NHE-3 and Na—PO$_4$ Cotransporter NaP$_i$-2 Protein Expression in Glucocorticoid Excess and Deficient States," J Am Soc Nephrol 9(9):1560-1567 (1998), Moe et al., "Dietary NaCl Modulates Na(+)-H+ Antiporter Activity in Renal Cortical Apical Membrane Vesicles. Am J Physiol 260(1 Pt 2):F130-137 (1991), which are hereby incorporated by reference in their entirety). 30 µg of cortical/BBMV protein was solubilized in Laemmli sample buffer, fractionated by SDS-PAGE, transferred to PVDF membrane and labeled using polyclonal rabbit antibody for NaP$_i$-2A or -2C (kind gift from Drs. J. Biber and H. Murer, University of Zurich, Switzerland) (1:3,000 dilution) and monoclonal mouse antibody for β-actin (1:5,000 dilution). For immunohistochemistry, rat kidneys were fixed in situ with perfusion of 2.5% paraformaldehyde via distal aorta of renal arteries before nephrectomy. In some experiments, kidneys were harvested and directly frozen in Tissue TeK® OCT using liquid nitrogen, and cryosections (4 µm) were prepared and processed for immunofluorescent staining (Bacic et al., "Activation of Dopamine D1-like Receptors Induces Acute Internalization of the Renal Na$^+$/phosphate Cotransporter NaPi-IIa in Mouse Kidney and OK cells," Am J Physiol Renal Physiol 288(4):F740-747 (2005), which is hereby incorporated by reference in its entirety). Sections were incubated with polyclonal rabbit antibody for NaP$_i$-2A (1:300 dilution; kind gift from Dr. J. Biber) followed by secondary antibodies conjugated to rhodamine (Molecular Probes). For NaP$_i$-2A/β-actin double staining, the sections were then incubated with fluorescein isothiocyanate-phalloidin (1:50) (Molecular Probes) to stain β-actin filaments. Sections were visualized with a Zeiss LSM510 microscope.

Statistical Analysis

Data are expressed as the mean±SE (n≥6 or more). Statistical analysis was performed using Student's unpaired or paired t-test, or using analysis of variance (ANOVA) when applicable. A value of P≤0.05 was considered as statistically significant.

Example 1

Figure 1B:
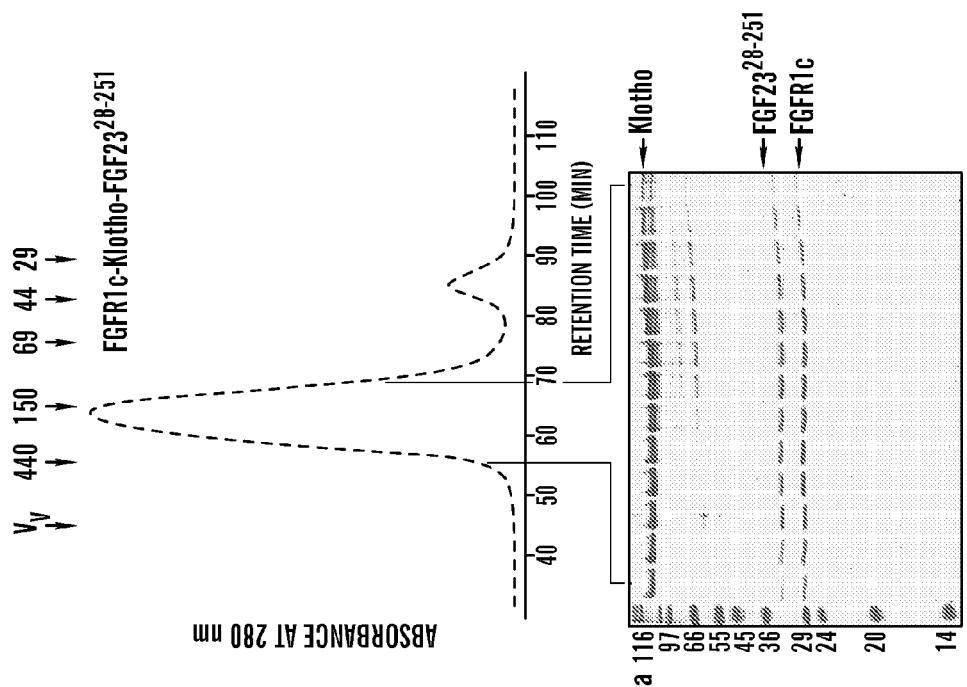
Figure 1C:
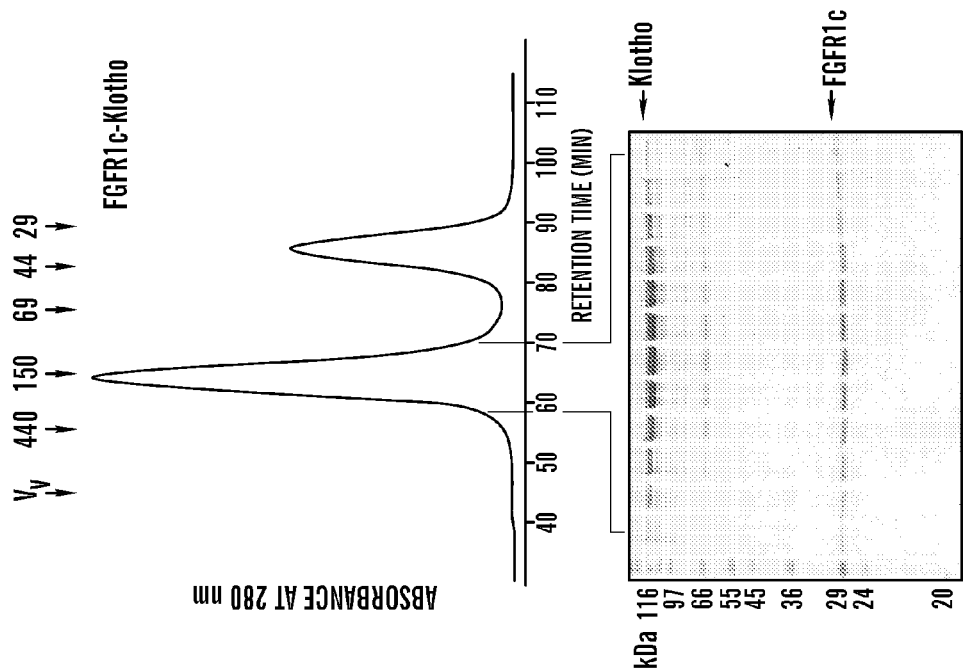

C-terminal Tail of FGF23 Mediates Binding of FGF23 to a de novo Site at the Composite FGFR1c-Klotho Interface To understand how FGF23, FGFR and Klotho interact to form a ternary complex, the ternary complex was reconstituted in solution using bioactive, full-length FGF23 (FGF23$^{28-251}$; FIG. 1A), and the soluble ectodomains of FGFR1c and Klotho. The binary complex of FGFR1c ectodomain with Klotho ectodomain was formed by capturing the Klotho ectodomain onto an FGFR1c affinity column from conditioned media of a HEK293 cell line ectopically expressing the Klotho ectodomain (Kurosu et al., "Regulation of Fibroblast Growth Factor-23 Signaling by Klotho," J Biol Chem 281(10):6120-6123 (2006), which is hereby incorporated by reference in its entirety). The FGFR1c-Klotho complex was further purified by size-exclusion chromatography to remove excess FGFR1c (FIG. 1B). Next, the FGFR1c-Klotho complex was mixed with FGF23$^{28-251}$, and ternary complex formation was examined by size-exclusion chromatography. As shown in FIG. 1C, FGF23 co-eluted with the FGFR1c-Klotho complex demonstrating that the ectodomains of FGFR1c and Klotho are sufficient to form a stable ternary complex with FGF23.

Figure 1D:
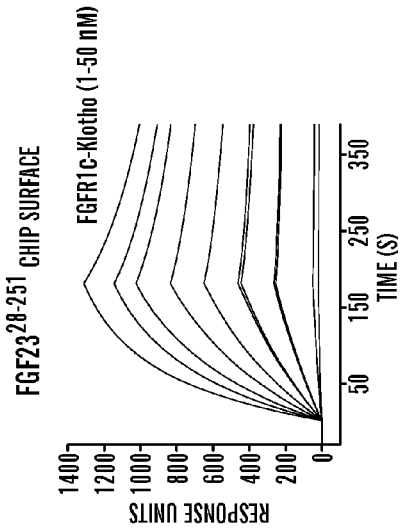
Figure 1E:
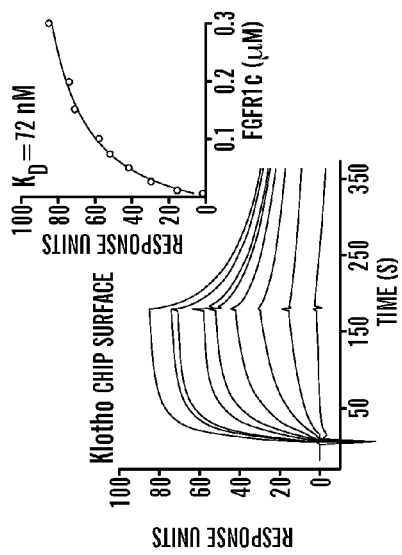
Figure 1F:
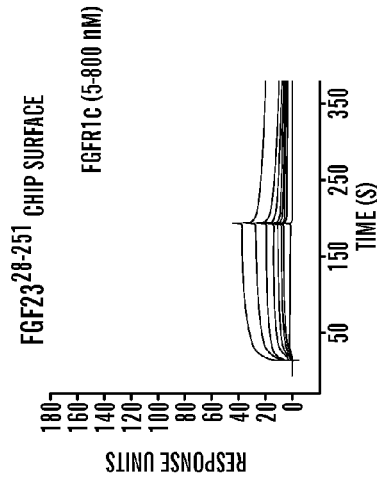

The size-exclusion data showing that Klotho and FGFR1c ectodomains form a stable binary complex (FIG. 1B) indicate that Klotho must harbor a high affinity binding site for FGFR1c. To further confirm this, surface plasmon resonance (SPR) spectroscopy was used to determine the dissociation constant of the FGFR1c-Klotho interaction. Klotho ectodomain was immobilized on a biosensor chip, and increasing concentrations FGFR1c ectodomain were passed over the chip. Consistent with the results obtained using size-exclusion chromatography (FIG. 1B), Klotho bound FGFR1c with high affinity ($K_D$=72 nM; FIG. 1D). Because Klotho harbors a high affinity binding site for FGFR1c, it was reasoned that Klotho might also possess a distinct high affinity binding site for FGF23, and promote FGF23-FGFR1c binding by engaging FGF23 and FGFR1c simultaneously. To test this, $FGF23^{28-251}$ was coupled to a biosensor chip, and increasing concentrations of Klotho ectodomain were passed over the chip. As shown in FIG. 1F, Klotho bound poorly to $FGF23^{28-251}$. These data demonstrate that the Klotho ectodomain contains a high affinity binding site for FGFR1c but not for FGF23.

Figure 1G:
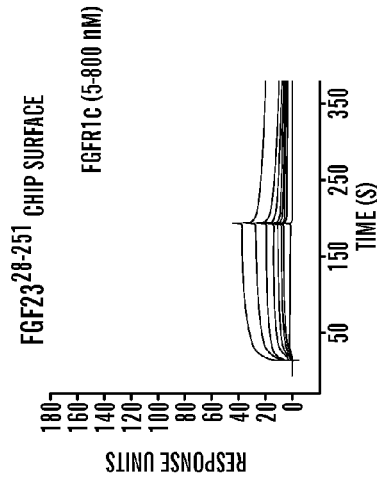

Next, binding of FGF23 to FGFR1c was measured by injecting increasing concentrations of FGFR1c over the FGF23 chip. As shown in FIG. 1G, $FGF23^{28-251}$ exhibited poor binding to FGFR1c. Thus, the SPR data show that FGF23 exhibits poor binding affinity for both the Klotho ectodomain alone and the FGFR1c ectodomain alone. Together with the size-exclusion chromatography data showing that FGF23 binds stably to the purified binary FGFR1c-Klotho complex, the data raised the question whether FGF23 binds to a de novo site generated at the composite FGFR1c-Klotho interface. To test this, FGFR1c-Klotho complex was purified as described above, and increasing concentrations of the binary complex were passed over the FGF23 chip. As shown in FIG. 1E, $FGF23^{28-251}$ bound to the FGFR1c-Klotho complex demonstrating that FGF23 interacts with a de novo site generated at the composite FGFR1c-Klotho interface.

Figure 2A:
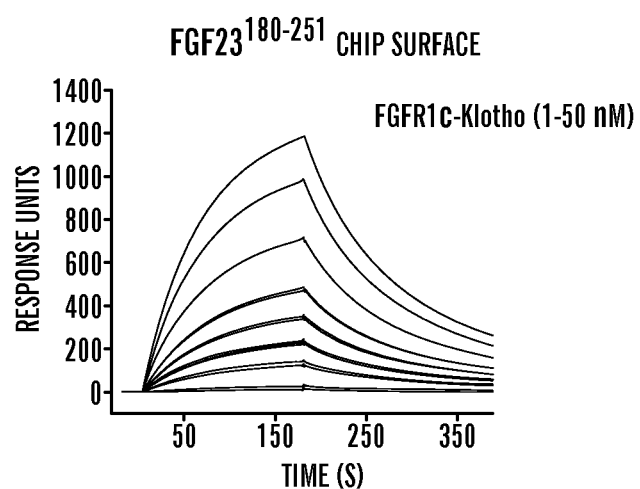

It was then examined whether the C-terminal tail of FGF23 mediates binding of FGF23 to the FGFR1c-Klotho complex. To test this, the C-terminal tail peptide of FGF23 ($FGF23^{180-251}$; FIG. 1A) was coupled to a biosensor chip and increasing concentrations of FGFR1c-Klotho complex were passed over the chip. As shown in FIG. 2A, $FGF23^{180-251}$ avidly bound to the binary complex. Size-exclusion chromatography and co-immunoprecipitation experiments yielded similar results supporting the SPR data (FIGS. 2B, C, and D).

Example 2

Figure 3B:
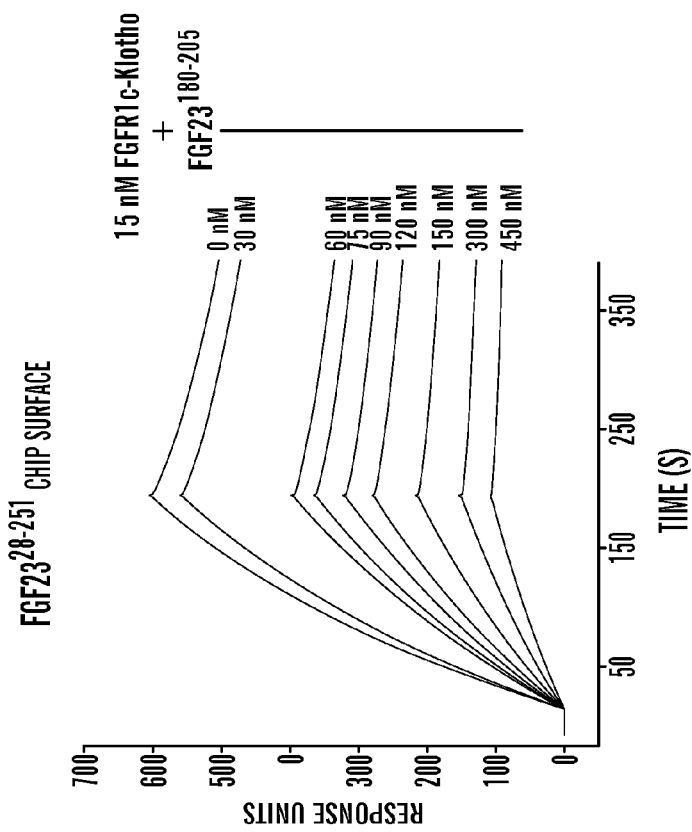
Figure 3A:
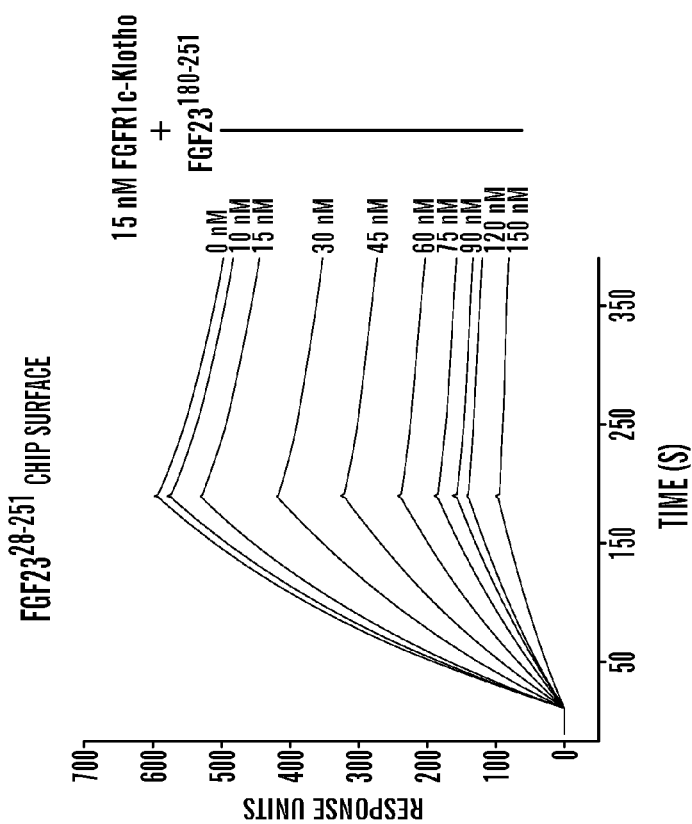
Figure 3F:
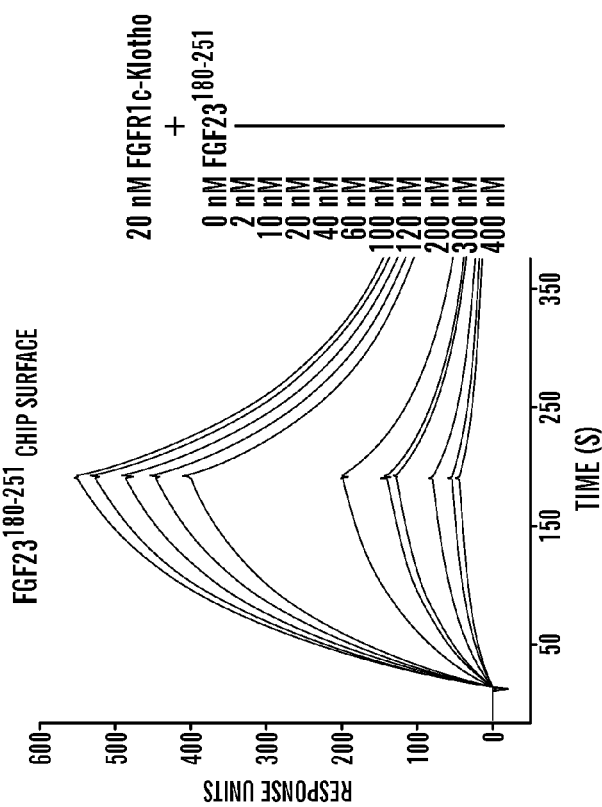
Figure 3E:
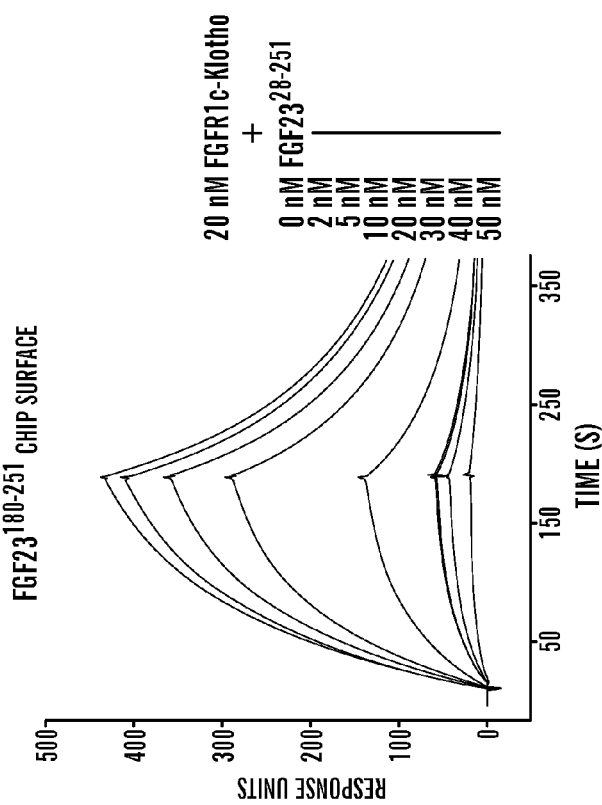
Figure 3G:
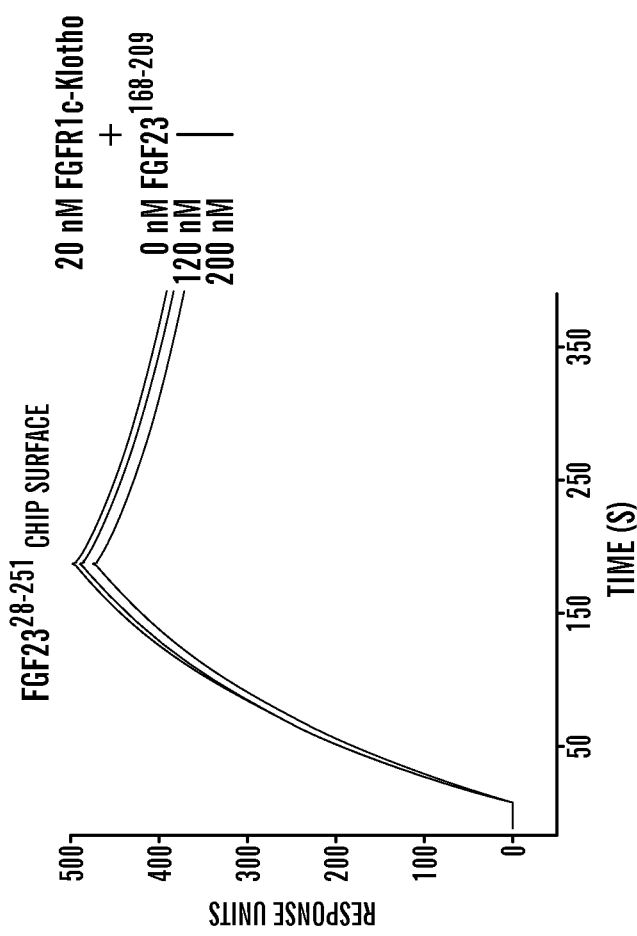
Figure 3H:
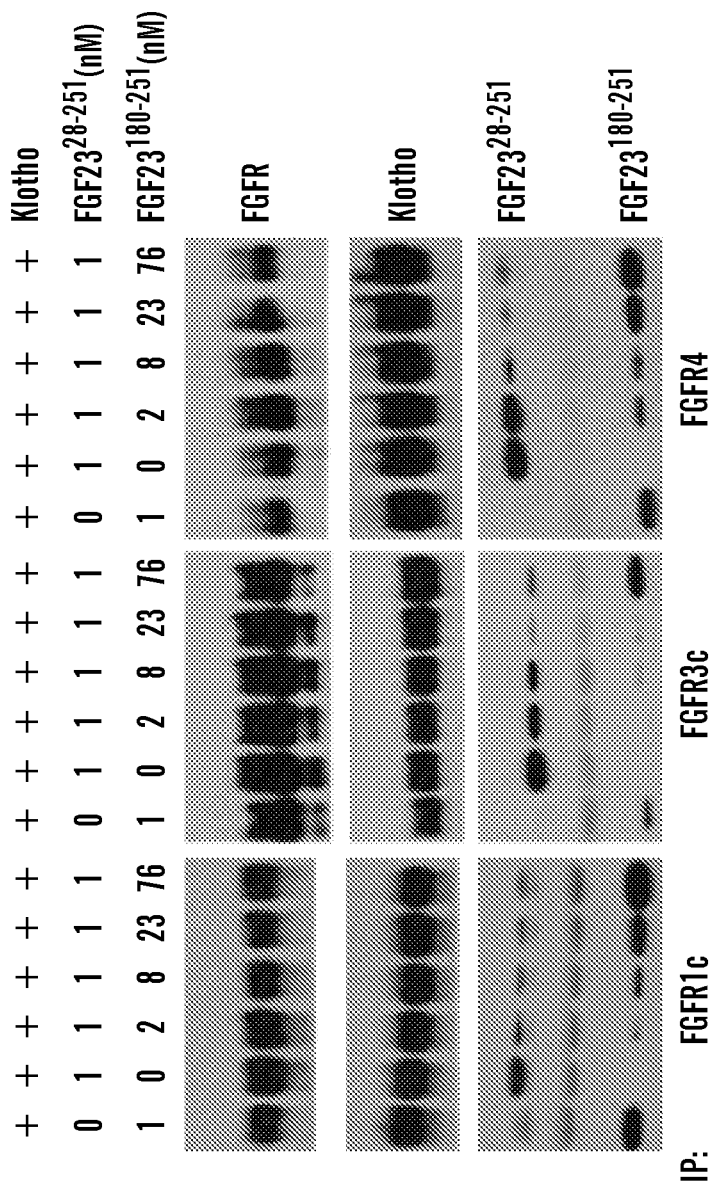
Figure 4D:
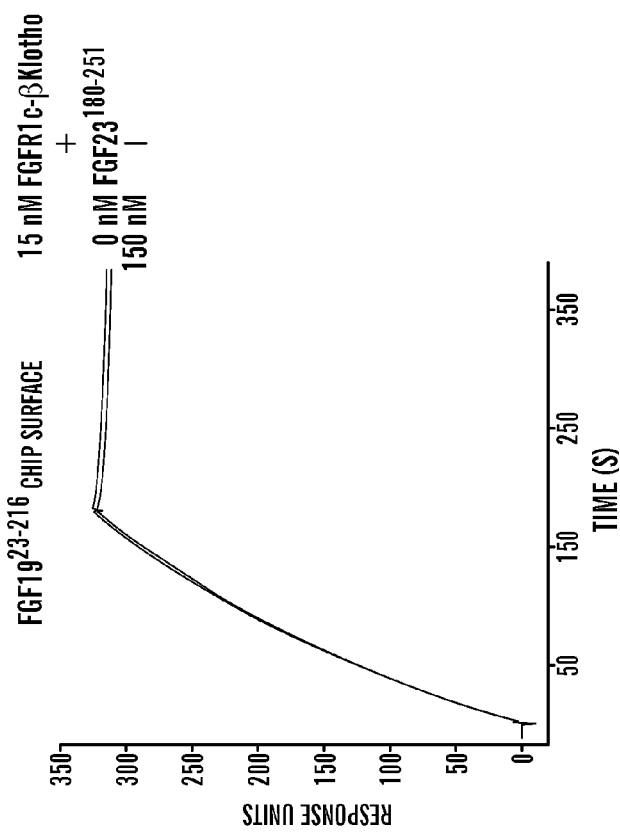
Figure 4C:
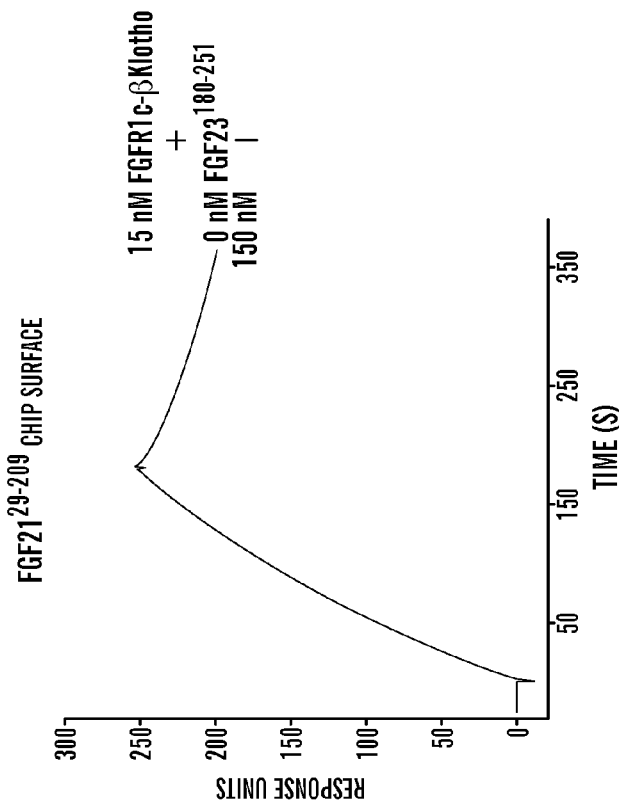

C-Terminal Tail of FGF23 Competes with Full-Length FGF23 for Binding to the Binary FGFR-Klotho Complex To fully nail down that the C-terminal tail of FGF23 mediates FGF23 binding to the binary FGFR1c-Klotho complex, a fixed concentration of FGFR1c-Klotho was mixed with increasing concentrations of $FGF23^{180-251}$, and the mixtures were passed over the FGF23 chip. Mixtures of $FGF23^{28-251}$ with FGFR1c-Klotho were used as a control. As shown in FIGS. 3A and D, $FGF23^{180-251}$ competed, in a dose-dependent fashion, with $FGF23^{28-251}$ for binding to the FGFR1c-Klotho complex. Half-maximum inhibition of FGFR1c-Klotho binding to $FGF23^{28-251}$ was reached with a 3.3-fold molar excess of $FGF23^{180-251}$ over FGFR1c-Klotho complex (FIG. 3D). As expected, less than an equimolar amount of $FGF23^{28-251}$ relative to FGFR1c-Klotho complex already yielded 50% inhibition of binding of the binary complex to immobilized $FGF23^{28-251}$ (FIGS. 3C and D). Similar results were obtained using the "reverse" SPR assay format, where $FGF23^{180-251}$ was immobilized on a chip and mixtures of a fixed concentration of FGFR1c-Klotho complex with increasing concentrations of $FGF23^{28-251}$ were passed over the chip (FIG. 3E). Mixtures of $FGF23^{180-251}$ with FGFR1c-Klotho were used as a control (FIG. 3F). To verify the specificity of the interaction between the FGF23 C-terminal tail and the FGFR1c-Klotho complex, the C-terminal tail peptide of FGF21 and FGFR1c-Klotho were mixed at molar ratios of 6:1 and 10:1, and the mixtures were injected over a FGF23 chip. As shown in FIG. 3G, $FGF21^{168-209}$ failed to inhibit binding of the FGFR1c-Klotho complex to immobilized $FGF23^{28-251}$. In addition, the ability of the FGF23 C-terminal tail peptide to interfere with binary complex formation between βKlotho and either FGF19 or FGF21 was tested, as was its ability to interfere with ternary complex formation between βKlotho, FGFR, and either FGF19 or FGF21. $FGF19^{23-216}$ and $FGF21^{29-209}$ were coupled to a biosensor chip, and a 2:1 mixture of $FGF23^{180-251}$ and βKlotho ectodomain was injected over the chip. As shown in FIGS. 4A and B, $FGF23^{180-251}$ failed to inhibit binding of βKlotho to immobilized FGF19 or FGF21. Likewise, a 10-fold molar excess of $FGF23^{180-251}$ over FGFR1c-βKlotho did not affect binding of the FGFR1c-βKlotho complex to immobilized FGF19 or FGF21 (FIGS. 4C and D). A co-immunoprecipitation based competition assay also confirmed that the C-terminal tail peptide of FGF23 can inhibit binding of FGF23 to its binary cognate FGFR-Klotho complex (FIG. 3H). Together, the data unambiguously demonstrate that the C-terminal tail of FGF23 harbors the binding site for the binary FGFR-Klotho complex and hence is essential for formation of the ternary FGF23-FGFR-Klotho complex. Importantly, the binding data unveil that proteolytic cleavage at the $^{176}$RXXR$^{179}$ motif (SEQ ID NO:1) abrogates FGF23 activity by removing the binding site for the binary FGFR-Klotho complex that resides in the C-terminal tail of FGF23.

Example 3

Figure 2D:
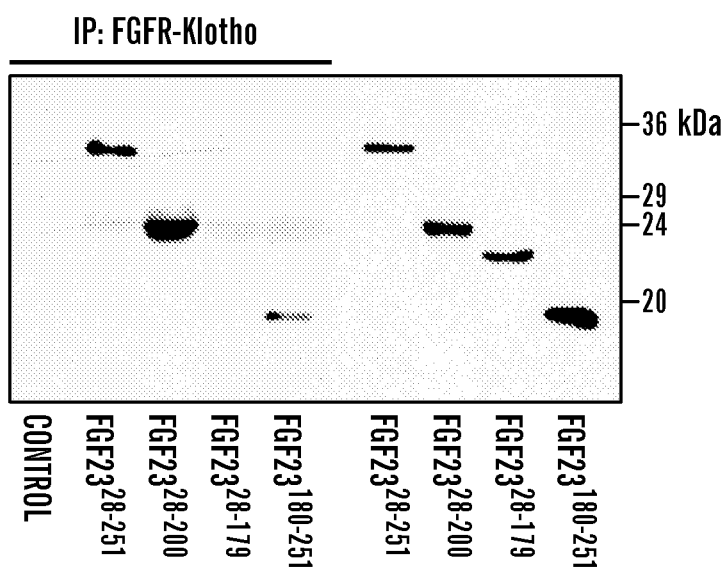
Figure 5A:
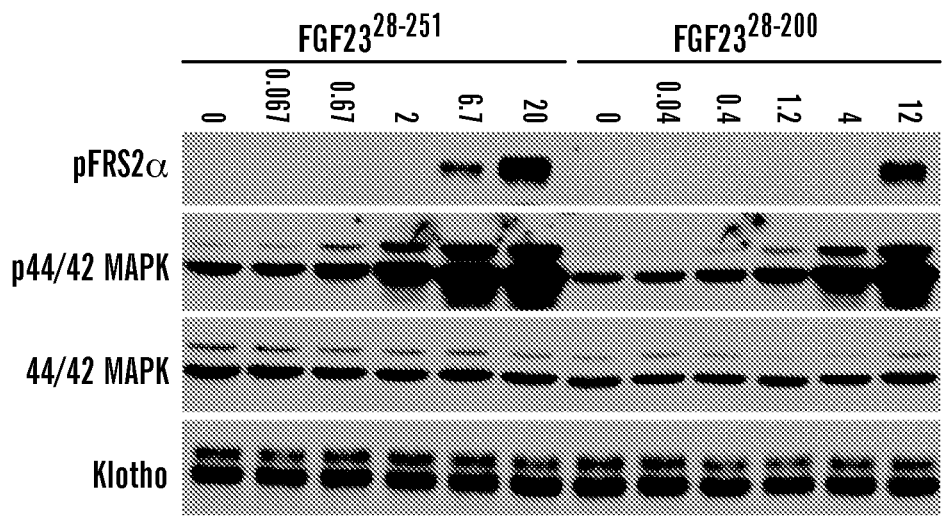
FIGS. 5A-C show that residues S180 to T200 of the C-terminal tail of FGF23 comprise the minimal binding epitope for the FGFR-Klotho complex.
Figure 5B:
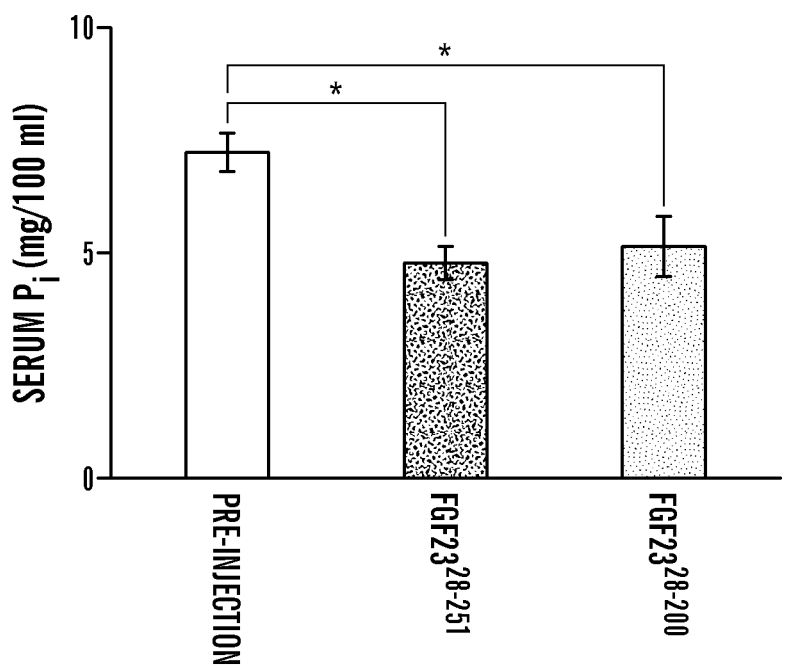
Figure 5C:
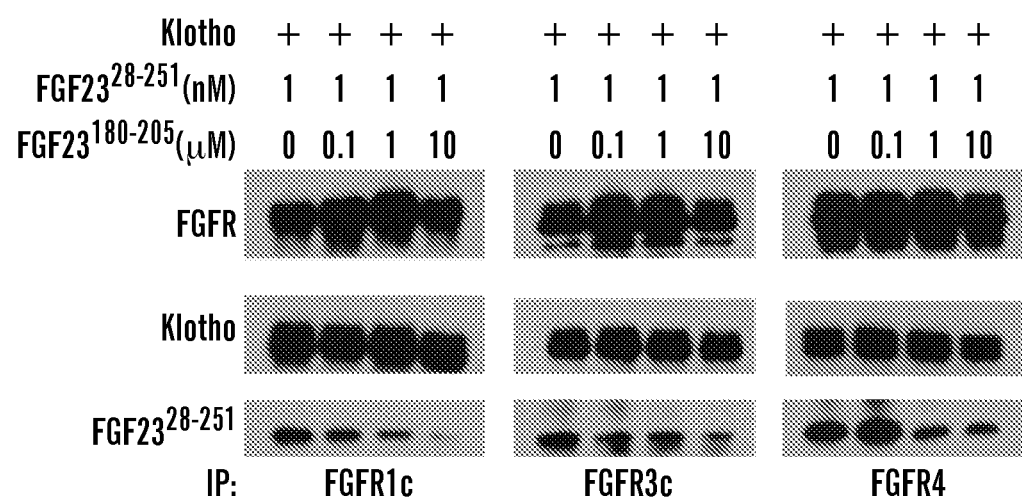

Residues S180 to T200 of the C-Terminal Tail of FGF23 Comprise the Minimal Binding Epitope for the FGFR-Klotho Complex In follow-up studies, it was found that $FGF23^{28-200}$, which lacks the last 51 C-terminal amino acids, still retains the ability to co-immunoprecipitate with the binary FGFR-Klotho complex (FIG. 2D). The finding suggested that $FGF23^{28-200}$ may have similar biological activity as the full-length protein. To test this, the ability of $FGF23^{28-200}$ and $FGF23^{28-251}$ to induce tyrosine phosphorylation of FGF receptor substrate 2α (FRS2α) and downstream activation of MAP kinase cascade in Klotho-expressing cultured cells, and to induce phosphaturia in mice, was examined. As shown in FIG. 5A, $FGF23^{28-200}$ induced phosphorylation of FRS2α and downstream activation of MAP kinase cascade at a dose comparable to that of $FGF23^{28-251}$. The truncated FGF23 was also nearly as effective as the full-length ligand in reducing serum phosphate concentration in healthy C57BL/6 mice (FIG. 5B). These data show that deletion of the last 51 amino acids from the FGF23 C-terminus has little effect on FGF23 biological activity, narrowing down the epitope on the FGF23 C-terminal tail for the composite FGFR-Klotho interface to residues S180 and T200. Indeed, a FGF23 peptide comprising the minimal binding epitope for FGFR-Klotho ($FGF23^{180-205}$; FIG. 1A) was able to compete, in a dose-dependent fashion, with $FGF23^{28-251}$ for binding to the binary FGFR1c-Klotho complex (FIG. 3B). Half-maximum inhibition of FGFR1c-Klotho binding to $FGF23^{28-251}$ was reached with a 5.7-fold molar excess of $FGF23^{180-205}$ over FGFR1c-Klotho complex (FIG. 3D). Similarly, in a co-immunoprecipitation based competition assay, the FGF23$^{180\text{-}205}$ peptide was able to inhibit binding of FGF23 to the binary complexes of its cognate FGFR and Klotho (FIG. 5C). The data also explain the finding by Garringer and colleagues showing that residues P189 to P203 are required for FGF23 signaling (Garringer et al., "Molecular genetic and biochemical analyses of FGF23 mutations in familial tumoral calcinosis," *Am J Physiol Endocrinol Metab* 295(4):E929-937 (2008), which is hereby incorporated by reference in its entirety).

Example 4

FGF23 C-Terminal Peptides Block FGF23 Signaling

Figure 6A:
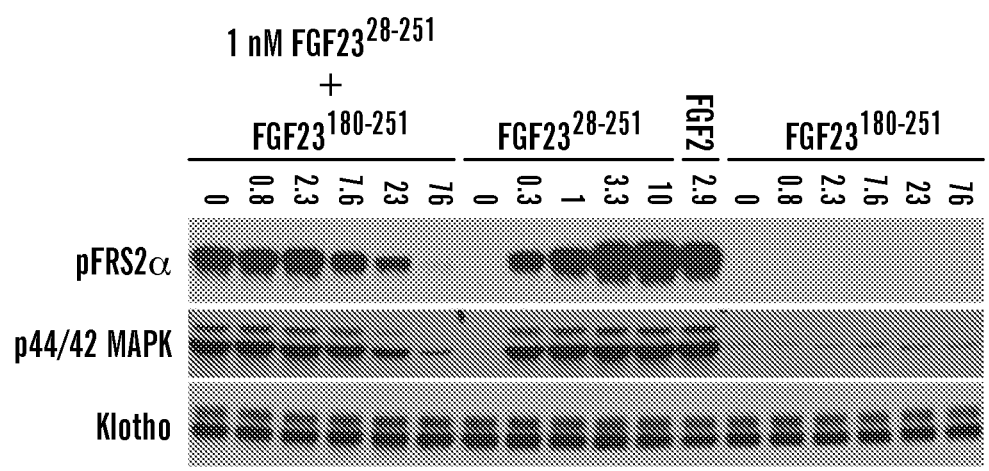
FIGS. 6A-C show that FGF23 C-terminal peptides impair ternary complex formation between FGF23, Klotho, and FGFR, and specifically block FGF23 signaling.
Figure 6B:
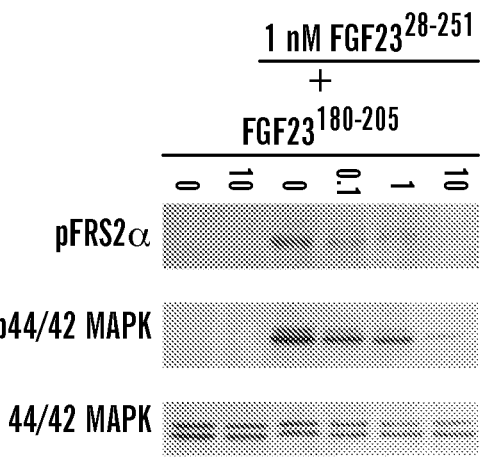

Based on these data, it was postulated that FGF23$^{180\text{-}251}$ and FGF23$^{180\text{-}205}$ should antagonize FGF23 signaling by competing with full-length FGF23 for binding to the FGFR-Klotho complex. To test this, cells stably overexpressing Klotho were stimulated with FGF23$^{28\text{-}251}$ alone or FGF23$^{28\text{-}251}$ mixed with increasing concentrations of either FGF23$^{180\text{-}251}$ or FGF23$^{180\text{-}205}$. As shown in FIGS. 6A and B, both peptides inhibited, in a dose-dependent fashion, FGF23-induced tyrosine phosphorylation of FRS2α and downstream activation of MAP kinase cascade.

Figure 6C:
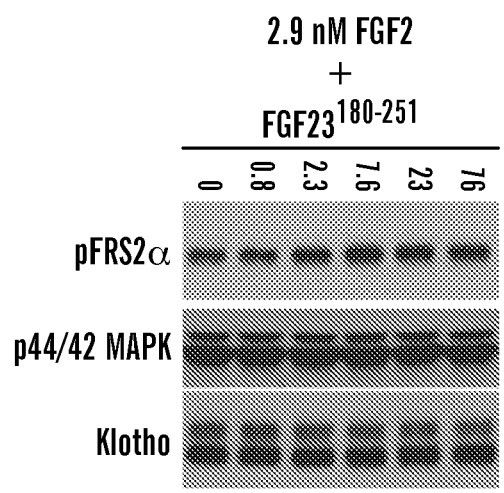

To test the specificity of the FGF23 antagonists, the ability of the FGF23$^{180\text{-}251}$ peptide to inhibit signaling of FGF2, a prototypical paracrine-acting FGF, which does not require Klotho for signaling was examined. As shown in FIG. 6C, the FGF23 antagonist failed to inhibit tyrosine phosphorylation of FRS2α and downstream activation of MAP kinase cascade induced by FGF2. These data show that FGF23 C-terminal peptides specifically block FGF23 signaling.

Example 5

Figure 7A:
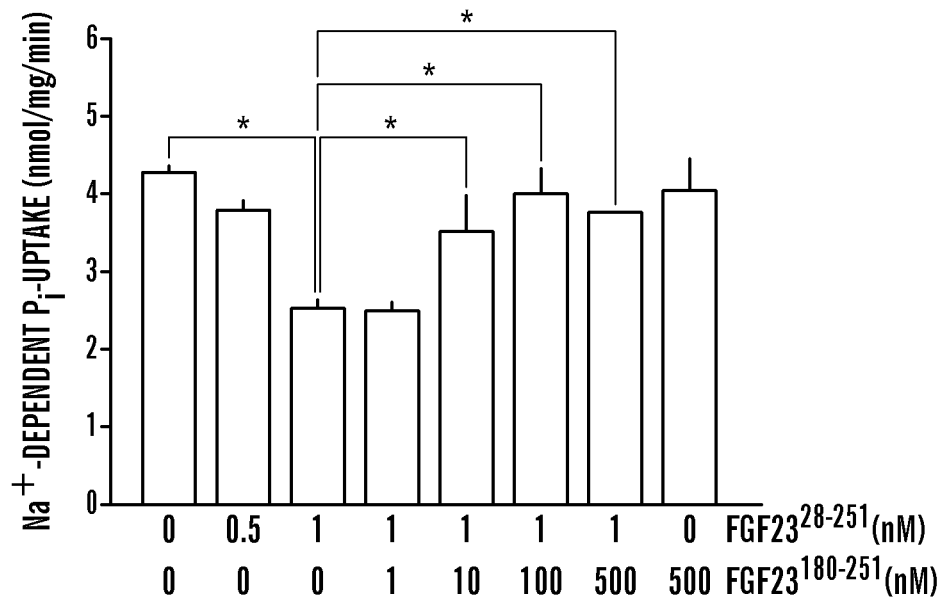
FIGS. 7A-B show that FGF23 C-terminal peptides antagonize the inhibitory effect of FGF23 on sodium-coupled phosphate uptake. Opossum kidney OKP cells were stimulated with either FGF23$^{28-251}$ or FGF23$^{180-251}$ or FGF23$^{180-205}$ alone, or mixtures of FGF23$^{28-251}$ with either increasing FGF23$^{180-251}$ (FIG. 7A) or increasing FGF23$^{180-205}$ (FIG. 7B). After 4 h cell stimulation, sodium-dependent phosphate uptake was measured. Bars and error bars denote mean+SE. An asterisk indicates P<0.05 by ANOVA.
Figure 7B:
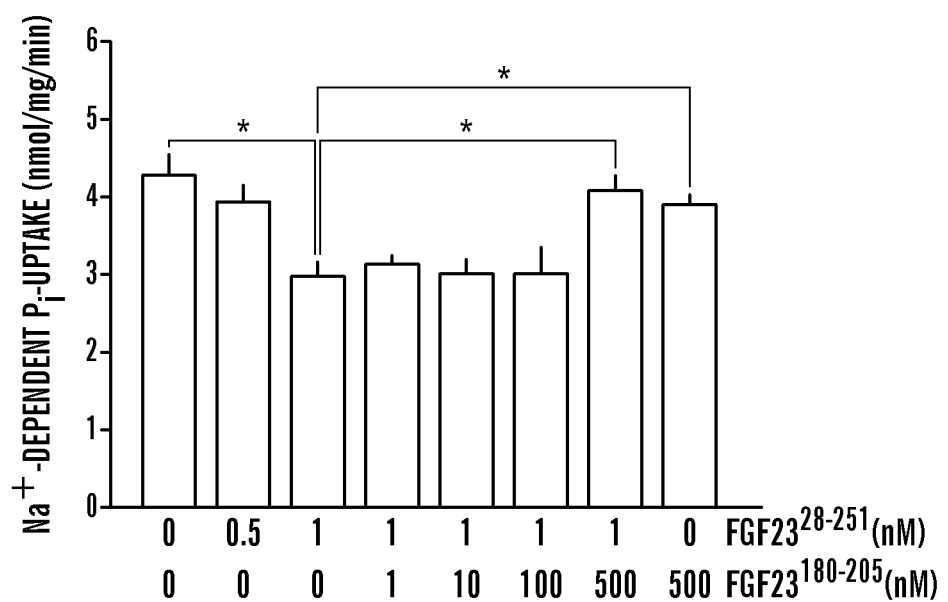

FGF23 C-Terminal Peptides Antagonize the Inhibitory Effect of FGF23 on Sodium-Coupled Phosphate Uptake by Renal Proximal Tubule Epithelial Cells In renal proximal tubule epithelium, FGF23 signaling leads to inhibition of phosphate uptake. To establish further that FGF23 C-terminal peptides block FGF23 action, the effects of the peptides on sodium-coupled phosphate uptake in a proximal tubular cell model were studied. As shown in FIG. 7A, FGF23$^{180\text{-}251}$ antagonized the inhibition of phosphate uptake by FGF23$^{28\text{-}251}$ in a dose-dependent fashion, with an IC$_{50}$ of about 21 nM. FGF23$^{180\text{-}205}$ exhibited a similar, albeit less potent antagonistic effect (FIG. 7B). As expected, neither of the two FGF23 C-terminal peptides altered phosphate uptake when applied alone (FIGS. 7A and B).

Example 6

Figure 8:
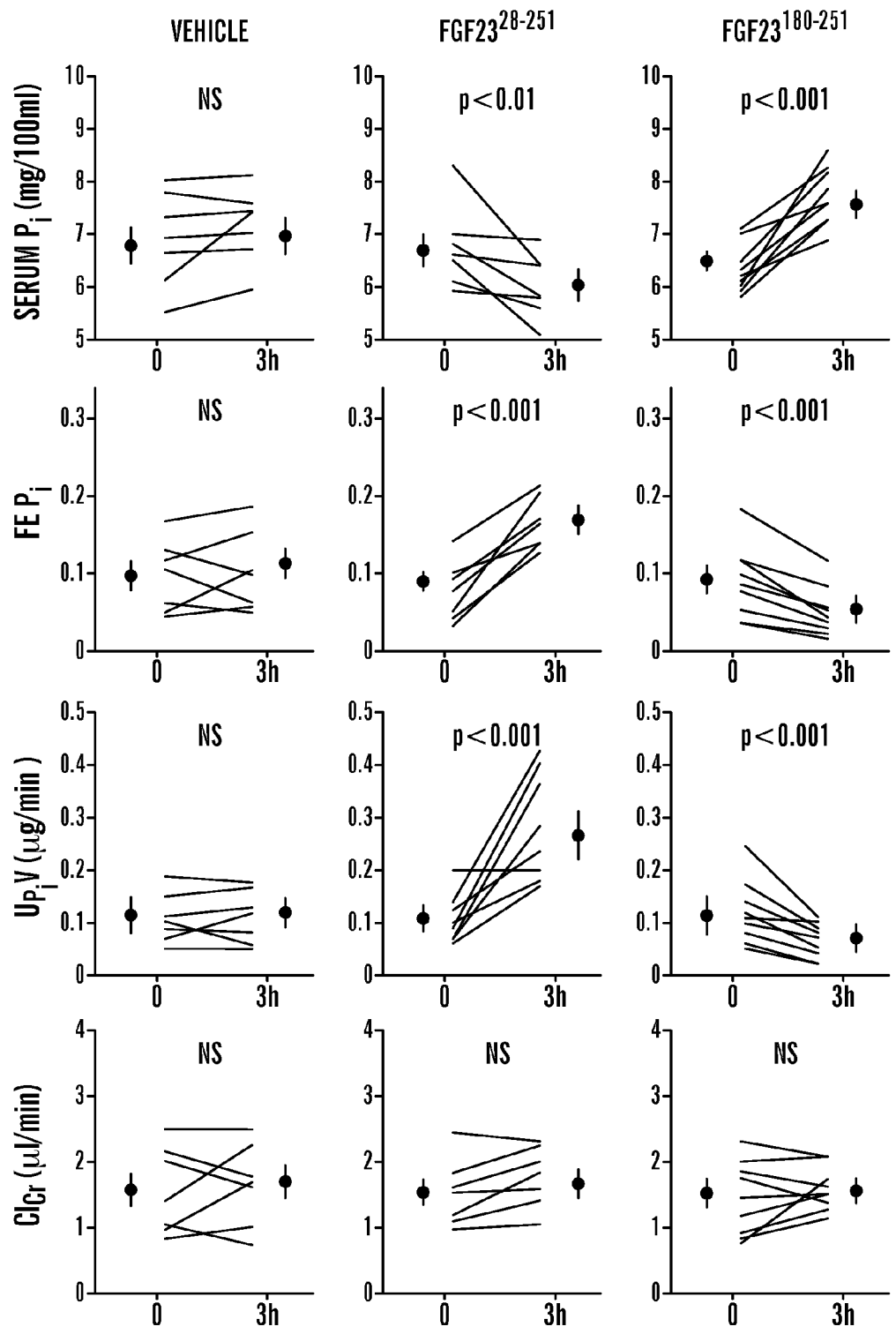
FIG. 8 shows that the FGF23 C-terminal tail peptide antagonizes phosphaturic activity of FGF23 in vivo. FGF23$^{28-251}$ (0.1 µg kg body weight$^{-1}$) or FGF23$^{180-251}$ (0.1 µg kg body weight$^{-1}$) were injected IV into Sprague-Dawley rats. Serum and urine parameters were measured and calculated before and 3 h after injection. FE $P_i$: fractional excretion of phosphate; $U_{Pi}V$: phosphate excretion rate; $Cl_{Cr}$: creatinine clearance.

FGF23 C-Terminal Peptides Antagonize Phosphaturic Activity of FGF23 in Healthy Rats These findings led to in vivo studies and an investigation of whether the FGF23 C-terminal peptides antagonize the phosphaturic effects of endogenous FGF23. An IV injection of FGF23$^{180\text{-}251}$ into healthy Sprague-Dawley rats led to renal phosphate retention, and hyperphosphatemia (FIG. 8), suggesting that FGF23 C-terminal peptides antagonize the phosphaturic action of endogenous FGF23. As expected, injection of FGF23$^{28\text{-}251}$ induced increases in excretion rate and fractional excretion of phosphate, and led to a significant decrease in plasma phosphate compared to vehicle-treated animals (FIG. 8).

Figure 9A:
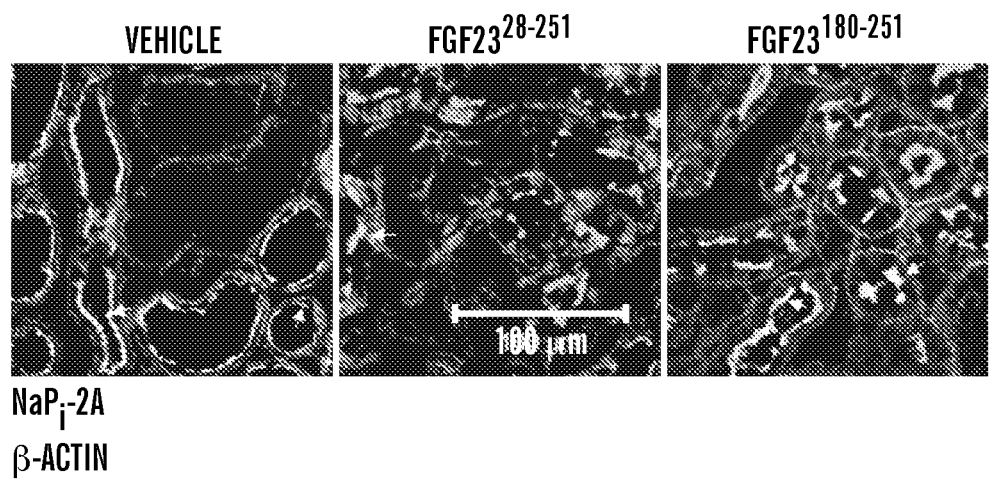
FIGS. 9A-C show that the FGF23 C-terminal tail peptide inhibits the ability of FGF23 to down-regulate the expression of the type II sodium-coupled phosphate transporters NaP$_i$-2A and NaP$_i$-2C in the apical brush border membrane. Sprague-Dawley rats were given IV FGF23$^{28-251}$(0.1 µg kg body weight$^{-1}$), FGF23$^{180-251}$ (0.1 µg kg body weight$^{-1}$), or vehicle, and renal tissue was isolated 3 h post injection.
Figure 9B:
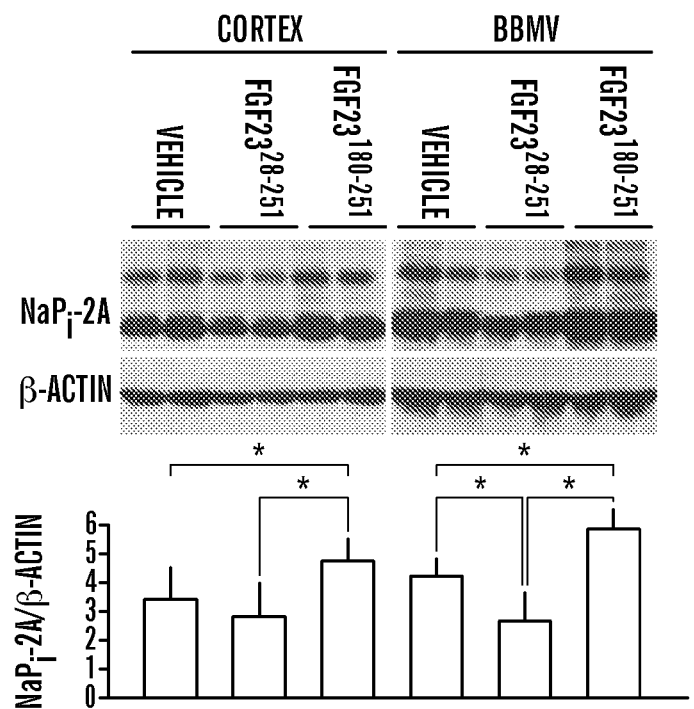
Figure 9C:
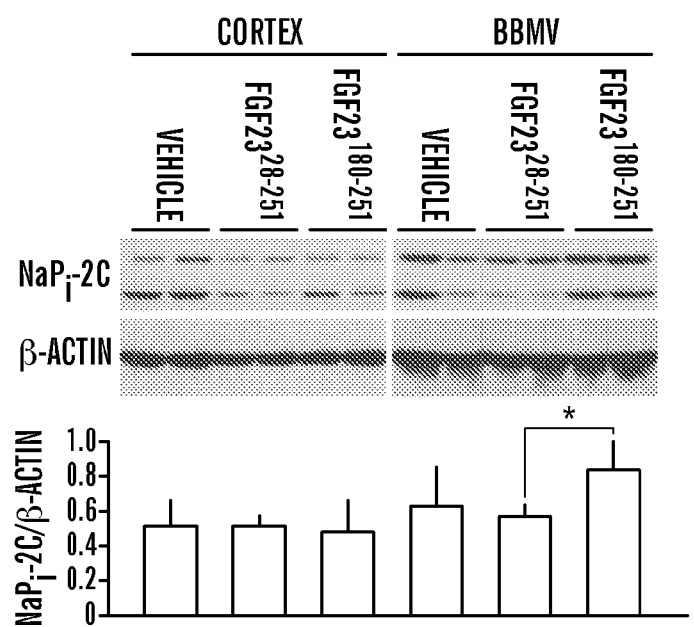

FGF23 exerts its phosphaturic activity by inhibiting phosphate uptake by renal proximal tubule epithelium. The effect has been attributed to reduced transport activity of NaP$_i$-2A and NaP$_i$-2C, reduced amount of NaP$_i$-2A and NaP$_i$-2C proteins in the apical brush border membrane, and at the more chronic level, repression of the NaP$_i$-2A and NaP$_i$-2C genes (Baum et al., "Effect of Fibroblast Growth Factor-23 on Phosphate Transport in Proximal Tubules," *Kidney Int* 68(3):1148-1153 (2005), Perwad et al., "Fibroblast Growth Factor 23 Impairs Phosphorus and Vitamin D Metabolism In Vivo and Suppresses 25-hydroxyvitamin D-1alpha-hydroxylase Expression In Vitro," *Am J Physiol Renal Physiol* 293(5): F1577-1583 (2007), Yamashita et al., "Fibroblast Growth Factor (FGF)-23 Inhibits Renal Phosphate Reabsorption by Activation of the Mitogen-activated Protein Kinase Pathway," *J Biol Chem* 277(31):28265-28270 (2002), Larsson et al., "Transgenic mice expressing fibroblast growth factor 23 under the control of the alpha1(I) collagen promoter exhibit growth retardation, osteomalacia, and disturbed phosphate homeostasis," *Endocrinology* 145(7):3087-3094 (2004), Segawa et al., "Effect of hydrolysis-resistant FGF23-R179Q on dietary phosphate regulation of the renal type-II Na/Pi transporter," *Pflugers Arch* 446(5):585-592 (2003), which are hereby incorporated by reference in their entirety). The abundance of NaP$_i$-2A protein in brush border membrane vesicles isolated from the kidneys of rats was examined. An IV injection of FGF23$^{180\text{-}251}$ into healthy rats led to an increase in NaP$_i$-2A protein expression in the apical brush border membrane compared to vehicle treatment (FIGS. 9A and B). The peptide exhibited similar effects on the NaP$_i$-2C protein (FIG. 9C). As expected, injection of FGF23$^{28\text{-}251}$ led to a decrease in NaP$_i$-2A protein expression (FIGS. 9A and B). These findings establish that FGF23 C-terminal peptides counteract or cancel out FGF23's phosphaturic action mediated through NaP$_i$-2A and NaP$_i$-2C.

Example 7

Figure 10:
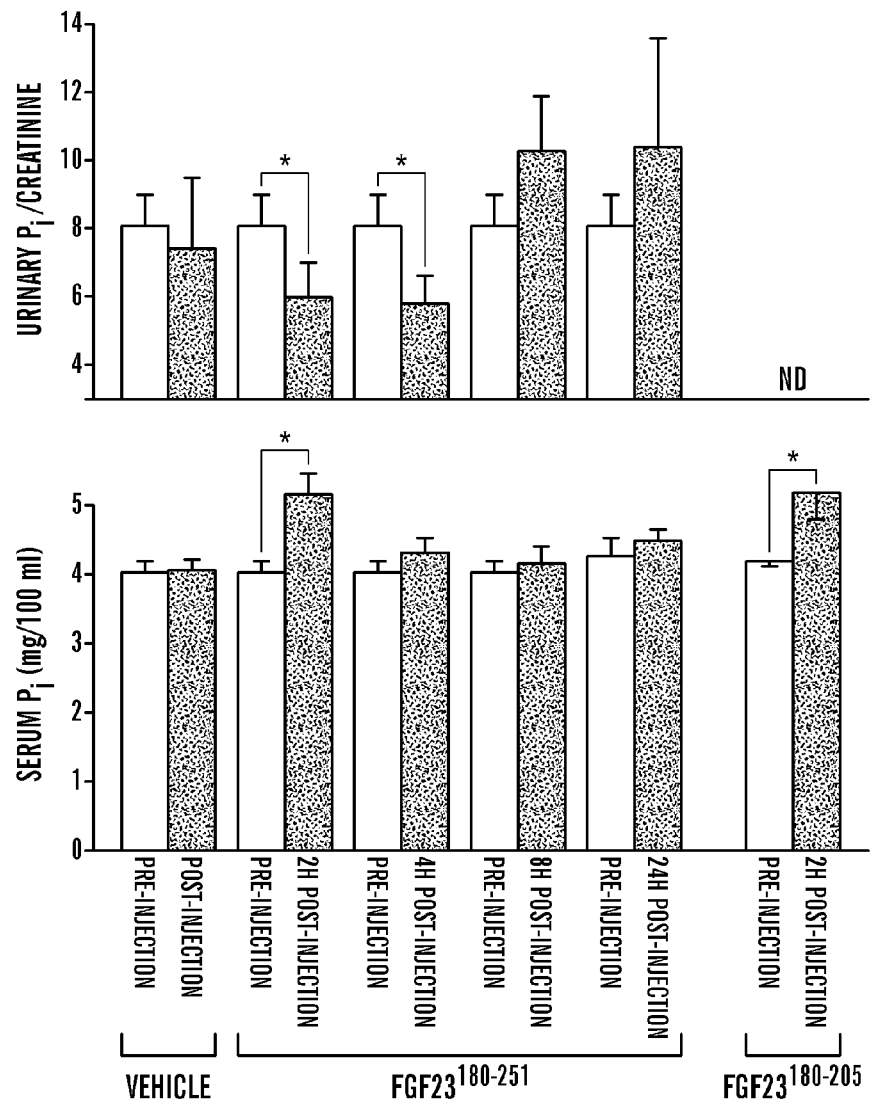
FIG. 10 shows that FGF23 C-terminal peptides alleviate renal phosphate wasting in Hyp mice. FGF23$^{180-251}$ (1 mg), FGF23$^{180-205}$ (860 µg), or vehicle were injected IP into Hyp mice. Urine phosphate (urinary $P_i$) and creatinine levels and serum phosphate levels (serum $P_i$) were measured before and at the indicated time points after the injection. Urinary $P_i$ of Hyp mice treated with FGF23$^{180-205}$ was not determined (ND). Bars and error bars are mean+SE. An asterisk denotes P<0.05 by ANOVA, two asterisks denote P<0.01.

FGF23 C-Terminal Peptides Antagonize Phosphaturic Activity of FGF23 in a Mouse Model of Renal Phosphate Wasting To evaluate the therapeutic potential of FGF23$^{180\text{-}251}$ for treating renal phosphate wasting, the peptide's efficacy in Hyp mice, a mouse model of XLH (Anonymous., "A Gene (PEX) with Homologies to Endopeptidases is Mutated in Patients with X-linked Hypophosphatemic Rickets. The HYP Consortium.," *Nat Genet* 11(2):130-136 (1995); Beck et al., "Pex/PEX Tissue Distribution and Evidence for a Deletion in the 3' Region of the Pex Gene in X-linked Hypophosphatemic Mice," *J Clin Invest* 99(6):1200-1209 (1997); Eicher et al., "Hypophosphatemia: Mouse Model for Human Familial Hypophosphatemic (Vitamin D-resistant) Rickets," *Proc Natl Acad Sci USA* 73(12):4667-4671 (1996); Strom et al., "Pex Gene Deletions in Gy and Hyp Mice Provide Mouse Models for X-linked Hypophosphatemia," *Hum Mol Genet* 6(2):165-171 (1997), which are hereby incorporated by reference in their entirety) was analyzed. XLH is an inherited phosphate wasting disorder associated with high FGF23, which is thought to be due to reduced clearance of FGF23 from the circulation. Excess FGF23 causes increased phosphate excretion resulting in hypophosphatemia. As shown in FIG. 10, an IP injection of FGF23$^{180\text{-}251}$ induced a decrease in renal phosphate excretion in Hyp mice compared to vehicle treatment. The effect persisted for at least four hours post injection. Concomitantly, serum phosphate levels were elevated by the FGF23 antagonist treatment (FIG. 10). Likewise, an IP injection of the FGF23[180-205] peptide, which comprises the minimal binding epitope for the composite FGFR-Klotho interface, caused an increase in serum phosphate in Hyp mice compared to vehicle-treated animals (FIG. 10). These results show that FGF23 C-terminal peptides are effective in attenuating renal phosphate wasting caused by excess FGF23.

In the present invention, it was demonstrated that the proteolytic cleavage at the RXXR (SEQ ID NO:1) motif downregulates FGF23 activity by a dual mechanism: by removing FGF23's binding site for the binary FGFR-Klotho complex, and by generating an endogenous inhibitor of FGF23. This regulatory mechanism was exploited to develop a FGF23 antagonist with therapeutic potential for hypophosphatemia associated with elevated or normal FGF23.

Patients with phosphate wasting disorders are generally treated symptomatically, with oral phosphate supplementation and 1,25-dihydroxyvitamin $D_3$/calcitriol. As alluded to in the background, oral phosphate therapy can be poorly tolerated, and in certain circumstances can induce hyperparathyroidism and poses risk of exacerbation of hypophosphatemia. In patients with XLH, the persistent and even exaggerated renal phosphate wasting during therapy can cause nephrocalcinosis and nephrolithiasis. For patients with renal phosphate wasting from tumor-induced osteomalacia, a causative treatment option exists, which is resection of the tumor producing excess amounts of phosphaturic hormone. These tumors are often difficult to locate, however, or the tumors are found in locations that are difficult to access, leaving most patients with tumor-induced osteomalacia also currently with no options other than symptomatic therapy (van Boekel et al., "Tumor Producing Fibroblast Growth Factor 23 Localized by Two-staged Venous Sampling," *Eur J Endocrinol* 158(3): 431-437 (2008); Jan de Beur S M., "Tumor-induced Osteomalacia," *JAMA* 294(10):1260-1267 (2005), which are hereby incorporated by reference in their entirety). Since excess FGF23 is the pathogenic factor in phosphate wasting disorders, blocking its action with FGF23 C-terminal peptides holds promise of providing the first causative pharmacotherapy.

In a mouse model of phosphate wasting disorders, it has been shown that FGF23 C-terminal peptides are effective in counteracting the phosphaturic action of FGF23. The present invention warrants further evaluation of the peptides' efficacy in nonhuman primates, and eventually, in humans. Neutralizing FGF23 activity with antibody provides an alternative approach for treating renal phosphate wasting. Indeed, Aono, Yamazaki and colleagues have explored this approach, and developed antibodies against FGF23 that effectively neutralize FGF23 activity in both healthy mice and Hyp mice (Yamazaki et al., "Anti-FGF23 Neutralizing Antibodies Show the Physiological Role and Structural Features of FGF23," *J Bone Miner Res* 23(9):1509-1518 (2008), Aono et al., "Therapeutic Effects of Anti-FGF23 Antibodies in Hypophosphatemic Rickets/Osteomalacia," *J Bone Miner Res*, published online May 5th, DOI 10.1359/jmbr.090509 (2009), which are hereby incorporated by reference in their entirety). While it has been conclusively demonstrated that the phosphaturic activity of FGF23 is Klotho-dependent (Nakatani et al., "Inactivation of klotho function induces hyperphosphatemia even in presence of high serum fibroblast growth factor 23 levels in a genetically engineered hypophosphatemic (Hyp) mouse model," *FASEB J* 23(11):3702-3711 (2009), which is hereby incorporated by reference in its entirety), the possibility that FGF23 may have some Klotho-independent functions has not yet been ruled out experimentally. In this regard, the present invention of an inhibitory peptide approach may offer a more targeted therapy for hypophosphatemia than anti-FGF23 antibodies as FGF23 C-terminal peptides specifically target the binary FGFR-Klotho complex and hence only neutralize Klotho-dependent function of FGF23. In contrast, the antibody approach does not discriminate between Klotho-dependent and -independent functions of FGF23. The FGF23 C-terminal peptides can also serve as an experimental tool to dissect Klotho-dependent and -independent functions of FGF23. The ability of the FGF23 C-terminal peptides to specifically recognize the binary receptor complex makes them a powerful tool to image tissues that express the cognate FGFR-Klotho complexes of FGF23.

Hypophosphatemia complicates a wide variety of conditions such as the refeeding syndrome, diabetic ketoacidosis, asthma exacerbations and chronic obstructive pulmonary disease, and recovery from organ (particularly, kidney) transplantation (Gaasbeek et al., "Hypophosphatemia: An Update on its Etiology and Treatment," *Am J Med* 118(10):1094-1101 (2005); Miller et al., "Hypophosphatemia in the Emergency Department Therapeutics," *Am J Emerg Med* 18(4): 457-461 (2000); Marinella M A., "Refeeding Syndrome and Hypophosphatemia," *J Intensive Care Med* 20(3):155-159 (2005), which are hereby incorporated by reference in their entirety). Indeed, hypophosphatemia complicating recovery from kidney transplantation, and parenteral iron therapy has been associated with increased plasma levels of FGF23 (Bhan et al., "Post-transplant hypophosphatemia: Tertiary 'Hyper-Phosphatoninism'?" *Kidney Int* 70(8):1486-1494 (2006), Evenepoel et al., "Tertiary 'Hyperphosphatoninism' accentuates hypophosphatemia and suppresses calcitriol levels in renal transplant recipients," *Am J Transplant* 7(5):1193-1200 (2007), Kawarazaki et al., "Persistent high level of fibroblast growth factor 23 as a cause of post-renal transplant hypophosphatemia," *Clin Exp Nephrol* 11(3):255-257 (2007), Trombetti et al., "FGF-23 and post-transplant hypophosphatemia: evidence for a causal link," abstract number Su168 presented at the 30th Annual Meeting of the American Society for Bone and Mineral Research (2008), Schouten et al., "FGF23 elevation and hypophosphatemia after intravenous iron polymaltose: a prospective study," *J Clin Endocrinol Metab* 94(7): 2332-2337 (2009), Shouten et al., "Iron polymaltose-induced FGF23 elevation complicated by hypophosphataemic osteomalacia," *Ann Clin Biochem* 46(2):167-169 (2009), Shimizu et al., "Hypophosphatemia induced by intravenous administration of saccharated ferric oxide: another form of FGF23-related hypophosphatemia," *Bone* 45(4):814-816 (2009), which are hereby incorporated by reference in their entirety). Thus, the FGF23 antagonist discovered in the present invention may be of therapeutic value for a much broader collection of patients than phosphate wasting disorders alone. The ability of FGF23 C-terminal peptides to enhance renal phosphate retention in normal rats ushers in the option of using these peptides therapeutically in hypophosphatemic conditions where FGF23 is not the primary cause of hypophosphatemia, and not down-regulated as a compensatory mechanism.

Another indication for therapy with FGF23 C-terminal peptides, which would target still more patients than disorders complicated by hypophosphatemia, is chronic kidney disease, a condition with a growing incidence, currently affecting nearly 26 million people in the United States alone. Plasma levels of FGF23 increase as kidney function declines in patients with chronic kidney disease (CKD) (Larsson et al., "Circulating Concentration of FGF-23 Increases as Renal Function Declines in Patients with Chronic Kidney Disease, But Does Not Change in Response to Variation in Phosphate Intake in Healthy Volunteers," *Kidney Int* 64(6):2272-2279 (2003), which is hereby incorporated by reference in its entirety), likely as a compensatory response to enhanced phosphate retention, and top 1000-fold of normal levels in patients with end-stage CKD (Gutierrez et al., "Fibroblast Growth Factor 23 and Mortality Among Patients Undergoing Hemodialysis," *N Engl J Med* 359(6):584-592 (2008); Jean et al., "High Levels of Serum Fibroblast Growth Factor (FGF)-23 are Associated with Increased Mortality in Long Haemodialysis Patients," *Nephrol Dial Transplant* 24(9):2792-2796 (2009), which are hereby incorporated by reference in their entirety). The gradual increases in plasma FGF23 correlate with disease progression (Fliser et al., "Fibroblast Growth Factor 23 (FGF23) Predicts Progression of Chronic Kidney Disease: the Mild to Moderate Kidney Disease (MMKD) Study," *J Am Soc Nephrol* 18(9):2600-2608 (2007); Westerberg et al., "Regulation of Fibroblast Growth Factor-23 in Chronic Kidney Disease," *Nephrol Dial Transplant* 22(11): 3202-3207 (2007), which are hereby incorporated by reference in their entirety), including suppression of 1,25-vitamin D production and development of secondary hyperparathyroidism (Nakanishi et al., "Serum Fibroblast Growth Factor-23 Levels Predict the Future Refractory Hyperparathyroidism in Dialysis Patients," *Kidney Int* 67(3):1171-1178 (2005); Shigematsu et al., "Possible Involvement of Circulating Fibroblast Growth Factor 23 in the Development of Secondary Hyperparathyroidism Associated with Renal Insufficiency," *Am J Kidney Dis* 44(2):250-256 (2004), which are hereby incorporated by reference in their entirety). Moreover, increased circulating FGF23 has emerged as an independent risk factor for cardiovascular disease and mortality in CKD (Gutierrez et al., "Fibroblast Growth Factor 23 and Mortality Among Patients Undergoing Hemodialysis," *N Engl J Med* 359(6):584-592 (2008); Jean et al., "High Levels of Serum Fibroblast Growth Factor (FGF)-23 are Associated with Increased Mortality in Long Haemodialysis Patients," *Nephrol Dial Transplant* 24(9):2792-2796 (2009); Gutierrez et al., "Fibroblast Growth Factor 23 and Left Ventricular Hypertrophy in Chronic Kidney Disease," *Circulation* 119(19):2545-2552 (2009); Mirza et al., "Circulating Fibroblast Growth Factor-23 is Associated with Vascular Dysfunction in the Community," *Atherosclerosis* 205(2):385-390 (2009); Mirza et al., "Serum Intact FGF23 Associate with Left Ventricular Mass, Hypertrophy and Geometry in an Elderly Population," *Atherosclerosis* 207(2):546-551 (2009); Nasrallah et al., "Fibroblast Growth Factor-23 (FGF-23) is Independently Correlated to Aortic Calcification in Haemodialysis Patients," *Nephrol Dial Transplant* 25(8):2679-2685 (2010), which are hereby incorporated by reference in their entirety), suggesting that FGF23 is implicated in the pathogenesis of CKD and its adverse outcomes. Blocking FGF23 action with FGF23 C-terminal peptides may prove effective in preventing or attenuating the occurrence of disease complications such as hyperparathyroidism and vascular calcification. Thus, the FGF23 antagonist of the present invention may be of therapeutic value for a much broader collection of patients than hypophosphatemia due to renal phosphate wasting alone.

The identification of the FGF23 C-terminal tail as a FGF23 antagonist suggests that proteolytic cleavage not only removes the binding site on FGF23 for the FGFR-Klotho complex, but also generates an endogenous FGF23 antagonist. A pathophysiological role of the latter mechanism is indicated by familial tumoral calcinosis (FTC), an autosomal recessive metabolic disorder with clinical manifestations opposing those of phosphate wasting disorders. Missense mutations in either the UDP-N-acetyl-α-D-galactosamine: polypeptide N-acetylglactosaminyltransferase 3 (GALNT3) gene (Garringer et al., "Two Novel GALNT3 Mutations in Familial Tumoral Calcinosis," *Am J Med Genet A* 143A(20): 2390-2396 (2007); Ichikawa et al., "Tumoral Calcinosis Presenting with Eyelid Calcifications Due to Novel Missense Mutations in the Glycosyl Transferase Domain of the GALNT3 Gene," *J Clin Endocrinol Metab* 91(11):4472-4475 (2006); Topaz et al., "Mutations in GALNT3, Encoding a Protein Involved in O-linked Glycosylation, Cause Familial Tumoral Calcinosis," *Nat Genet* 36(6):579-581 (2004); Dumitrescu et al., "A Case of Familial Tumoral Calcinosis/hyperostosis-hyperphosphatemia Syndrome Due to a Compound Heterozygous Mutation in GALNT3 Demonstrating New Phenotypic Features," *Osteoporos Int* (2008), which are hereby incorporated by reference in their entirety), or the FGF23 gene (Araya et al., "A Novel Mutation in Fibroblast Growth Factor 23 Gene as a Cause of Tumoral Calcinosis," *J Clin Endocrinol Metab* 90(10):5523-5527 (2005); Chefetz et al., "A Novel Homozygous Missense Mutation in FGF23 Causes Familial Tumoral Calcinosis Associated with Disseminated Visceral Calcification," *Hum Genet* 118(2):261-266 (2005); Larsson et al., "A Novel Recessive Mutation in Fibroblast Growth Factor-23 Causes Familial Tumoral Calcinosis," *J Clin Endocrinol Metab* 90(4):2424-2427 (2005); Benet-Pages et al., "An FGF23 Missense Mutation Causes Familial Tumoral Calcinosis with Hyperphosphatemia," *Hum Mol Genet* 14(3):385-390 (2005), which are hereby incorporated by reference in their entirety), have been associated with FTC. All FTC patients have abnormally high plasma levels of the C-terminal proteolytic fragment of FGF23 (Garringer et al., "Two Novel GALNT3 Mutations in Familial Tumoral Calcinosis," *Am J Med Genet A* 143A(20): 2390-2396 (2007); Ichikawa et al., "Tumoral Calcinosis Presenting with Eyelid Calcifications Due to Novel Missense Mutations in the Glycosyl Transferase Domain of the GALNT3 Gene," *J Clin Endocrinol Metab* 91(11):4472-4475 (2006); Topaz et al., "Mutations in GALNT3, Encoding a Protein Involved in O-linked Glycosylation, Cause Familial Tumoral Calcinosis," *Nat Genet* 36(6):579-581 (2004); Dumitrescu et al., "A Case of Familial Tumoral Calcinosis/hyperostosis-hyperphosphatemia Syndrome Due to a Compound Heterozygous Mutation in GALNT3 Demonstrating New Phenotypic Features," *Osteoporos Int* (2008); Araya et al., "A Novel Mutation in Fibroblast Growth Factor 23 Gene as a Cause of Tumoral Calcinosis," *J Clin Endocrinol Metab* 90(10):5523-5527 (2005); Chefetz et al., "A Novel Homozygous Missense Mutation in FGF23 Causes Familial Tumoral Calcinosis Associated with Disseminated Visceral Calcification," *Hum Genet* 118(2):261-266 (2005); Larsson et al., "A Novel Recessive Mutation in Fibroblast Growth Factor-23 Causes Familial Tumoral Calcinosis," *J Clin Endocrinol Metab* 90(4):2424-2427 (2005), which are hereby incorporated by reference in their entirety). The present invention suggests that excess C-terminal FGF23 fragment may aggravate hyperphosphatemia, and the resulting soft tissue calcification, by antagonizing the action of any residual, functional FGF23 ligand in these patients.

There has been a conundrum surrounding the mechanism of action of FGF23 in the kidney because Klotho is expressed in the distal convoluted tubule (Kato et al., "Establishment of the anti-Klotho monoclonal antibodies and detection of Klotho protein in kidneys," *Biochem Biophys Res Commun* 267(2):597-602 (2000), Li et al., "Immunohistochemical localization of Klotho protein in brain, kidney, and reproductive organs of mice," *Cell Struct Funct* 29(4):91-99 (2004), Tsujikawa et al., "Klotho, a gene related to a syndrome resembling human premature aging, functions in a negative regulatory circuit of vitamin D endocrine system," *Mol Endocrinol* 17(12):2393-2403 (2003), which are hereby incorporated by reference in their entirety), whereas FGF23 inhibits phosphate reabsorption in the proximal tubule (Baum et al., "Effect of fibroblast growth factor-23 on phosphate transport in proximal tubules," *Kidney Int* 68(3):1148-1153 (2005), Perwad et al., "Fibroblast growth factor 23 impairs phosphorus and vitamin D metabolism in vivo and suppresses 25-hydroxyvitamin D-1alpha-hydroxylase expression in vitro," *Am J Physiol Renal Physiol* 293(5):F1577-F1583 (2007), Larsson et al., "Transgenic mice expressing fibroblast growth factor 23 under the control of the alpha1(I) collagen promoter exhibit growth retardation, osteomalacia, and disturbed phosphate homeostasis," *Endocrinology* 145(7):3087-3094 (2004), which are hereby incorporated by reference in their entirety). A recent study suggested that FGF23 signaling initiates in the distal tubule and its effects are then transmitted to the proximal tubule through an unknown diffusible paracrine factor (Farrow et al., "Initial FGF23-mediated signaling occurs in the distal convoluted tubule," *J Am Soc Nephrol* 20(5):955-960 (2009), which is hereby incorporated by reference in its entirety). In addition to the membrane-bound isoform of Klotho, alternative splicing and proteolytic cleavage give rise to two soluble isoforms of Klotho found in the circulation (Imura et al., "Secreted Klotho protein in sera and CSF: implication for post-translational cleavage in release of Klotho protein from cell membrane," *FEBS Lett* 565(1-3):143-147 (2004), Kurosu et al., "Suppression of aging in mice by the hormone Klotho," *Science* 309(5742):1829-1833 (2005), Matsumura et al., "Identification of the human klotho gene and its two transcripts encoding membrane and secreted klotho protein," *Biochem Biophys Res Commun* 242(3):626-630 (1998), Shiraki-Iida et al., "Structure of the mouse klotho gene and its two transcripts encoding membrane and secreted protein," *FEBS Lett* 424(1-2):6-10 (1998), which are hereby incorporated by reference in their entirety). Importantly, the recombinant Klotho ectodomain that was used to reconstitute the ternary FGF23-FGFR-Klotho complex in vitro corresponds to the complete ectodomain of Klotho that is shed into the circulation by a proteolytic cleavage at the juncture between the extracellular domain and transmembrane domain (Imura et al., "Secreted Klotho protein in sera and CSF: implication for post-translational cleavage in release of Klotho protein from cell membrane," *FEBS Lett* 565(1-3):143-147 (2004), Kurosu et al., "Suppression of aging in mice by the hormone Klotho," *Science* 309(5742):1829-1833 (2005), which are hereby incorporated by reference in their entirety). Thus, the present invention points to the possibility that it is the shed soluble isoform of Klotho that makes its way to the proximal tubule to promote formation of FGF23-FGFR-Klotho ternary complex, and inhibition of phosphate reabsorption.

Example 8

The Isolated C-Terminal Tail of FGF23 Inhibits Renal Phosphate Excretion as an FGF23 Antagonist by Displacing FGF23 from its Receptor FGF23 is an important phosphaturic hormone. FGF23 fragments were examined for binding to the binary FGFR-Klotho complex, FGFR activation, sodium-dependent phosphate transport, and phosphate balance. Based on FGF23 peptides (aa 28-251, 28-179, 28-200, 180-251, and 180-200) binding to the binary FGFR-Klotho complex, the binding region was localized to aa 180-200 which provides the structural platform to design agonists and antagonists. Using FRS2α and 44/42 MAP kinase phosphorylation as readouts for FGFR activation, it was found that $FGF23^{28-200}$ was an agonist while $FGF23^{180-251}$ had no activity alone but functioned as an antagonist. Its antagonistic action was mediated by competitively displacing FGF23 from its binary cognate FGFR-Klotho complex, and the major region of antagonism was further refined to aa 180-205. Next it was examined if $FGF23^{180-251}$ is a functional antagonist in vivo. An IV injection of $FGF23^{28-251}$ into normal rats induced hypophosphatemia whereas $FGF23^{180-251}$ induced hyperphosphatemia. Excretion rate and fractional excretion of phosphate were increased by $FGF23^{28-251}$ but decreased by $FGF23^{180-251}$. $FGF23^{28-251}$ diminished the sodium-dependent phosphate transporter proteins $NaP_i$-2A and $NaP_i$-2C in the apical brush border membrane whereas $FGF23^{180-251}$ increased $NaP_i$-2A and $NaP_i$-2C protein expression. To ensure that these are direct effects on epithelia of the renal proximal tubule, phosphate uptake was studied in proximal tubule-like cells. FGF23 C-terminal peptides did not alter phosphate uptake by themselves but they completely reversed the inhibitory effect of FGF23 on phosphate uptake (aa 180-251: half max 21 nM; aa 180-205: half max between 100 nM and 500 nM). In conclusion, the isolated C-terminal tail of FGF23 is an antagonist of FGF23 and induces renal phosphate retention. This can provide the foundation for potential therapeutic interventions of hypophosphatemia where FGF23 is not down-regulated as a compensatory mechanism.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed:

1. A method of screening for compounds suitable for treatment of a hypophosphatemic condition, said method comprising:
   providing a receptor binding fragment of FGF23 consisting of the amino acid sequence of SEQ ID NO:12 or amino acid residues 1 to 21 of SEQ ID NO:11;
   providing binary FGFR-Klotho complex;
   providing one or more candidate compounds;
   combining the receptor binding fragment of FGF23, the binary FGFR-Klotho complex, and the candidate compounds under conditions effective for the receptor binding fragment of FGF23 and the binary FGFR-Klotho complex to form a ternary complex if present by themselves; and
   identifying the candidate compounds which prevent formation of the ternary complex and bind the binary FGFR-Klotho complex as being suitable in treating hypophosphatemia associated with elevated or normal FGF23.

2. The method according to claim 1, wherein the Klotho has the amino acid sequence of SEQ ID NO:7.

3. The method according to claim 1, wherein a plurality of candidate compounds are tested.

4. The method according to claim 1, wherein the FGF receptor has the amino acid sequence of SEQ ID NO:9.

5. The method according to claim 1, wherein the method is carried out using surface plasmon resonance spectroscopy.

6. The method according to claim 1, wherein the method is carried out using size-exclusion chromatography.

7. The method according to claim 1, wherein the method is carried out using a pull-down assay.

8. The method according to claim 1, wherein the method is carried out using co-immunoprecipitation.

9. The method according to claim 1, wherein the method is carried out in a cellular assay.

10. The method according to claim 1, wherein the receptor binding fragment of FGF23 consists of the amino acid sequence of SEQ ID NO:12.

11. The method according to claim 1, wherein the receptor binding fragment of FGF23 consists of amino acid residues 1 to 21 of SEQ ID NO:11.

12. The method according to claim 1, wherein the one or more candidate compounds comprise a polypeptide.

13. The method according to claim 1, wherein the one or more candidate compounds comprise an FGF23 fragment.

* * * * *

SEQUENCE LISTING

```
<160> NUMBER OF SEQ ID NOS: 24

<210> SEQ ID NO 1
<211> LENGTH: 4
<212> TYPE: PRT
<213> ORGANISM: Artificial
<220> FEATURE:
<223> OTHER INFORMATION: primer
<220> FEATURE:
<221> NAME/KEY: misc_feature
<222> LOCATION: (2)..(3)
<223> OTHER INFORMATION: Xaa can be any naturally occurring amino acid
```

<400> SEQUENCE: 1

Arg Xaa Xaa Arg
1

<210> SEQ ID NO 2
<211> LENGTH: 3018
<212> TYPE: DNA
<213> ORGANISM: Homo sapiens

<400> SEQUENCE: 2

| | | | | | |
|---|---|---|---|---|---|
| cggcaaaaag | gagggaatcc | agtctaggat | cctcacacca | gctacttgca | agggagaagg | 60 |
| aaaaggccag | taaggcctgg | gccaggagag | tcccgacagg | agtgtcaggt | ttcaatctca | 120 |
| gcaccagcca | ctcagagcag | ggcacgatgt | tgggggcccg | cctcaggctc | tgggtctgtg | 180 |
| ccttgtgcag | cgtctgcagc | atgagcgtcc | tcagagccta | tcccaatgcc | tccccactgc | 240 |
| tcggctccag | ctggggtggc | ctgatccacc | tgtacacagc | cacagccagg | aacagctacc | 300 |
| acctgcagat | ccacaagaat | ggccatgtgg | atggcgcacc | ccatcagacc | atctacagtg | 360 |
| ccctgatgat | cagatcagag | gatgctggct | tgtggtgat | acaggtgtg | atgagcagaa | 420 |
| gatacctctg | catggatttc | agaggcaaca | ttttggatc | acactatttc | gacccggaga | 480 |
| actgcaggtt | ccaacaccag | acgctggaaa | acgggtacga | cgtctaccac | tctcctcagt | 540 |
| atcacttcct | ggtcagtctg | gccgggcga | agagagcctt | cctgccaggc | atgaacccac | 600 |
| ccccgtactc | ccagttcctg | tcccggagga | acgagatccc | cctaattcac | ttcaacaccc | 660 |
| ccataccacg | gcggcacacc | cggagcgccc | aggacgactc | ggagcgggac | ccctgaacg | 720 |
| tgctgaagcc | ccgggcccgg | atgaccccgg | ccccggcctc | ctgttcacag | gagctcccga | 780 |
| gcgccgagga | caacagcccg | atggccagtg | acccattagg | ggtggtcagg | ggcggtcgag | 840 |
| tgaacacgca | cgctggggga | acgggcccgg | aaggctgccg | ccccttcgcc | aagttcatct | 900 |
| agggtcgctg | gaagggcacc | ctctttaacc | catccctcag | caaacgcagc | tcttcccaag | 960 |
| gaccaggtcc | cttgacgttc | cgaggatggg | aaaggtgaca | ggggcatgta | tggaatttgc | 1020 |
| tgcttctctg | gggtcccttc | cacaggaggt | cctgtgagaa | ccaacctttg | aggcccaagt | 1080 |
| catggggttt | caccgccttc | ctcactccat | atagaacacc | tttcccaata | ggaaacccca | 1140 |
| acaggtaaac | tagaaatttc | cccttcatga | aggtagagag | aagggtctc | tcccaacata | 1200 |
| tttctcttcc | ttgtgcctct | cctctttatc | acttttaagc | ataaaaaaa | aaaaaaaaa | 1260 |
| aaaaaaaaa | aaaagcagtg | ggttcctgag | ctcaagactt | tgaaggtgta | gggaagagga | 1320 |
| aatcggagat | cccagaagct | tctccactgc | cctatgcatt | tatgttagat | gccccgatcc | 1380 |
| cactggcatt | tgagtgtgca | aaccttgaca | ttaacagctg | aatggggcaa | gttgatgaaa | 1440 |
| acactacttt | caagccttcg | ttcttccttg | agcatctctg | gggaagagct | gtcaaaagac | 1500 |
| tggtggtagg | ctggtgaaaa | cttgacagct | agacttgatg | cttgctgaaa | tgaggcagga | 1560 |
| atcataatag | aaaactcagc | ctccctacag | ggtgagcacc | ttctgtctcg | ctgtctccct | 1620 |
| ctgtgcagcc | acagccagag | ggccagaat | ggcccactc | tgttcccaag | cagttcatga | 1680 |
| tacagcctca | ccttttggcc | ccatctctgg | tttttgaaaa | tttggtctaa | ggaataaata | 1740 |
| gcttttacac | tggctcacga | aaatctgccc | tgctagaatt | tgcttttcaa | aatggaaata | 1800 |
| aattccaact | ctcctaagag | gcatttaatt | aaggctctac | ttccaggttg | agtaggaatc | 1860 |
| cattctgaac | aaaactacaaa | aatgtgactg | ggaaggggc | tttgagagac | tgggactgct | 1920 |
| ctggggttagg | ttttctgtgg | actgaaaaat | cgtgtccttt | tctctaaatg | aagtggcatc | 1980 |

| | | | |
|---|---|---|---|
| aaggactcag | ggggaaagaa | atcaggggac atgttataga | agttatgaaa agacaaccac | 2040 |
| atggtcaggc | tcttgtctgt | ggtctctagg gctctgcagc | agcagtggct cttcgattag | 2100 |
| ttaaaactct | cctaggctga | cacatctggg tctcaatccc | cttggaaatt cttggtgcat | 2160 |
| taaatgaagc | cttaccccat | tactgcggtt cttcctgtaa | gggggctcca ttttcctccc | 2220 |
| tctcttttaaa | tgaccaccta | aaggacagta tattaacaag | caaagtcgat tcaacaacag | 2280 |
| cttcttccca | gtcactttt | tttttctcac tgccatcaca | tactaacctt atactttgat | 2340 |
| ctattctttt | tggttatgag | agaaatgttg ggcaactgtt | tttacctgat ggttttaagc | 2400 |
| tgaacttgaa | ggactggttc | ctattctgaa acagtaaaac | tatgtataat agtatatagc | 2460 |
| catgcatggc | aaatatttta | atatttctgt tttcatttcc | tgttggaaat attatcctgc | 2520 |
| ataatagcta | ttggaggctc | ctcagtgaaa gatcccaaaa | ggattttggt ggaaaactag | 2580 |
| ttgtaatctc | acaaactcaa | cactaccatc aggggttttc | tttatggcaa agccaaaata | 2640 |
| gctcctacaa | tttcttatat | ccctcgtcat gtggcagtat | ttatttattt atttggaagt | 2700 |
| ttgcctatcc | ttctatattt | atagatattt ataaaaatgt | aaccccttttt tccttcttc | 2760 |
| tgtttaaaat | aaaaataaaa | tttatctcag cttctgttag | cttatcctct ttgtagtact | 2820 |
| acttaaaagc | atgtcggaat | ataagaataa aaaggattat | gggaggggaa cattagggaa | 2880 |
| atccagagaa | ggcaaaattg | aaaaaaagat tttagaattt | taaaattttc aaagatttct | 2940 |
| tccattcata | aggagactca | atgattttaa ttgatctaga | cagaattatt taagttttat | 3000 |
| caatattgga | tttctggt | | | 3018 |

<210> SEQ ID NO 3
<211> LENGTH: 251
<212> TYPE: PRT
<213> ORGANISM: Homo sapiens

<400> SEQUENCE: 3

Met Leu Gly Ala Arg Leu Arg Leu Trp Val Cys Ala Leu Cys Ser Val
1               5                   10                  15

Cys Ser Met Ser Val Leu Arg Ala Tyr Pro Asn Ala Ser Pro Leu Leu
            20                  25                  30

Gly Ser Ser Trp Gly Gly Leu Ile His Leu Tyr Thr Ala Thr Ala Arg
        35                  40                  45

Asn Ser Tyr His Leu Gln Ile His Lys Asn Gly His Val Asp Gly Ala
    50                  55                  60

Pro His Gln Thr Ile Tyr Ser Ala Leu Met Ile Arg Ser Glu Asp Ala
65                  70                  75                  80

Gly Phe Val Val Ile Thr Gly Val Met Ser Arg Arg Tyr Leu Cys Met
                85                  90                  95

Asp Phe Arg Gly Asn Ile Phe Gly Ser His Tyr Phe Asp Pro Glu Asn
            100                 105                 110

Cys Arg Phe Gln His Gln Thr Leu Glu Asn Gly Tyr Asp Val Tyr His
        115                 120                 125

Ser Pro Gln Tyr His Phe Leu Val Ser Leu Gly Arg Ala Lys Arg Ala
    130                 135                 140

Phe Leu Pro Gly Met Asn Pro Pro Tyr Ser Gln Phe Leu Ser Arg
145                 150                 155                 160

Arg Asn Glu Ile Pro Leu Ile His Phe Asn Thr Pro Ile Pro Arg Arg
                165                 170                 175

His Thr Arg Ser Ala Glu Asp Asp Ser Glu Arg Asp Pro Leu Asn Val
            180                 185                 190

```
Leu Lys Pro Arg Ala Arg Met Thr Pro Ala Pro Ala Ser Cys Ser Gln
    195                 200                 205

Glu Leu Pro Ser Ala Glu Asp Asn Ser Pro Met Ala Ser Asp Pro Leu
    210                 215                 220

Gly Val Val Arg Gly Gly Arg Val Asn Thr His Ala Gly Gly Thr Gly
225                 230                 235                 240

Pro Glu Gly Cys Arg Pro Phe Ala Lys Phe Ile
                245                 250

<210> SEQ ID NO 4
<211> LENGTH: 1814
<212> TYPE: DNA
<213> ORGANISM: Mus musculus

<400> SEQUENCE: 4
```

| | | | | | |
|---|---|---|---|---|---|
| gaatctagcc | caggatcccc | acctcagttc | tcagcttctt | cctaggaaga | agagaaaggc | 60 |
| cagcaagggc | ccagcctgtc | tgggagtgtc | agatttcaaa | ctcagcatta | gccactcagt | 120 |
| gctgtgcaat | gctagggacc | tgccttagac | tcctggtggg | cgtgctctgc | actgtctgca | 180 |
| gcttgggcac | tgctagagcc | tatccggaca | cttccccatt | gcttggctcc | aactggggaa | 240 |
| gcctgaccca | cctgtacacg | gctacagcca | ggaccagcta | tcacctacag | atccataggg | 300 |
| atggtcatgt | agatggcacc | ccccatcaga | ccatctacag | tgccctgatg | attacatcag | 360 |
| aggacgccgg | ctctgtggtg | ataacaggag | ccatgactcg | aaggttcctt | tgtatggatc | 420 |
| tccacggcaa | cattttggga | tcgcttcact | tcagcccaga | gaattgcaag | ttccgccagt | 480 |
| ggacgctgga | gaatggctat | gacgtctact | tgtcgcagaa | gcatcactac | ctggtgagcc | 540 |
| tgggccgcgc | caagcgcatc | ttccagccgg | gcaccaaccc | gccgcccttc | tcccagttcc | 600 |
| tggctcgcag | gaacgaggtc | ccgctgctgc | atttctacac | tgttcgccca | cggcgccaca | 660 |
| cgcgcagcgc | cgaggaccca | ccggagcgcg | acccactgaa | cgtgctcaag | ccgcggcccc | 720 |
| gcgccacgcc | tgtgcctgta | tcctgctctc | gcgagctgcc | gagcgcagag | aaggtggcc | 780 |
| ccgcagccag | cgatcctctg | ggggtgctgc | gcagaggccg | tggagatgct | cgcggggcg | 840 |
| cgggaggcgc | ggataggtgt | cgccccttc | ccaggttcgt | ctaggtcccc | aggccaggct | 900 |
| gcgtccgcct | ccatcctcca | gtcggttcag | cccacgtaga | ggaaggacta | gggtacctcg | 960 |
| aggatgtctg | cttctctccc | ttccctatgg | gcctgagagt | cacctgcgag | gttccagcca | 1020 |
| ggcaccgcta | ttcagaatta | agagccaacg | gtgggaggct | ggagaggtgg | cgcagacagt | 1080 |
| tctcagcacc | cacaaatacc | tgtaattcta | gctccagggg | aatctgtact | cacacacaca | 1140 |
| cacatccaca | cacacacaca | cacacataca | tgtaatttta | aatgttaatc | tgatttaaag | 1200 |
| accccaacag | gtaaactaga | cacgaagctc | tttttatttt | attttactaa | caggtaaacc | 1260 |
| agacacttgg | cctttattag | ccgggtctct | tgcctagcat | tttaatcgat | cagttagcac | 1320 |
| gaggaaagag | ttcacgcctt | gaacacaggg | aagaggccat | ctctgcagct | tctagttact | 1380 |
| attctgggat | tcacgggtgt | ttgagtttga | gcaccttgac | cttaatgtct | tcactaggca | 1440 |
| agtcgaagaa | agacgcgcat | ttcttctctt | tgggaagagc | tttggattgg | cgggaggctg | 1500 |
| acaaggacac | ctaaaccgaa | cacatttcag | agttcagcct | cctgaggaa | tgattcgcca | 1560 |
| atgattctgt | gataggacca | gtcagtagct | tttgaatttg | ccctggctca | gcaaagtcta | 1620 |
| ccttgctagg | gtgttttgca | aaatgcaaac | gctcgaactc | tctctaaaga | ggcatttta | 1680 |
| gtgaaagcct | ccgctagcag | gttgacttgt | aatatattct | aagcgaatgt | gcccggggtg | 1740 |

```
ggggtggagg tggggtgggg gagaagggtc cttgagacct cggattgttc taggttaggg    1800
tttctgtgaa gagg                                                      1814

<210> SEQ ID NO 5
<211> LENGTH: 251
<212> TYPE: PRT
<213> ORGANISM: Mus musculus

<400> SEQUENCE: 5

Met Leu Gly Thr Cys Leu Arg Leu Leu Val Gly Val Leu Cys Thr Val
1               5                   10                  15

Cys Ser Leu Gly Thr Ala Arg Ala Tyr Pro Asp Thr Ser Pro Leu Leu
            20                  25                  30

Gly Ser Asn Trp Gly Ser Leu Thr His Leu Tyr Thr Ala Thr Ala Arg
        35                  40                  45

Thr Ser Tyr His Leu Gln Ile His Arg Asp Gly His Val Asp Gly Thr
    50                  55                  60

Pro His Gln Thr Ile Tyr Ser Ala Leu Met Ile Thr Ser Glu Asp Ala
65                  70                  75                  80

Gly Ser Val Val Ile Thr Gly Ala Met Thr Arg Arg Phe Leu Cys Met
                85                  90                  95

Asp Leu His Gly Asn Ile Phe Gly Ser Leu His Phe Ser Pro Glu Asn
            100                 105                 110

Cys Lys Phe Arg Gln Trp Thr Leu Glu Asn Gly Tyr Asp Val Tyr Leu
        115                 120                 125

Ser Gln Lys His His Tyr Leu Val Ser Leu Gly Arg Ala Lys Arg Ile
    130                 135                 140

Phe Gln Pro Gly Thr Asn Pro Pro Phe Ser Gln Phe Leu Ala Arg
145                 150                 155                 160

Arg Asn Glu Val Pro Leu Leu His Phe Tyr Thr Val Arg Pro Arg Arg
                165                 170                 175

His Thr Arg Ser Ala Glu Asp Pro Pro Glu Arg Asp Pro Leu Asn Val
            180                 185                 190

Leu Lys Pro Arg Pro Arg Ala Thr Pro Val Pro Val Ser Cys Ser Arg
        195                 200                 205

Glu Leu Pro Ser Ala Glu Glu Gly Gly Pro Ala Ala Ser Asp Pro Leu
    210                 215                 220

Gly Val Leu Arg Arg Gly Arg Gly Asp Ala Arg Gly Gly Ala Gly Gly
225                 230                 235                 240

Ala Asp Arg Cys Arg Pro Phe Pro Arg Phe Val
                245                 250

<210> SEQ ID NO 6
<211> LENGTH: 5012
<212> TYPE: DNA
<213> ORGANISM: Homo sapiens

<400> SEQUENCE: 6
cgcgcagcat gcccgccagc gccccgccgc gccgcccgcg ccgccgcccg ccgtcgctgt     60
cgctgctgct ggtgctgctg ggcctgggcg gcgccgccct cgtgcggag ccgggcgacg    120 gcgcgcagac ctgggcccgt tctcgcggc ctcctgcccc cgaggccgcg ggcctcttcc    180
agggcacctt ccccgacggc ttcctctggg ccgtgggcag cgccgcctac cagaccgagg    240
gcggctggca gcagcacggc aagggtgcgt ccatctggga tacgttcacc caccacccc    300 tggcaccccc gggagactcc cggaacgcca gtctgccgtt gggcgccccg tcgccgctgc    360
```

```
agcccgccac cggggacgta gccagcgaca gctacaacaa cgtcttccgc gacacggagg    420
cgctgcgcga gctcgggatc actcactacc gcttctccat ctcgtgggcg cgagtgctcc    480
ccaatggcag cgcgggcgtc cccaaccgcg aggggctgcg ctactaccgg cgcctgctgg    540
agcggctgcg ggagctgggc gtgcagcccg tggtcaccct gtaccactgg gacctgcccc    600
agcgcctgca ggacgcctac ggcggctggg ccaaccgcgc cctggccgac cacttcaggg    660
attacgcgga gctctgcttc cgccacttcg gcggtcaggt caagtactgg atcaccatcg    720
acaaccccta cgtggtggcc tggcacggct acgccaccgg gcgcctggcc cccggcatcc    780
ggggcagccc gcggctcggg tacctggtgg cgcacaacct cctcctggct catgccaaag    840
tctggcatct ctacaatact tctttccgtc ccactcaggg aggtcaggtg tccattgccc    900
taagctctca ctggatcaat cctcgaagaa tgaccgacca cagcatcaaa gaatgtcaaa    960
aatctctgga ctttgtacta ggttggtttg ccaaacccgt atttattgat ggtgactatc   1020
ccgagagcat gaagaataac ctttcatcta ttctgcctga ttttactgaa tctgagaaaa   1080
agttcatcaa aggaactgct gacttttttg ctctttgctt tggacccacc ttgagttttc   1140
aacttttgga ccctcacatg aagttccgcc aattggaatc tcccaacctg aggcaactgc   1200
tttcctggat tgaccttgaa tttaaccatc ctcaaatatt tattgtggaa aatggctggt   1260
ttgtctcagg gaccaccaag agagatgatg ccaaatatat gtattacctc aaaaagttca   1320
tcatggaaac cttaaaagcc atcaagctgg atggggtgga tgtcatcggg tataccgcat   1380
ggtccctcat ggatggtttc gagtggcaca gaggttacag catcaggcgt ggactcttct   1440
atgttgactt tctaagccag gacaagatgt tgttgccaaa gtcttcagcc ttgttctacc   1500
aaaagctgat agagaaaaat ggcttccctc ctttacctga aaatcagccc ctagaaggga   1560
catttccctg tgactttgct tggggagttg ttgacaacta cattcaagta gataccactc   1620
tgtctcagtt taccgacctg aatgtttacc tgtgggatgt ccaccacagt aaaaggctta   1680
ttaaagtgga tggggttgtg accaagaaga ggaaatccta ctgtgttgac tttgctgcca   1740
tccagcccca gatcgcttta ctccaggaaa tgcacgttac acattttcgc ttctccctgg   1800
actgggccct gattctccct ctgggtaacc agtcccaggt gaaccacacc atcctgcagt   1860
actatcgctg catggccagc gagcttgtcc gtgtcaacat caccccagtg gtggccctgt   1920
ggcagcctat ggccccgaac caaggactgc gcgcctcct ggccaggcag ggcgcctggg   1980
agaaccccta cactgccctg gcctttgcag agtatgcccg actgtgcttt caagagctcg   2040
gccatcacgt caagctttgg ataacgatga tgagccgta caaggaat atgacataca    2100 gtgctggcca caaccttctg aaggcccatg ccctggcttg gcatgtgtac aatgaaaagt   2160
ttaggcatgc tcagaatggg aaaatatcca tagccttgca ggctgattgg atagaacctg   2220
cctgcccttt ctcccaaaag gacaaagagg tggctgagag agttttggaa tttgacattg   2280
gctggctggc tgagcccatt ttcggctctg agattatcc atgggtgatg agggactggc   2340
tgaaccaaag aaacaatttt cttcttcctt atttcactga agatgaaaaa aagctaatcc   2400
agggtacctt tgacttttg gctttaagcc attataccac catccttgta gactcagaaa   2460
aagaagatcc aataaaatac aatgattacc tagaagtgca agaaatgacc gacatcacgt   2520
ggctcaactc ccccagtcag gtggcggtag tgccctgggg gttgcgcaaa gtgctgaact   2580
ggctgaagtt caagtacgga gacctcccca tgtacataat atccaatgga atcgatgacg   2640
ggctgcatgc tgaggacgac cagctgaggg tgtattatat gcagaattac ataaacgaag   2700
```

```
ctctcaaagc ccacatactg gatggtatca atctttgcgg atactttgct tattcgttta    2760
acgaccgcac agctccgagg tttggcctct atcgttatgc tgcagatcag tttgagccca    2820
aggcatccat gaaacattac aggaaaatta ttgacagcaa tggtttcccg ggcccagaaa    2880
ctctggaaag attttgtcca gaagaattca ccgtgtgtac tgagtgcagt ttttttcaca    2940
cccgaaagtc tttactggct ttcatagctt ttctattttt tgcttctatt atttctctct    3000
cccttatatt ttactactcg aagaaaggca gaagaagtta caaatagttc tgaacatttt    3060
tctattcatt cattttgaaa taattatgca gacacatcag ctgttaacca tttgcacctc    3120
taagtgttgt gaaactgtaa atttcataca tttgacttct agaaaacatt tttgtggctt    3180
atgacagagg ttttgaaatg ggcataggtg atcgtaaaat attgaataat gcgaatagtg    3240
cctgaatttg ttctcttttt gggtgattaa aaaactgaca ggcactataa tttctgtaac    3300
acactaacaa aagcatgaaa aataggaacc acaccaatgc aacatttgtg cagaaatttg    3360
aatgacaaga ttaggaatat tttcttctgc acccacttct aaatttaatg ttttttctgga    3420
agtagtaatt gcaagagttc gaatagaaag ttatgtacca agtaaccatt tctcagctgc    3480
cataataatg cctagtggct tcccctctgt caaatctagt ttcctatgga aaagaagatg    3540
gcagatacag gagagacgac agagggtcct aggctggaat gttcctttcg aaagcaatgc    3600
ttctatcaaa tactagtatt aatttatgta tctggttaat gacatacttg gagagcaaat    3660
tatgaaaatg tgtattttat atgattttg aggtcctgtc taaaccctgt gtccctgagg     3720
gatctgtctc actggcatct tgttgagggc cttgcacata ggaaactttt gataagtatc    3780
tgcggaaaaa caaacatgaa tcctgtgata ttgggctctt caggaagcat aaagcaattg    3840
tgaaatacag tataccgcag tggctctagg tggaggaaag gaggaaaaag tgcttattat    3900
gtgcaacatt atgattaatc tgattataca ccatttttga gcagatcttg gaatgaatga    3960
catgaccttt ccctagagaa taaggatgaa ataatcactc attctatgaa cagtgacact    4020
actttctatt ctttagctgt actgtaattt ctttgagttg atagttttac aaattcttaa    4080
taggttcaaa agcaatctgg tctgaataac actggatttg tttctgtgat ctctgaggtc    4140
tattttatgt ttttgctgct acttctgtgg aagtagcttt gaactagttt tactttgaac    4200
tttcacgctg aaacatgcta gtgatatcta gaaagggcta attaggtctc atcctttaat    4260
gccccttaaa taagtcttgc tgattttcag acagggaagt ctctctatta cactggagct    4320
gttttataga taagtcaata ttgtatcagg caagataaac caatgtcata acaggcattg    4380
ccaacctcac tgacacaggg tcatagtgta taataatata ctgtactata taatatatca    4440
tctttagagg tatgattttt tcatgaaaga taagcttttg gtaatattca ttttaaagtg    4500
gacttattaa aattggatgc tagagaatca agtttatttt atgtatatat ttttctgatt    4560
ataagagtaa tatatgttca ttgtaaaaat ttttaaaaca cagaaactat atgcaaagaa    4620
aaaataaaaa ttatctataa tctcagaacc cagaaatagc cactattaac atttcctacg    4680
tattttatt  tacatagatc atattgtata tagttagtat ctttattaat ttttattatg    4740
aaactttcct tgtcattat tagtcttcaa aagcatgatt tttaatagtt gttgagtatt     4800
ccaccacagg aatgtatcac aacttaaccg ttcccgtttg ttagactagt ttcttattaa    4860
tgttgatgaa tgttgtttaa aaataatttt gttgctacat ttactttaat ttccttgact    4920
gtaaagagaa gtaattttgc tccttgataa agtattatat taataataaa tctgcctgca    4980
actttttgcc ttctttcata atcataaaaa aa                                  5012
```

<210> SEQ ID NO 7
<211> LENGTH: 910
<212> TYPE: PRT
<213> ORGANISM: Homo sapiens

<400> SEQUENCE: 7

```
Asp Ser Arg Asn Ala Ser Leu Pro Leu Gly Ala Pro Ser Pro Leu Gln
1               5                   10                  15

Pro Ala Thr Gly Asp Val Ala Ser Asp Ser Tyr Asn Asn Val Phe Arg
            20                  25                  30

Asp Thr Glu Ala Leu Arg Glu Leu Gly Val Thr His Tyr Arg Phe Ser
        35                  40                  45

Ile Ser Trp Ala Arg Val Leu Pro Asn Gly Ser Ala Gly Val Pro Asn
    50                  55                  60

Arg Glu Gly Leu Arg Tyr Tyr Arg Arg Leu Leu Glu Arg Leu Arg Glu
65                  70                  75                  80

Leu Gly Val Gln Pro Val Val Thr Leu Tyr His Trp Asp Leu Pro Gln
                85                  90                  95

Arg Leu Gln Asp Ala Tyr Gly Gly Trp Ala Asn Arg Ala Leu Ala Asp
            100                 105                 110

His Phe Arg Asp Tyr Ala Glu Leu Cys Phe Arg His Phe Gly Gly Gln
        115                 120                 125

Val Lys Tyr Trp Ile Thr Ile Asp Asn Pro Tyr Val Val Ala Trp His
    130                 135                 140

Gly Tyr Ala Thr Gly Arg Leu Ala Pro Gly Ile Arg Gly Ser Pro Arg
145                 150                 155                 160

Leu Gly Tyr Leu Val Ala His Asn Leu Leu Ala His Ala Lys Val
                165                 170                 175

Trp His Leu Tyr Asn Thr Ser Phe Arg Pro Thr Gln Gly Gly Gln Val
                180                 185                 190

Ser Ile Ala Leu Ser Ser His Trp Ile Asn Pro Arg Arg Met Thr Asp
            195                 200                 205

His Ser Ile Lys Glu Cys Gln Lys Ser Leu Asp Phe Val Leu Gly Trp
        210                 215                 220

Phe Ala Lys Pro Val Phe Ile Asp Gly Asp Tyr Pro Glu Ser Met Lys
225                 230                 235                 240

Asn Asn Leu Ser Ser Ile Leu Pro Asp Phe Thr Glu Ser Glu Lys Lys
                245                 250                 255

Phe Ile Lys Gly Thr Ala Asp Phe Phe Ala Leu Cys Phe Gly Pro Thr
            260                 265                 270

Leu Ser Phe Gln Leu Leu Asp Pro His Met Lys Phe Arg Gln Leu Glu
        275                 280                 285

Ser Pro Asn Leu Arg Gln Leu Leu Ser Trp Ile Asp Leu Glu Phe Asn
    290                 295                 300

His Pro Gln Ile Phe Ile Val Glu Asn Gly Trp Phe Val Ser Gly Thr
305                 310                 315                 320

Thr Lys Arg Asp Asp Ala Lys Tyr Met Tyr Tyr Leu Lys Lys Phe Ile
                325                 330                 335

Met Glu Thr Leu Lys Ala Ile Lys Leu Asp Gly Val Asp Val Ile Gly
            340                 345                 350

Tyr Thr Ala Trp Ser Leu Met Asp Gly Phe Glu Trp His Arg Gly Tyr
        355                 360                 365

Ser Ile Arg Arg Gly Leu Phe Tyr Val Asp Phe Leu Ser Gln Asp Lys
    370                 375                 380
```

```
Met Leu Leu Pro Lys Ser Ser Ala Leu Phe Tyr Gln Lys Leu Ile Glu
385                 390                 395                 400

Lys Asn Gly Phe Pro Pro Leu Pro Glu Asn Gln Pro Leu Glu Gly Thr
            405                 410                 415

Phe Pro Cys Asp Phe Ala Trp Gly Val Val Asp Asn Tyr Ile Gln Val
            420                 425                 430

Asp Thr Thr Leu Ser Gln Phe Thr Asp Leu Asn Val Tyr Leu Trp Asp
            435                 440                 445

Val His His Ser Lys Arg Leu Ile Lys Val Asp Gly Val Val Thr Lys
            450                 455                 460

Lys Arg Lys Ser Tyr Cys Val Asp Phe Ala Ala Ile Gln Pro Gln Ile
465                 470                 475                 480

Ala Leu Leu Gln Glu Met His Val Thr His Phe Arg Phe Ser Leu Asp
            485                 490                 495

Trp Ala Leu Ile Leu Pro Leu Gly Asn Gln Ser Gln Val Asn His Thr
            500                 505                 510

Ile Leu Gln Tyr Tyr Arg Cys Met Ala Ser Glu Leu Val Arg Val Asn
            515                 520                 525

Ile Thr Pro Val Val Ala Leu Trp Gln Pro Met Ala Pro Asn Gln Gly
            530                 535                 540

Leu Pro Arg Leu Leu Ala Arg Gln Gly Ala Trp Glu Asn Pro Tyr Thr
545                 550                 555                 560

Ala Leu Ala Phe Ala Glu Tyr Ala Arg Leu Cys Phe Gln Glu Leu Gly
            565                 570                 575

His His Val Lys Leu Trp Ile Thr Met Asn Glu Pro Tyr Thr Arg Asn
            580                 585                 590

Met Thr Tyr Ser Ala Gly His Asn Leu Leu Lys Ala His Ala Leu Ala
            595                 600                 605

Trp His Val Tyr Asn Glu Lys Phe Arg His Ala Gln Asn Gly Lys Ile
            610                 615                 620

Ser Ile Ala Leu Gln Ala Asp Trp Ile Glu Pro Ala Cys Pro Phe Ser
625                 630                 635                 640

Gln Lys Asp Lys Glu Val Ala Glu Arg Val Leu Glu Phe Asp Ile Gly
            645                 650                 655

Trp Leu Ala Glu Pro Ile Phe Gly Ser Gly Asp Tyr Pro Trp Val Met
            660                 665                 670

Arg Asp Trp Leu Asn Gln Arg Asn Asn Phe Leu Leu Pro Tyr Phe Thr
            675                 680                 685

Glu Asp Glu Lys Lys Leu Ile Gln Gly Thr Phe Asp Phe Leu Ala Leu
            690                 695                 700

Ser His Tyr Thr Thr Ile Leu Val Asp Ser Glu Lys Glu Asp Pro Ile
705                 710                 715                 720

Lys Tyr Asn Asp Tyr Leu Glu Val Gln Glu Met Thr Asp Ile Thr Trp
            725                 730                 735

Leu Asn Ser Pro Ser Gln Val Ala Val Val Pro Trp Gly Leu Arg Lys
            740                 745                 750

Val Leu Asn Trp Leu Lys Phe Lys Tyr Gly Asp Leu Pro Met Tyr Ile
            755                 760                 765

Ile Ser Asn Gly Ile Asp Asp Gly Leu His Ala Glu Asp Asp Gln Leu
            770                 775                 780

Arg Val Tyr Tyr Met Gln Asn Tyr Ile Asn Glu Ala Leu Lys Ala His
785                 790                 795                 800
```

```
Ile Leu Asp Gly Ile Asn Leu Cys Gly Tyr Phe Ala Tyr Ser Phe Asn
            805                 810                 815

Asp Arg Thr Ala Pro Arg Phe Gly Leu Tyr Arg Tyr Ala Ala Asp Gln
        820                 825                 830

Phe Glu Pro Lys Ala Ser Met Lys His Tyr Arg Lys Ile Ile Asp Ser
        835                 840                 845

Asn Gly Phe Pro Gly Pro Glu Thr Leu Glu Arg Phe Cys Pro Glu Glu
        850                 855                 860

Phe Thr Val Cys Thr Glu Cys Ser Phe Phe His Thr Arg Lys Ser Leu
865                 870                 875                 880

Leu Ala Phe Ile Ala Phe Leu Phe Phe Ala Ser Ile Ile Ser Leu Ser
            885                 890                 895

Leu Ile Phe Tyr Tyr Ser Lys Lys Gly Arg Arg Ser Tyr Lys
        900                 905                 910

<210> SEQ ID NO 8
<211> LENGTH: 5917
<212> TYPE: DNA
<213> ORGANISM: Homo sapiens

<400> SEQUENCE: 8
agatgcaggg gcgcaaacgc caaaggagac caggctgtag gaagagaagg gcagagcgcc      60
ggacagctcg gcccgctccc cgtcctttgg ggccgcggct ggggaactac aaggcccagc     120
aggcagctgc aggggcgga ggcggaggag ggaccagcgc gggtgggagt gagagagcga     180
gccctcgcgc cccgccggcg catagcgctc ggagcgctct tgcggccaca ggcgcggcgt     240
cctcggcggc gggcggcagc tagcgggagc cgggacgccg gtgcagccgc agcgcgcgga     300
ggaacccggg tgtgccggga gctgggcggc cacgtccgga cgggaccgag accccctcgta    360 gcgcattgcg gcgacctcgc cttccccggc cgcgagcgcg ccgctgcttg aaaagccgcg     420
gaacccaagg acttttctcc ggtccgagct cggggcgccc cgcagggcgc acggtacccg     480
tgctgcagtc gggcacgccg cggcgccggg gcctccgcag ggcgatggag cccggtctgc     540
aaggaaagtg aggcgccgcc gctgcgttct ggaggagggg ggcacaaggt ctggagaccc     600 cgggtggcg acgggagccc tccccccgcc ccgcctccgg ggcaccagct ccggctccat      660
tgttcccgcc cgggctggag gcgccgagca ccgagcgccg ccgggagtcg agcgccggcc     720
gcggagctct tgcgaccccg ccaggacccg aacagagccc ggggcggcg ggccggagcc      780 ggggacgcgg gcacacgccc gctcgcacaa gccacggcgg actctcccga ggcggaacct     840
ccacgccgag cgagggtcag tttgaaaagg aggatcgagc tcactgtgga gtatccatgg     900
agatgtggag ccttgtcacc aacctctaac tgcagaactg gatgtggag ctggaagtgc      960 ctcctcttct gggctgtgct ggtcacagcc acactctgca ccgctaggcc gtccccgacc    1020
ttgcctgaac aagcccagcc ctggggagcc cctgtggaag tggagtcctt cctggtccac    1080
cccggtgacc tgctgcagct tcgctgtcgg ctgcgggacg atgtgcagag catcaactgg    1140
ctgcgggacg gggtgcagct ggcggaaagc aaccgcaccc gcatcacagg ggaggaggtg    1200
gaggtgcagg actccgtgcc cgcagactcc ggcctctatg cttgcgtaac cagcagcccc    1260
tcgggcagtg acaccaccta cttctccgtc aatgtttcag atgctctccc ctcctcggag    1320
gatgatgatg atgatgatga ctcctcttca gaggagaaag aaacagataa caccaaacca    1380
aaccgtatgc ccgtagctcc atattggaca tccccagaaa agatggaaaa gaaattgcat    1440
gcagtgccgg ctgccaagac agtgaagttc aaatgcccct tccagtggga cccaaacccc    1500
```

```
acactgcgct ggttgaaaaa tggcaaagaa ttcaaacctg accacagaat tggaggctac    1560
aaggtccgtt atgccacctg gagcatcata atggactctg tggtgccctc tgacaagggc    1620
aactacacct gcattgtgga gaatgagtac ggcagcatca accacacata ccagctggat    1680
gtcgtggagc ggtcccctca ccggcccatc ctgcaagcag ggttgcccgc caacaaaaca    1740
gtggccctgg gtagcaacgt ggagttcatg tgtaaggtgt acagtgaccc gcagccgcac    1800
atccagtggc taaagcacat cgaggtgaat gggagcaaga ttggcccaga caacctgcct    1860
tatgtccaga tcttgaagac tgctggagtt aataccaccg acaaagagat ggaggtgctt    1920
cacttaagaa atgtctcctt tgaggacgca ggggagtata cgtgcttggc gggtaactct    1980
atcggactct cccatcactc tgcatggttg accgttctgg aagccctgga agagaggccg    2040
gcagtgatga cctcgcccct gtacctggag atcatcatct attgcacagg ggccttcctc    2100
atctcctgca tggtggggtc ggtcatcgtc tacaagatga agagtggtac caagaagagt    2160
gacttccaca gccagatggc tgtgcacaag ctggccaaga gcatccctct gcgcagacag    2220
gtaacagtgt ctgctgactc cagtgcatcc atgaactctg ggttcttct ggttcggcca    2280 tcacggctct cctccagtgg gactcccatg ctagcagggg tctctgagta tgagcttccc    2340
gaagaccctc gctgggagct gcctcgggac agactggtct taggcaaacc cctgggagag    2400
ggctgctttg gcaggtggt gttggcagag ctatcgggc tggacaagga caaacccaac    2460
cgtgtgacca agtggctgt gaagatgttg aagtcggacg caacagagaa agacttgtca    2520
gacctgatct cagaaatgga gatgatgaag atgatcggga agcataagaa tatcatcaac    2580
ctgctggggg cctgcacgca ggatggtccc ttgtatgtca tcgtggagta tgcctccaag    2640
ggcaacctgc gggagtacct gcaggcccgg aggcccccag ggctggaata ctgctacaac    2700
cccagccaca cccagaggga gcagctctcc tccaaggacc tggtgtcctg cgcctaccag    2760
gtggcccgag gcatggagta tctggcctcc aagaagtgca tacaccgaga cctggcagcc    2820
aggaatgtcc tggtgacaga ggacaatgtg atgaagatag cagactttgg cctcgcacgg    2880
gacattcacc acatcgacta ctataaaaag acaaccaacg gccgactgcc tgtgaagtgg    2940
atggcacccg aggcattatt tgaccggatc tacacccacc agagtgatgt gtggtctttc    3000
ggggtgctcc tgtgggagat cttcactctg ggcggctccc catacccecgg tgtgcctgtg    3060 gaggaacttt tcaagctgct gaaggagggt caccgcatgg acaagcccag taactgcacc    3120
aacgagctgt acatgatgat gcgggactgc tggcatgcag tgccctcaca gagacccacc    3180
ttcaagcagc tggtggaaga cctggaccgc atcgtggcct tgacctccaa ccaggagtac    3240
ctggacctgt ccatgcccct ggaccagtac tcccccagct ttcccgacac ccggagctct    3300
acgtgctcct cagggagga ttccgtcttc tctcatgagc cgctgcccga ggagcctgc    3360 ctgccccgac acccagccca gcttgccaat ggcggactca aacgccgctg actgccaccc    3420
acacgccctc cccagactcc accgtcagct gtaaccctca cccacagccc ctgctgggcc    3480
caccacctgt ccgtccctgt ccccttct gctggcagga gccggctgcc taccaggggc    3540
cttcctgtgt ggcctgcctt caccccactc agctcacctc tcctccacc tcctctccac    3600 ctgctggtga gaggtgcaaa gaggcagatc tttgctgcca gccacttcat cccctcccag    3660
atgttggacc aacaccccte cctgccacca ggcactgcct ggagggcagg gagtgggagc    3720
caatgaacag gcatgcaagt gagagcttcc tgagctttct cctgtcggtt tggtctgttt    3780
tgccttcacc cataagcccc tcgcactctg gtggcaggtg ccttgtcctc agggctacag    3840
```

```
cagtagggag gtcagtgctt cgtgcctcga ttgaaggtga cctctgcccc agataggtgg      3900
tgccagtggc ttattaattc cgatactagt ttgctttgct gaccaaatgc ctggtaccag      3960
aggatggtga ggcgaaggcc aggttggggg cagtgttgtg gccctgggc ccagccccaa       4020 actgggggct ctgtatatag ctatgaagaa acacaaagt gtataaatct gagtatatat       4080
ttacatgtct ttttaaaagg gtcgttacca gagatttacc catcgggtaa gatgctcctg     4140
gtggctggga ggcatcagtt gctatatatt aaaaacaaaa aagaaaaaaa aggaaaatgt      4200
ttttaaaaag gtcatatatt ttttgctact tttgctgttt tatttttta aattatgttc      4260 taaacctatt ttcagtttag gtccctcaat aaaaattgct gctgcttcat ttatctatgg     4320
gctgtatgaa aagggtggga atgtccactg gaaagaaggg acacccacgg gccctggggc     4380
taggtctgtc ccgagggcac cgcatgctcc cggcgcaggt tccttgtaac ctcttcttcc     4440
taggtcctgc acccagacct cacgacgcac ctcctgcctc tccgctgctt ttggaaagtc    4500
agaaaaagaa gatgtctgct tcgagggcag gaaccccatc catgcagtag aggcgctggg    4560
cagagagtca aggcccagca gccatcgacc atggatggtt tcctccaagg aaaccggtgg    4620
ggttgggctg gggaggggc acctacctag gaatagccac ggggtagagc tacagtgatt     4680
aagaggaaag caagggcgcg gttgctcacg cctgtaatcc cagcactttg ggacaccgag    4740
gtgggcagat cacttcaggt caggagtttg agaccagcct ggccaactta gtgaaacccc    4800
atctctacta aaaatgcaaa aattatccag gcatggtggc acacgcctgt aatcccagct    4860
ccacaggagg ctgaggcaga atcccttgaa gctgggaggc ggaggttgca gtgagccgag    4920
attgcgccat tgcactccag cctgggcaac agagaaaaca aaaggaaaa caaatgatga     4980 aggtctgcag aaactgaaac ccagacatgt gtctgccccc tctatgtggg catggttttg    5040
ccagtgcttc taagtgcagg agaacatgtc acctgaggct agttttgcat tcaggtccct    5100
ggcttcgttt cttgttggta tgcctcccca gatcgtcctt cctgtatcca tgtgaccaga    5160
ctgtatttgt tgggactgtc gcagatcttg gcttcttaca gttcttcctg tccaaactcc    5220
atcctgtccc tcaggaacgg ggggaaaatt ctccgaatgt ttttggtttt ttggctgctt    5280
ggaatttact tctgccacct gctggtcatc actgtcctca ctaagtggat tctggctccc    5340
ccgtacctca tggctcaaac taccactcct cagtcgctat attaaagctt atattttgct    5400
ggattactgc taaatacaaa agaaagttca atatgttttc atttctgtag ggaaaatggg    5460
attgctgctt taaatttctg agctagggat ttttggcag ctgcagtgtt ggcgactatt     5520
gtaaaattct ctttgtttct ctctgtaaat agcacctgct aacattacaa tttgtattta    5580
tgtttaaaga aggcatcatt tggtgaacag aactaggaaa tgaattttta gctcttaaaa    5640
gcatttgctt tgagaccgca caggagtgtc tttccttgta aaacagtgat gataatttct    5700
gccttggccc taccttgaag caatgttgtg tgaagggatg aagaatctaa aagtcttcat    5760
aagtccttgg gagaggtgct agaaaaatat aaggcactat cataattaca gtgatgtcct    5820
tgctgttact actcaaatca cccacaaatt tccccaaaga ctgcgctagc tgtcaaataa     5880
aagacagtga aattgacctg aaaaaaaaaa aaaaaaa                               5917
```

<210> SEQ ID NO 9
<211> LENGTH: 822
<212> TYPE: PRT
<213> ORGANISM: Homo sapiens

<400> SEQUENCE: 9

```
Met Trp Ser Trp Lys Cys Leu Leu Phe Trp Ala Val Leu Val Thr Ala
1               5                   10                  15

Thr Leu Cys Thr Ala Arg Pro Ser Pro Thr Leu Pro Glu Gln Ala Gln
            20                  25                  30

Pro Trp Gly Ala Pro Val Glu Val Glu Ser Phe Leu Val His Pro Gly
        35                  40                  45

Asp Leu Leu Gln Leu Arg Cys Arg Leu Arg Asp Val Gln Ser Ile
    50                  55                  60

Asn Trp Leu Arg Asp Gly Val Gln Leu Ala Glu Ser Asn Arg Thr Arg
65                  70                  75                  80

Ile Thr Gly Glu Glu Val Glu Val Gln Asp Ser Val Pro Ala Asp Ser
                85                  90                  95

Gly Leu Tyr Ala Cys Val Thr Ser Ser Pro Ser Gly Ser Asp Thr Thr
                100                 105                 110

Tyr Phe Ser Val Asn Val Ser Asp Ala Leu Pro Ser Ser Glu Asp Asp
            115                 120                 125

Asp Asp Asp Asp Asp Ser Ser Ser Glu Glu Lys Glu Thr Asp Asn Thr
    130                 135                 140

Lys Pro Asn Arg Met Pro Val Ala Pro Tyr Trp Thr Ser Pro Glu Lys
145                 150                 155                 160

Met Glu Lys Lys Leu His Ala Val Pro Ala Ala Lys Thr Val Lys Phe
                165                 170                 175

Lys Cys Pro Ser Ser Gly Thr Pro Asn Pro Thr Leu Arg Trp Leu Lys
            180                 185                 190

Asn Gly Lys Glu Phe Lys Pro Asp His Arg Ile Gly Gly Tyr Lys Val
        195                 200                 205

Arg Tyr Ala Thr Trp Ser Ile Ile Met Asp Ser Val Val Pro Ser Asp
    210                 215                 220

Lys Gly Asn Tyr Thr Cys Ile Val Glu Asn Glu Tyr Gly Ser Ile Asn
225                 230                 235                 240

His Thr Tyr Gln Leu Asp Val Val Glu Arg Ser Pro His Arg Pro Ile
                245                 250                 255

Leu Gln Ala Gly Leu Pro Ala Asn Lys Thr Val Ala Leu Gly Ser Asn
            260                 265                 270

Val Glu Phe Met Cys Lys Val Tyr Ser Asp Pro Gln Pro His Ile Gln
        275                 280                 285

Trp Leu Lys His Ile Glu Val Asn Gly Ser Lys Ile Gly Pro Asp Asn
    290                 295                 300

Leu Pro Tyr Val Gln Ile Leu Lys Thr Ala Gly Val Asn Thr Thr Asp
305                 310                 315                 320

Lys Glu Met Glu Val Leu His Leu Arg Asn Val Ser Phe Glu Asp Ala
                325                 330                 335

Gly Glu Tyr Thr Cys Leu Ala Gly Asn Ser Ile Gly Leu Ser His His
            340                 345                 350

Ser Ala Trp Leu Thr Val Leu Glu Ala Leu Glu Glu Arg Pro Ala Val
        355                 360                 365

Met Thr Ser Pro Leu Tyr Leu Glu Ile Ile Ile Tyr Cys Thr Gly Ala
    370                 375                 380

Phe Leu Ile Ser Cys Met Val Gly Ser Val Ile Val Tyr Lys Met Lys
385                 390                 395                 400

Ser Gly Thr Lys Lys Ser Asp Phe His Ser Gln Met Ala Val His Lys
                405                 410                 415
```

```
Leu Ala Lys Ser Ile Pro Leu Arg Arg Gln Val Thr Val Ser Ala Asp
            420                 425                 430

Ser Ser Ala Ser Met Asn Ser Gly Val Leu Leu Val Arg Pro Ser Arg
            435                 440                 445

Leu Ser Ser Gly Thr Pro Met Leu Ala Gly Val Ser Glu Tyr Glu
450                 455                 460

Leu Pro Glu Asp Pro Arg Trp Glu Leu Pro Arg Asp Arg Leu Val Leu
465                 470                 475                 480

Gly Lys Pro Leu Gly Glu Gly Cys Phe Gly Gln Val Val Leu Ala Glu
                    485                 490                 495

Ala Ile Gly Leu Asp Lys Asp Lys Pro Asn Arg Val Thr Lys Val Ala
            500                 505                 510

Val Lys Met Leu Lys Ser Asp Ala Thr Glu Lys Asp Leu Ser Asp Leu
            515                 520                 525

Ile Ser Glu Met Glu Met Met Lys Met Ile Gly Lys His Lys Asn Ile
            530                 535                 540

Ile Asn Leu Leu Gly Ala Cys Thr Gln Asp Gly Pro Leu Tyr Val Ile
545                 550                 555                 560

Val Glu Tyr Ala Ser Lys Gly Asn Leu Arg Glu Tyr Leu Gln Ala Arg
                    565                 570                 575

Arg Pro Pro Gly Leu Glu Tyr Cys Tyr Asn Pro Ser His Asn Pro Glu
            580                 585                 590

Glu Gln Leu Ser Ser Lys Asp Leu Val Ser Cys Ala Tyr Gln Val Ala
            595                 600                 605

Arg Gly Met Glu Tyr Leu Ala Ser Lys Lys Cys Ile His Arg Asp Leu
            610                 615                 620

Ala Ala Arg Asn Val Leu Val Thr Glu Asp Asn Val Met Lys Ile Ala
625                 630                 635                 640

Asp Phe Gly Leu Ala Arg Asp Ile His His Ile Asp Tyr Tyr Lys Lys
                    645                 650                 655

Thr Thr Asn Gly Arg Leu Pro Val Lys Trp Met Ala Pro Glu Ala Leu
            660                 665                 670

Phe Asp Arg Ile Tyr Thr His Gln Ser Asp Val Trp Ser Phe Gly Val
            675                 680                 685

Leu Leu Trp Glu Ile Phe Thr Leu Gly Gly Ser Pro Tyr Pro Gly Val
690                 695                 700

Pro Val Glu Glu Leu Phe Lys Leu Leu Lys Glu Gly His Arg Met Asp
705                 710                 715                 720

Lys Pro Ser Asn Cys Thr Asn Glu Leu Tyr Met Met Met Arg Asp Cys
                    725                 730                 735

Trp His Ala Val Pro Ser Gln Arg Pro Thr Phe Lys Gln Leu Val Glu
            740                 745                 750

Asp Leu Asp Arg Ile Val Ala Leu Thr Ser Asn Gln Glu Tyr Leu Asp
            755                 760                 765

Leu Ser Met Pro Leu Asp Gln Tyr Ser Pro Ser Phe Pro Asp Thr Arg
770                 775                 780

Ser Ser Thr Cys Ser Ser Gly Glu Asp Ser Val Phe Ser His Glu Pro
785                 790                 795                 800

Leu Pro Glu Glu Pro Cys Leu Pro Arg His Pro Ala Gln Leu Ala Asn
                    805                 810                 815

Gly Gly Leu Lys Arg Arg
            820
```

```
<210> SEQ ID NO 10
<211> LENGTH: 224
<212> TYPE: PRT
<213> ORGANISM: Homo sapiens

<400> SEQUENCE: 10

Ala Ser Pro Leu Leu Gly Ser Ser Trp Gly Gly Leu Ile His Leu Tyr
1               5                   10                  15

Thr Ala Thr Ala Arg Asn Ser Tyr His Leu Gln Ile His Lys Asn Gly
            20                  25                  30

His Val Asp Gly Ala Pro His Gln Thr Ile Tyr Ser Ala Leu Met Ile
        35                  40                  45

Arg Ser Glu Asp Ala Gly Phe Val Val Ile Thr Gly Val Met Ser Arg
    50                  55                  60

Arg Tyr Leu Cys Met Asp Phe Arg Gly Asn Ile Phe Gly Ser His Tyr
65                  70                  75                  80

Phe Asp Pro Glu Asn Cys Arg Phe Gln His Gln Thr Leu Glu Asn Gly
                85                  90                  95

Tyr Asp Val Tyr His Ser Pro Gln Tyr His Phe Leu Val Ser Leu Gly
            100                 105                 110

Arg Ala Lys Arg Ala Phe Leu Pro Gly Met Asn Pro Pro Pro Tyr Ser
        115                 120                 125

Gln Phe Leu Ser Arg Arg Asn Glu Ile Pro Leu Ile His Phe Asn Thr
    130                 135                 140

Pro Ile Pro Arg Arg His Thr Arg Ser Ala Glu Asp Asp Ser Glu Arg
145                 150                 155                 160

Asp Pro Leu Asn Val Leu Lys Pro Arg Ala Arg Met Thr Pro Ala Pro
                165                 170                 175

Ala Ser Cys Ser Gln Glu Leu Pro Ser Ala Glu Asp Asn Ser Pro Met
            180                 185                 190

Ala Ser Asp Pro Leu Gly Val Val Arg Gly Gly Arg Val Asn Thr His
        195                 200                 205

Ala Gly Gly Thr Gly Pro Glu Gly Cys Arg Pro Phe Ala Lys Phe Ile
    210                 215                 220

<210> SEQ ID NO 11
<211> LENGTH: 72
<212> TYPE: PRT
<213> ORGANISM: Homo sapiens

<400> SEQUENCE: 11

Ser Ala Glu Asp Asp Ser Glu Arg Asp Pro Leu Asn Val Leu Lys Pro
1               5                   10                  15

Arg Ala Arg Met Thr Pro Ala Pro Ala Ser Cys Ser Gln Glu Leu Pro
            20                  25                  30

Ser Ala Glu Asp Asn Ser Pro Met Ala Ser Asp Pro Leu Gly Val Val
        35                  40                  45

Arg Gly Gly Arg Val Asn Thr His Ala Gly Gly Thr Gly Pro Glu Gly
    50                  55                  60

Cys Arg Pro Phe Ala Lys Phe Ile
65                  70

<210> SEQ ID NO 12
<211> LENGTH: 26
<212> TYPE: PRT
<213> ORGANISM: Homo sapiens
```

<400> SEQUENCE: 12

Ser Ala Glu Asp Asp Ser Glu Arg Asp Pro Leu Asn Val Leu Lys Pro
1               5                   10                  15

Arg Ala Arg Met Thr Pro Ala Pro Ala Ser
            20                  25

<210> SEQ ID NO 13
<211> LENGTH: 20
<212> TYPE: DNA
<213> ORGANISM: Artificial
<220> FEATURE:
<223> OTHER INFORMATION: primer

<400> SEQUENCE: 13
tgatttgcat tctccaccaa                                                    20

<210> SEQ ID NO 14
<211> LENGTH: 20
<212> TYPE: DNA
<213> ORGANISM: Artificial
<220> FEATURE:
<223> OTHER INFORMATION: primer

<400> SEQUENCE: 14
cttctccccg cttttcttct                                                    20

<210> SEQ ID NO 15
<211> LENGTH: 20
<212> TYPE: DNA
<213> ORGANISM: Artificial
<220> FEATURE:
<223> OTHER INFORMATION: primer

<400> SEQUENCE: 15
tatgggccag atggattacc                                                    20

<210> SEQ ID NO 16
<211> LENGTH: 20
<212> TYPE: DNA
<213> ORGANISM: Artificial
<220> FEATURE:
<223> OTHER INFORMATION: primer

<400> SEQUENCE: 16
gcacgtatac tccccagcat                                                    20

<210> SEQ ID NO 17
<211> LENGTH: 20
<212> TYPE: DNA
<213> ORGANISM: Artificial
<220> FEATURE:
<223> OTHER INFORMATION: primer

<400> SEQUENCE: 17
acctggtgtc ctgtgcctac                                                    20

<210> SEQ ID NO 18
<211> LENGTH: 20
<212> TYPE: DNA
<213> ORGANISM: Artificial
<220> FEATURE:
<223> OTHER INFORMATION: primer

<400> SEQUENCE: 18
cattcgatgg ccctctttta                                               20

<210> SEQ ID NO 19
<211> LENGTH: 20
<212> TYPE: DNA
<213> ORGANISM: Artificial
<220> FEATURE:
<223> OTHER INFORMATION: primer

<400> SEQUENCE: 19
ctgaagcaca tcgaggtcaa                                               20

<210> SEQ ID NO 20
<211> LENGTH: 20
<212> TYPE: DNA
<213> ORGANISM: Artificial
<220> FEATURE:
<223> OTHER INFORMATION: primer

<400> SEQUENCE: 20
cctgactcca gggagaactg                                               20

<210> SEQ ID NO 21
<211> LENGTH: 20
<212> TYPE: DNA
<213> ORGANISM: Artificial
<220> FEATURE:
<223> OTHER INFORMATION: primer

<400> SEQUENCE: 21
agccctcgaa agatgactga                                               20

<210> SEQ ID NO 22
<211> LENGTH: 20
<212> TYPE: DNA
<213> ORGANISM: Artificial
<220> FEATURE:
<223> OTHER INFORMATION: primer

<400> SEQUENCE: 22
acaaaccagc cattctccac                                               20

<210> SEQ ID NO 23
<211> LENGTH: 20
<212> TYPE: DNA
<213> ORGANISM: Artificial
<220> FEATURE:
<223> OTHER INFORMATION: primer

<400> SEQUENCE: 23
gtgggggatg aggcccagag                                               20

<210> SEQ ID NO 24
<211> LENGTH: 20
<212> TYPE: DNA
<213> ORGANISM: Artificial
<220> FEATURE:
<223> OTHER INFORMATION: primer

<400> SEQUENCE: 24
agctgtggtg gtgaaactgt                                               20